(12) United States Patent  (10) Patent No.: US 8,796,470 B2
Searle et al.  (45) Date of Patent: *Aug. 5, 2014

(54) SUBSTITUTED OCTAHYDROCYCLOPENTA[C]PYRROLES AS CALCIUM CHANNEL MODULATORS

(75) Inventors: Xenia B. Searle, Grayslake, IL (US); Ming C. Yeung, Grayslake, IL (US); Michael R. Schrimpf, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/114,368

(22) Filed: May 24, 2011

(65) Prior Publication Data

US 2011/0294854 A1  Dec. 1, 2011

Related U.S. Application Data

(60) Provisional application No. 61/348,101, filed on May 25, 2010.

(51) Int. Cl.
*C07D 209/52* (2006.01)
*C07D 401/04* (2006.01)
*A61K 31/44* (2006.01)
*A61K 31/40* (2006.01)

(52) U.S. Cl.
USPC ......... 548/515; 546/276.7; 514/339; 514/412

(58) Field of Classification Search
None
See application file for complete search history.

(56) References Cited

U.S. PATENT DOCUMENTS

| | | |
|---|---|---|
| 2003/0232818 A1 | 12/2003 | Anderson et al. |
| 2005/0148587 A1 | 7/2005 | Fraser et al. |
| 2010/0093730 A1 | 4/2010 | Bhatia et al. |
| 2010/0130558 A1 | 5/2010 | Stewart et al. |
| 2010/0261773 A1 | 10/2010 | Lindsley et al. |

FOREIGN PATENT DOCUMENTS

| | | | |
|---|---|---|---|
| EP | 0359172 A1 | 3/1990 | |
| WO | WO 9510519 A1 * | 4/1995 | |
| WO | WO0059882 A1 | 10/2000 | |
| WO | 2005079496 A2 | 9/2005 | |
| WO | 2006012396 A1 | 2/2006 | |
| WO | 2006018280 A2 | 2/2006 | |
| WO | 2006113471 A2 | 10/2006 | |
| WO | 2010039947 A1 | 4/2010 | |
| WO | 2010054398 A1 | 5/2010 | |
| WO | 2010062927 A2 | 6/2010 | |
| WO | 2010068851 A1 | 6/2010 | |

OTHER PUBLICATIONS

Angeli F., et al., "Calcium Channel Blockade to Prevent Stroke in Hypertension," American Journal of Hypertension, 2004, vol. 17 (9), pp. 817-822.

Arulmozhi D.K., et al., "Migraine: Current Concepts and Emerging Therapies," Vascular Pharmacology, 2005, vol. 43 (3), pp. 176-187.
Bao J., et al., "Differences in $Ca^{2+}$ Channels Governing Generation of Miniature and Evoked Excitatory Synaptic Currents in Spinal Laminae I and II," The Journal of Neuro Science, 1998, vol. 18 (21), pp. 8740-8750.
Barone F.C., et al., "SB 201823-A Antagonizes Calcium Currents in Central Neurons and Reduces the Effects of Focal Ischemia in Rats and Mice," Stroke, 1995, vol. 26 (9), pp. 1683-1690.
Bell T.J., et al., "Cell Specific Alternative Splicing Increases Calcium Channel Current Density in the Pain Pathway," Neuron, 2004, vol. 41, pp. 127-138.
Benington J.H., et al., "Cellular and Molecular Connections Between Sleep and Synaptic Plasticity," Progress in Neurobiology, 2003, vol. 69 (2), pp. 71-101.
Berge, S. M. et al., "Pharmaceutical Salts," Journal of Pharmaceutical Sciences, 1977, vol. 66 (1), pp. 1-19.
Beuckmann C.T., et al., "N-Type Calcium Channel $α_{1B}$ Subunit($Ca_v2.2$) Knock-Out Mice Display Hyperactivity and Vigilance State Differences," The Journal of Neuro Science, 2003, vol. 23 (17), pp. 6793-6797.
Bhatia R., et al., "Fresh and Globular Amyloid β Protein (1-42) Induces Rapid Cellular Degeneration: Evidence for AβP Channel-Mediated Cellular Toxicity," The FASEB Journal, 2000, vol. 14 (9), pp. 1233-1243.
Bhattacharjee A., et al., "T-Type Calcium Channels Facilitate Insulin Secretion by Enhancing General Excitability in the Insulin-Secreting β-Cell Line, INS-1," Endocrinology, 1997, vol. 138 (9), pp. 3735-3740.
Bilici D., et al., "Protective Effect of T-Type Calcium Channel Blocker in Histamine-Induced Paw Inflammation in Rat," Pharmacological Research, 2001, vol. 44 (6), pp. 527-531.
Bourinet E., et al., "Silencing of the $Ca_v3.2$ T-type Calcium Channel Gene in Sensory Neurons Demonstrates its Major Role in Nociception," The EMBO Journal, 2005, vol. 24 (2), pp. 315-324.
Bowersox S.S., et al., "Selective N-Type Neuronal Voltage-Sensitive Calcium Channel Blocker SNX-111 Produces Spinal Antinociception in Rat Models of Acute Persistent and Neuropathic Pain," The Journal of Pharmacology and Experimental Therapeutics, 1996, vol. 279 (3), pp. 1243-1249.
Castiglioni A.J., et al., "Alternative Splicing in the C-Terminus of $Ca_v2.2$ Controls Expression and Gating of N-Type Calcium Channels," The Journal of Physiology, 2006, vol. 576 (1), pp. 119-134.
Cavalli A., et al., "Multi-Target Directed Ligands to Combat Neurodegenerative Diseases," Journal of Medicinal Chemistry, 2008, vol. 51 (3), pp. 347-372.

(Continued)

Primary Examiner — Nyeemah A Grazier

(57) ABSTRACT

The present application relates to calcium channel inhibitors containing compounds of formula (I)

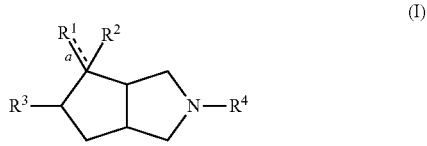

wherein α, $R^1$, $R^2$, $R^3$, and $R^4$ are as defined in the specification. The present application also relates to compositions comprising such compounds, and methods of treating conditions and disorders using such compounds and compositions.

7 Claims, No Drawings

(56) References Cited

OTHER PUBLICATIONS

Chaplan S.R., et al., "Role of Voltage-Dependent Calcium Channel Subtypes in Experimental Tactile Allodynia," The Journal of Pharmacology and Experimental Therapeutics, 1994, vol. 269 (3), pp. 1117-1123.

Chen C.C., et al., "Abnormal Coronary Function in Mice Deficient in $\alpha_{1H}$ T-type $Ca^{2+}$ Channels," Science, 2003, vol. 302 (5649), pp. 1416-1418.

Choi S., et al., "Attenuated Pain Responses in Mice Lacking $Ca_V3.2$ T-type Channels," Genes Brain and Behavior, 2007, vol. 6 (5), pp. 425-431.

Cizkova D., et al., "Localization of N-Type $Ca^{2+}$ Channels in the Rat Spinal Cord Following Chronic Constrictive Nerve Injury," Experimental Brain Research, 2002, vol. 147 (4), pp. 456-463.

Colbourne F., et al., "Continuing Postischemic Neuronal Death in CA1: Influence of Ischemia Duration and Cytoprotective Doses of NBQX and SNX-111 in Rats," Stroke, 1999, vol. 30 (3), pp. 662-668.

Croom K.F., et al., "A Review of the Use of Modified-Release Formulations in the Treatment of Hypertension and Angina Pectoris," Drugs, 2006, vol. 66 (4), pp. 497-528.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Darszon A., et al., "Ion Channels in Sperm Physiology," Physiological Reviews, 1999, vol. 79 (2), pp. 481-510.

Dolphin A.C., "A Short History of Voltage-Gated Calcium Channels," British Journal of Pharmacology, 2006, vol. 147, pp. S56-S62.

Evans A.R., et al., "Differential Regulation of Evoked Peptide Release by Voltage-Sensitive Calcium Channels in Rat Sensory Neurons," Brain Research, 1996, vol. 712 (2), pp. 265-273.

Feng Z.P., et al., "Determinants of Inhibition of Transiently Expressed Voltage-Gated Calcium Channels by ω-Conotoxins GVIA and MVIIA," The Journal of Biological Chemistry, 2003, vol. 278 (22), pp. 20171-20178.

Geldenhuys W.J., et al., "Structure-Activity Relationships of Pentacycloundecylamines at the N-Methyl-D-Aspartate Receptor," Bioorganic and Medicinal Chemistry, 2007, vol. 15 (3), pp. 1525-1532.

Gitlin M., "Treatment-Resistant Bipolar Disorder," Molecular Psychiatry, 2006, vol. 11 (3), pp. 227-240.

Gladstone J.P., et al., "Current and Emerging Treatment Options for Migraine and Other Primary Headache Disorders," Expert Revies of Neurotherapeutics, 2003, vol. 3 (6), pp. 845-872.

Gould R.J., et al., "Antischizophrenic Drugs of the Diphenylbutylpiperidine Type Act as Calcium Channel Antagonists," Proceeding of the National Academy of Sciences of the USA, 1983, vol. 80 (16), pp. 5122-5125.

Gray A.C., et al., "Neuronal Calcium Channels: Splicing for Optimal Performance," Cell Calcium, 2007, vol. 42 (4-5), pp. 409-417.

Greene, T.W., et al., Protective Groups in Organic Synthesis, 3rd Edition, John Wiley and Sons, Inc., 1999, Table of Contents.

Hatakeyama S., et al., "Differential Nociceptive Responses in Mice Lacking the $\alpha_{1B}$ Subunit of N-Type $Ca^{2+}$ Channels," Neuroreport, 2001, vol. 12 (11), pp. 2423-2427.

Heinemann U., et al., "Extracellular Free Calcium and Potassium during Paroxysmal Activity in the Cerebral Cortex of the Cat," Experimental Brain Research, 1977, vol. 27 (3-4), pp. 237-243.

Heinke B., et al., "Pre-and Postsynaptic Contributions of Voltage-Dependent Ca2+ Channels to Nociceptive Transmission in Rat Spinal Laminal Neurons," The European Journal of Neurosciences, 2004, vol. 19 (1), pp. 103-111.

Ino M., et al., "Functional Disorders of the Sympathetic Nervous System in Mice Lacking the $\alpha_{1B}$ Subunit ($Ca_v2.2$) of N-Type Calcium Channels," Proceeding of the National Academy of Sciences of the USA, 2001, vol. 98 (9), pp. 5323-5328.

Jagodic M.M., et al., "Cell-Specific Alterations of T-type Calcium Current in Painful Diabetic Neuropathy Enhance Excitability of Sensory Neurons," Journal of Neuroscience, 2007, vol. 27 (12), pp. 3305-3316.

Jagodic M.M., et al., "Upregulation of the T-Type Calcium Current in Small Rat Sensory Neurons after Chronic Constrictive Injury of the Sciatic Nerve," Journal of Neurophysiology, 2008, vol. 99 (6), pp. 3151-3156.

Kim C., et al., "Altered Nociceptive Response in Mice Deficient in the $\alpha_{1B}$ Subunit of the Voltage-Dependent Calcium Channel," Molecular and Cellular Neurosciences, 2001, vol. 18 (2), pp. 235-245.

Levy N.A., et al., "Calcium Channel Antagonists for the Treatment of Bipolar Disorder," Bipolar Disorders, 2000, vol. 2 (2), pp. 108-119.

Little H.J., et al., "Calcium Channel Antagonists Decrease the Ethanol Withdrawal Syndrome," Life Sciences, 1986, vol. 39 (22), pp. 2059-2065.

Liu L., et al., "In Vivo Analysis of Voltage-Dependent Calcium Channels," Journal of Bioenegetics and Biomembrances, 2003, vol. 35 (6), pp. 671-685.

Lorton D., "β-Amyloid-Induced IL-1 β Release from an Activated Human Monocyte Cell Line is Calcium-and G-Protein-Dependent," Mechanisms of Ageing and Development, 1997, vol. 94 (1-3), pp. 199-211.

Lubin M.L., et al., "A Nonadherent Cell-Based HTS Assay for N-Type Calcium Channel using Calcium 3 Dye," Assay and Drug Development Technologies, 2006, vol. 4 (6), pp. 689-694.

Luebke J.I., et al., "Multiple Calcium Channel Types Control Glutamatergic Synaptic Transmission in the Hippocampus," Neuron, 1993, vol. 11 (5), pp. 895-902.

Luo Z.D., et al., "Upregulation of Dorsal Root Ganglion α2D Calcium Channel Subunit and its Correlation with Allodynia in Spinal Nerve-Injured Rats," The Journal of Neuro Science, 2001, vol. 21 (6), pp. 1868-1875.

Malmberg A.B., et al., "Voltage-Sensitive Calcium Channels in Spinal Nociceptive Processing: Blockade of N-and P-Type Channels Inhibits Formalin-Induced Nociception," The Journal of Neuro Science, 1994, vol. 14 (8), pp. 4882-4890.

Mason R.P., et al., "Antioxidant and Cytoprotective Activities of the Calcium Channel Blocker Mibefradil," Biochemical Pharmacology, 1998, vol. 55 (11), pp. 1843-1852.

Matthews E.A., et al., "Effects of Spinally Delivered N- and P-Type Voltage-Dependent Calcium Channel Antagonists on Dorsal Horn Neuronal Responses in a Rat Model of Neuropathy," Pain, 2001, vol. 92 (1-2), pp. 235-246.

McGivern J.G., "Targeting N-Type and T-Type Calcium Channels for the Treatment of Pain," Drug Discovery Today, 2006, vol. 11 (5-6), pp. 245-253.

Miljanich G.P.,et al., "Antagonists of Neuronal Calcium Channels: Structure, Function and Therapeutic Implications," Annual Review of Pharmacology and Toxicology, 1995, vol. 35, pp. 707-734.

Newton R.A., et al., "Dorsal Root Ganglion Neurons Show Increased Expression of the Calcium Channel α2D-1 Subunit Following Partial Sciatic Nerve Injury," Molecular Brain Research, 2001, vol. 95 (1-2), pp. 1-8.

Nordskog B.K., et al., "Diurnal Gene Expression Patterns of T-type Calcium Channels and their Modulation by Ethanol," Neuroscience, 2006, vol. 141 (3), pp. 1365-1373.

Olivera B.M., et al., "Calcium Channel Diversity and Neurotransmitter Release: The ω-Conotoxins and ω-Agatoxins," Annual Review of Biochemistry, 1994, vol. 63, pp. 823-867.

Otoom S., et al., "Nifedipine Inhibits Picrotoxin-Induced Seizure Activity: Further Evidence on the Involvement of L-Type Calcium Channel Blockers in Epilepsy," Fundamental & Clinical Pharmacology, 2006, vol. 20 (2), pp. 115-119.

Perez-Reyes E., et al., "Molecular Pharmacology of Human $Ca_v3.2$ T-type $Ca^{2+}$ Channels: Block by Antihypertensives, Antiarrhythmics, and their Analogs," Journal of Pharmacology and Experimental Therapeutics, 2009, vol. 328 (2), pp. 621-627.

Pietrobon D. "Function and Dysfunction of Synaptic Calcium Channels: Insights from Mouse Models," Current Opinion in Neurobiology, 2005, vol. 15 (3), pp. 257-265.

Prescott D.M., "Methods in Cell Biology", Academic Press, 1976, Table of Contents.

Raingo J., et al., "Alternative Splicing Controls G Protein-Dependent Inhibition of N-Type Calcium Channels in Nociceptors," Nature Neuroscience, 2007, vol. 10 (3), pp. 285-292.

(56) References Cited

OTHER PUBLICATIONS

Rodnitzky R.L., "Can Calcium Antagonists Provide a Neuroprotective Effect in Parkinson'S Disease?," Drugs, 1999, vol. 57 (6), pp. 845-849.

Saade S., et al., "The L-Type Calcium Channel Blocker Nimodipine Mitigates "Learned Helplessness" in Rats," Pharmacology, Biochemistry and Behavior, 2003, vol. 74 (2), pp. 269-278.

Saegusa H., et al., "Suppression of Inflammatory and Neuropathic Pain Symptoms in Mice Lacking the N-Type $Ca^{2+}$ Channel," The EMBO Journal, 2001, vol. 20 (10), pp. 2349-2356.

Santora V.J., et al., "A new family of $H_3$ Receptor Antagonists Based on the Natural Product Conessine," Bioorganic & Medicinal Chemistry Letters, 2008, vol. 18 (4), pp. 1490-1494.

Scott D.A., et al., "Actions of Intrathecal ω-Conotoxins CVID GVIA MVIIA and Morphine in Acute and Neuropathic Pain in the Rat," European Journal of Pharmacology, 2002, vol. 451 (3), pp. 279-286.

Shin H.S., et al., "T-type $Ca^{2+}$ Channels as Therapeutic Targets in the Nervous System," Current Opinion in Pharmacology, 2008, vol. 8 (1), pp. 33-41.

Smith M.T., et al., "The Novel N-Type Calcium Channel Blocker, AM336, Produces Potent Dose-Dependent Antinociception after Intrathecal Dosing in Rats and Inhibits Substance P Release in Rat Spinal Cord Slices," Pain, 2002, vol. 96 (1-2), pp. 119-127.

Takahashi T., et al., "Different Types of Calcium Channels Mediate Central Synaptic Transmission," Nature, 1993, vol. 366 (6451), pp. 156-158.

Takei T., et al., "Increased Sensitivity to Halothane but Decreased Sensitivity to Propofol in Mice Lacking the N-Type $Ca^{2+}$ Channel," Neuroscience Letters, 2003, vol. 350 (1), pp. 41-45.

Talley E.M., et al., "Differential Distribution of Three Members of a Gene Family Encoding Low Voltage-activated (T-type) Calcium Channels," Journal of Neuroscience, 1999, vol. 19 (6), pp. 1895-1911.

Tort A.B., et al., "Atypical Antipsychotic Profile of Flunarizine in Animal Models," Psychopharmacology, 2005, vol. 177 (3), pp. 344-348.

Urban M.O., et al., "Medullary N-Type and P/Q-Type Calcium Channels Contribute to Neuropathy-Induced Allodynia," Neuroreport, 2005, vol. 16 (6), pp. 563-566.

Uslaner J.M., et al., "T-type Calcium Channel Antagonism Decreases Motivation for Nicotine and Blocks Nicotine- and Cue-induced Reinstatement for a Response Previously Reinforced with Nicotine," Biological Psychiatry, 2010, vol. 68 (8), pp. 712-718.

Uslaner J.M., et al., "T-type Calcium Channel Antagonism Produces Antipsychotic-like Effects and Reduces Stimulant-induced Glutamate Release in the Nucleus Accumbens of Rats," Neuropharmacology, 2010, pp. 1-9.

Vagnucci A.H., et al., "Alzheimer's Disease and Angiogenesis," The Lancet, 2003, vol. 361 (9357), pp. 605-608.

Veng L.M., et al., "Age-Related Working Memory Impairment is Correlated with Increases in the L-Type Calcium Channel Protein $α_{1D}$ ($Ca_v1.3$) in Area CA1 of the Hippocampus and both are Ameliorated by Chronic Nimodipine Treatment," Molecular Brain Research, 2003, vol. 110 (2), pp. 193-202.

Vezzani A., et al., "Effects of Various Calcium Channel Blockers on Three Different Models of Limbic Seizures in Rats," Neuropharmacology, 1988, vol. 27 (5), pp. 451-458.

Wang Y.X., et al., "Effects of Intrathecal Administration of Ziconotide a Selective Neuronal N-Type Calcium Channel Blocker on Mechanical Allodynia and Heat Hyperalgesia in a Rat Model of Postoperative Pain," Pain, 2000, vol. 84 (2-3), pp. 151-158.

Westenbroek R.E., et al., "Localization of $Ca^{2+}$ Channel Subtypes on Rat Spinal Motor Neurons Interneurons and Nerve Terminals," The Journal of Neuro Science, 1998, vol. 18 (16), pp. 6319-6330.

Yamamoto T., et al., "Differential Effects of Intrathecally Administered N- and P-Type 1:1 Voltage-Sensitive Calcium Channel Blockers upon Two Models of Experimental Mononeuropathy in the Rat," Brain Research, 1998, vol. 794 (2), pp. 329-332.

Yokoyama K., et al., "Plastic Change of N-Type Ca Channel Expression after Preconditioning is Responsible for Prostaglandin $E_2$-Induced Long-Lasting Allodynia," Anesthesiology, 2003, vol. 99 (6), pp. 1364-1370.

Zanchetti A., et al., "Calcium Antagonist Lacidipine Slows Down Progression of Asymptomatic Carotid Atherosclerosis. Principal Results of the European Lacidipine Study on Atherosclerosis (ELSA), a Randomized, Double-Blind, Long-Term Trial," Circulation, 2002, vol. 106 (19), pp. 2422-2427.

International Search Report and Written Opinion for PCT/US2011/037818 dated Feb. 13, 2013.

* cited by examiner

SUBSTITUTED OCTAHYDROCYCLOPENTA[C]PYRROLES AS CALCIUM CHANNEL MODULATORS

CROSS-REFERENCE TO RELATED APPLICATIONS

This application claims priority to U.S. Provisional Application Ser. No. 61/348,101 filed May 25, 2010, which is incorporated by reference in its entirety.

TECHNICAL FIELD

The present application relates to compounds that are calcium channel blockers, compositions comprising such compounds, and methods of treating conditions and disorders using such compounds and compositions.

BACKGROUND

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A. C. British Journal of Pharmacology 2006, 147 (Suppl. 1), S56-S62.). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~−30 mV) and are involved in "presynaptic" neurotransmission (McGivern J. G. Drug Discovery Today 2006, 11, 245-253.). T-type channels are activated at relatively negative membrane potentials (~−60 mV) and are primarily involved in "postsynaptic" excitability (Shin, H.-S.; et al. Curr. Opin. in Pharmacology 2008, 8, 33-41.).

N-type channel $\alpha_1$ subunits are encoded by a single gene ($\alpha_1$B or $Ca_v2.2$) in contrast to pharmacologically defined L- and T-type currents that are encoded by multiple $\alpha_1$-subunit genes. A diversity of N-type channels arises due to extensive alternative splicing of the α subunit gene that generates variants with different expression patterns and GPCR-modulated biophysical properties (Gray, A. C.; et al. Cell Calcium, 2007, 42(4-5), 409-417.). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M.; et al. Proc. Natl. Acad. Sci. USA 2001, 98(9), 5323-5328). In pain pathways, N-type channels are expressed in the rostral ventral medulla, an important site of descending pain modulation (Urban, M. O.; et al. Neuroreport 2005, 16(6), 563-566.) and are a major contributor to the synaptic neurotransmission that occurs between C/Aδ nociceptors and spinal lamina I neurons (Bao, J.; et al. J. Neurosci. 1998, 18(21), 8740-50. Heinke, B.; et al. Eur. J. Neurosci. 2004, 19(1), 103-111.). In contrast, P/Q type channels are expressed almost exclusively in laminae II-IV of the spinal cord and show little co-localization with Substance P and N-type channels (Westenbroek, R. E.; et al. J. Neurosci. 1998, 18(16), 6319-6330.).

Following nerve injury there is increased expression of $Ca_v2.2$ (Westenbroek, R. E.; et al. J. Neurosci. 1998, 18(16), 6319-6330. Cizkova, D.; et al. Exp. Brain Res. 2002, 147, 456-463. Yokoyama, K.; et al. Anesthesiology 2003, 99(6), 1364-1370.) and α2δ1 subunits (Luo, Z. D.; et al. J. Neurosci. 2001, 21(6), 1868-1875. Newton, R. A.; et al. Mol. Brain. Res. 2001, 95(1-2), 1-8.) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T. J.; et al. Neuron 2004, 41(1), 127-138.). These channels have distinct electrophysiological properties and current densities (Castiglioni, A. J.; et al. J. Physiol. 2006, 576(Pt 1), 119-134.) compared to wild-type $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; et al. Nat. Neurosci. 2007, 10(3), 285-292.). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M.; et al. Proc. Natl. Acad. Sci. USA 2001, 98(9), 5323-5328. Kim, C.; et al. Mol. Cell. Neurosci. 2001, 18(2), 235-245. Hatakeyama, S.; et al. Neuroreport 2001, 12(11), 2423-2427. Liu; L.; et al. J. Bioenerg. Biomembr. 2003, 35(6), 671-685.). This finding suggests that other types of $Ca_v$ channels are able to compensate for the lack of $Ca_v2.2$ channels at most synapses in these mice (Pietrobon, D. Curr. Opin. Neurobiol. 2005, 15(3), 257-265.). $Ca_v2.2$ deficient mice are resistant to the development of inflammatory and neuropathic pain (Kim, C.; et al. Mol. Cell. Neurosci. 2001, 18(2), 235-245. Hatakeyama, S.; et al. Neuroreport 2001, 12(11), 2423-2427. Saegusa, H.; et al. EMBO J. 2001, 20(10), 2349-2356.), have decreased sympathetic nervous system function (Ino, M.; et al. Proc. Natl. Acad. Sci. USA 2001, 98(9), 5323-5328.), and altered responses to both ethanol and anesthetics (Newton, R. A.; et al. Brain Res. Mol. Brain. Res. 2001, 95(1-2), 1-8. Takei, R. et al. Neurosci. Lett. 2003, 350(1), 41-45.). Additional behavioral studies indicate that $Ca_v2.2$ knockout mice are less anxious, are hyperactive, and show enhanced vigilance compared to wild-type littermates (Beuckmann, C. T.; et al. J. Neurosci. 2003, 23(17), 6793-6797.).

N- and P/Q-type channels are localized at neuronal synaptic junctions and contribute significantly to neurotransmitter release (Olivera, B. M.; et al. Annu Rev. Biochem. 1994, 63, 823-867. Miljanich, G. P.; et al. Annu Rev. Pharmacol. Toxicol. 1995, 35, 707-734.). N-type channels play a major role in the release of glutamate, acetylcholine, dopamine, norepinephrine, GABA, substance P and calcitonin gene-related protein (CGRP). P/Q-type channels may be involved in the release of glutamate, aspartate, 5HT, GABA and probably glycine (Pietrobon, D. Curr. Opin. Neurobiol. 2005, 15(3), 257-265.).

L, P/Q and N-type channels are blocked by channel specific antagonists i.e., dihydropyridines, ω-agatoxin IVA and ω-conotoxin MVIIA/ziconotide, respectively. Agatoxin IVa has been shown to block excitatory (Luebke, J. I.; et al. Neuron 1993, 11(5), 895-902.) as well as inhibitory neurotransmission (Takahashi, T.; et al. Nature 1993, 366(6451), 156-158.). Intrathecal injection of selective N-type channel blockers (e.g. conotoxin-derived peptides such as GVIA, MVIIA (ziconotide), and CVID) significantly attenuates pain responses in animal models of neuropathic pain, formalin-induced pain, and post-operative pain (Chaplan, S. R.; et al. J. Pharmacol. Exp. Ther. 1994, 269(3), 1117-1123. Malmberg, A. B.; et al. J. Neurosci. 1994, 14(8), 4882-4890. Bowersox, S. S.; et al. J. Pharmacol. Exp. Ther. 1996, 279(3), 1243-1249. Wang, Y. X.; et al. Pain 2000, 84(2-3), 151-158. Scott, D. A.; et al. Eur. J. Pharmacol. 2002, 451(3), 279-286.). These peptide blockers bind to the pore region of the channel, do not show voltage- or frequency-dependent activity, and show irreversible channel block (Feng, Z. P.; et al. J. Biol. Chem. 2003, 278(22), 20171-20178.). Ziconotide potently blocks neurotransmitter release in the spinal cord dorsal horn (Matthews, E. A.; et al. Pain 2001, 92(1-2), 235-246. Smith, M. T.; et al. Pain 2002, 96(1-2), 119-127. Heinke, B.; et al. Eur. J. Neurosci. 2004, 19(1), 103-111.) and in dorsal root ganglion (DRG) neurons (Evans, A. R.; et al. Brain Res. 1996, 712(2), 265-273. Smith, M. T.; et al. Pain 2002, 96(1-2), 119-127.). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S. R.; et al. J. Pharmacol. Exp. Ther. 1994, 269(3), 1117-1123.) or thermal hyperalgesia in the chronic constriction injury model (Yamamoto, T.; et al. Brain Res. 1998, 794(2), 329-332.) of neuropathic pain.

T-Type or LVA calcium channels are composed of a single pore forming $\alpha_1$ subunit of which there are three subtypes: Cav3.1, Cav3.2 and Cav3.3 (Perez-Reyes, E.; et al. J Pharmacol Exp Ther. 2009, 328(2), 621-7). These channels are activated at relatively hyperpolarized cell membrane potentials and contribute to membrane depolarization following action potential generation. As a result, T-type calcium channel activation triggers secondary bursts of neuronal action potentials with increased action potential duration. Evidence supporting a role of T-type calcium channels in neuropathic pain comes from studies that have shown a concurrent increase in the expression of Cav3.2 channels after-depolarization potentials in medium diameter Aδ high threshold mechanoreceptor dorsal root ganglia (DRG) neurons in diabetic neuropathy (Jagodic, M. M.; et al. J Neurosci 2007, 27, 3305-3316.) and in small diameter neurons from the chronic constriction injury (CCI) neuropathic pain model (Jagodic, M. M.; et al. J Neurophysiol 2008, 99, 3151-3156.). Additional support comes from gene knockdown studies whereby intrathecal Cav3.2 antisense administration produces a significant knockdown (~80-90%) of T-type calcium currents in small and medium diameter DRG neurons, and produces robust anti-allodynic and antihyperalgesic effects in the CCI rat model of neuropathic pain (Bourinet, E.; et al. Embo J 2005, 24, 315-324). Moreover, Cav3.2 knockout mice show decreased pain responses compared to wild-type mice in acute mechanical, thermal, and chemical pain models (Choi, S.; et al. Genes Brain Behav 2007, 6, 425-431).

Recently, T-type calcium channel blockers have been proposed to have potential in treating schizophrenia and substance dependence. The T-type calcium channels are located in brain regions that have relevance to schizophrenia and substance dependence (Talley, E. M.; et al. J Neurosci 1999, 19, 1895-1911). More importantly, it has been demonstrated that selective T-type calcium channel blockers, such as TTA-A2, have antipsychotic-like effects in preclinical animal models of psychosis (Uslaner, J. M.; et al. Neuropharmacology 2010 (in press)) and were able to decrease nicotine seeking behavior in rats trained to self-administer nicotine (Uslaner, J. M.; et al. Biol Psychiatry 2010, 68, 712-718).

In addition to a role in nociception, T-type calcium channels have also been implicated to play roles in sleep disorders and absence epilepsy (Shin, H.-S.; et al. Curr Opin Pharmacol, 2008, 8, 33-41). Based on expression in the thalamus, T-type calcium channels may play a role in arousal from sleep (Benington, J. H.; et al. Prog Neurobiol 2003, 69, 71-101; Nordskog, B. K.; et al. Neuroscience 2006, 141, 1365-1373). Expression in the adrenal, pituitary and pineal glands suggests that these channels modulate hormone secretion. Notably, Cav3.2 knockout mice appear normal and healthy, although smaller than wild-type mice (Chen, C.-C.; et al. Science 2003, 302, 1416-1418; Choi, S.; et al. Genes Brain Behav 2007, 6, 425-431).

Pain is the most common symptom of disease and the most frequent complaint with which patients present to physicians. Inadequate pain management across the spectrum of pain etiologies remains a major public health problem. Going forward, the development of novel therapeutics with new mechanisms of action for the treatment of pain including calcium channel blockade will have a significant impact on the ongoing struggle to balance efficacy and safety for those patients most in need. The compounds of the present invention are novel calcium channel blockers that have utility in treating pain, amongst other conditions.

SUMMARY OF THE INVENTION

The invention is directed to compounds of formula (I)

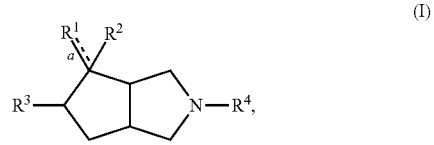

or a pharmaceutically acceptable salt, prodrug, salt of a prodrug, or a combination thereof, wherein
α is a single bond or a double bond;
$R^1$ is O or $CHR^5$ when α is a double bond; or
$R^1$ is alkyl, haloalkyl, hydroxy, $G^1$, —$(CR^aR^b)_m$-$G^2$, —$(CR^aR^b)_m$-$G^3$, —C(O)N($R^x$)—$(CR^aR^b)_m$-$G^2$, —C(O)N($R^x$)—$(CR^aR^b)_m$-$G^3$, —C(O)N($R^x$)$R^u$, —C(O)N($R^x$)$G^2$, —C(O)N($R^x$)$G^3$, —N($R^x$)—$(CR^aR^b)_m$-$G^2$, —N($R^x$)—$(CR^aR^b)_m$-$G^3$, —N($R^x$)C(O)$R^u$, —N($R^x$)C(O)$G^2$, —N($R^x$)C(O)$G^3$, —N($R^x$)C(O)—$(CR^aR^b)_m$-$G^2$, —N($R^x$)C(O)—$(CR^aR^b)_m$-$G^3$, —N($R^x$)C(O)—$(CR^cR^d)_q$—N($R^y$)—C(O)O—$R^v$, —N($R^x$)C(O)—$(CR^cR^d)_q$—N($R^y$)—C(O)$R^w$, —N($R^x$)C(O)—$(CR^cR^d)_q$—N($R^y$)—SO$_2R^w$, —N($R^x$)C(O)—$(CR^cR^d)_q$—N($R^y$)($R^z$), —N($R^x$)C(O)—$(CR^cR^d)_q$—N($R^y$)—C(O)N($R^z$)($R^w$), —N($R^x$)($R^z$), —O—$(CR^aR^b)_m$-$G^2$, —O—$(CR^aR^b)_m$-$G^3$, —O$G^2$, —O$G^3$, or O$R^6$ when a is a single bond;
$R^5$ is hydrogen, alkyl, haloalkyl, —$(CR^aR^b)_m$-$G^3$, or -$G^3$;
$R^6$ is alkyl or haloalkyl;
$R^a$ and $R^b$, at each occurrence, are each independently hydrogen, alkyl, arylalkyl, halogen, haloalkyl, hydroxy, hydroxyalkyl, or $OR^{1a}$; wherein the aryl of arylalkyl is unsubstituted or substituted with 1, 2 3, 4, or 5 substituents independently selected from the group consisting of alkyl, haloalkyl, and halogen;
$R^{1a}$ is alkyl, aryl, arylalkyl, cycloalkyl, cycloalkylalkyl, or haloalkyl; wherein said aryl, the aryl of arylalkyl, cycloalkyl and the cycloalkyl of cycloalkylalkyl are independently unsubstituted or substituted with 1, 2 3, 4, or 5 substituents independently selected from the group consisting of alkyl, haloalkyl, and halogen;

$R^c$ and $R^d$, at each occurrence, are each independently hydrogen, alkyl, aryl, arylalkyl, halogen, haloalkyl, cycloalkylalkyl, heteroaryl, heteroarylalkyl or $OR^{1a}$; wherein the aryl, heteroaryl, the aryl of arylalkyl, the cycloalkyl of cycloalkylalkyl, and the heteroaryl of heteroarylalkyl are each independently unsubstituted or substituted with 1, 2, 3, 4, or 5 substituents independently selected from the group consisting of alkyl, haloalkyl, and halogen;

$R^u$ is alkyl, haloalkyl, or hydroxyalkyl;

$R^v$ is alkyl, arylalkyl, cycloalkyl, cycloalkylalkyl, heteroarylalkyl, or heterocycle; wherein the aryl of arylalkyl, cycloalkyl, cycloalkyl of cycloalkylalkyl, heteroaryl of heteroarylalkyl, and heterocycle are independently unsubstituted or substituted with 1, 2 3, 4, or 5 substituents independently selected from the group consisting of alkyl, haloalkyl, and halogen;

$R^w$ is alkyl, aryl, cycloalkyl, cycloalkenyl, heteroaryl, or heterocycle; wherein said aryl, heteroaryl, and heterocycle are independently unsubstituted or substituted with 1, 2 3, 4, or 5 substituents independently selected from the group consisting of alkyl, haloalkyl, and halogen;

$R^x$ is hydrogen or alkyl;

$R^y$, and $R^z$, at each occurrence, are each independently hydrogen, alkyl, aryl, arylalkyl, cycloalkyl, cycloalkylalkyl, or haloalkyl; wherein said aryl, the aryl of arylalkyl, cycloalkyl, and the cycloalkyl of cycloalkylalkyl are independently unsubstituted or substituted with 1, 2 3, 4, or 5 substituents independently selected from the group consisting of alkyl, haloalkyl, and halogen;

$G^1$ is (i), (ii), (iii), or (iv);

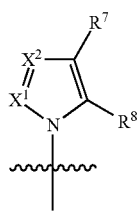

(i)

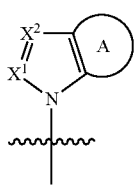

(ii)

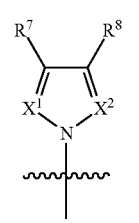

(iii)

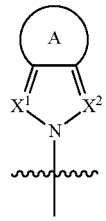

(iv)

$X^1$ and $X^2$ are independently, N or $CR^9$;

$R^9$, at each occurrence, is independently hydrogen, alkyl, alkenyl, alkynyl, halogen, cyano, $-G^3$, $-NO_2$, $-OR^x$, $-OC(O)R^x$, $-OC(O)N(R^x)(R^y)$, $-SR^y$, $-S(O)R^w$, $-S(O)_2R^w$, $-S(O)_2N(R^x)(R^y)$, $-C(O)R^w$, $-C(O)OR^y$, $-C(O)N(R^x)(R^y)$, $-N(R^x)(R^y)$, $-N(R^x)C(O)R^w$, $-N(R^x)C(O)O(R^y)$, $-N(R^x)S(O)_2(R^w)$, cyanoalkyl, or haloalkyl;

A is a fused aryl, cycloalkyl, heterocycle or heteroaryl; wherein A is unsubstituted or substituted with 1, 2, 3, 4, or 5 substituents selected from the group consisting of alkyl, alkenyl, alkynyl, halogen, cyano, $-G^3$, $-NO_2$, $-OR^x$, $-OC(O)R^x$, $-OC(O)N(R^x)(R^y)$, $-SR^y$, $-S(O)R^w$, $-S(O)_2R^w$, $-S(O)_2N(R^x)(R^y)$, $-C(O)R^w$, $-C(O)OR^y$, $-C(O)N(R^x)(R^y)$, $-N(R^x)(R^y)$, $-N(R^x)C(O)R^w$, $-N(R^x)C(O)O(R^y)$, $-N(R^x)S(O)_2(R^w)$, cyanoalkyl, and haloalkyl;

$R^7$ and $R^8$ are independently hydrogen, alkyl, alkenyl, alkynyl, halogen, cyano, $-G^3$, $-NO_2$, $-OR^x$, $-OC(O)R^x$, $-OC(O)N(R^x)(R^y)$, $-SR^y$, $-S(O)R^w$, $-S(O)_2R^w$, $-S(O)_2N(R^x)(R^y)$, $-C(O)R^w$, $-C(O)OR^y$, $-C(O)N(R^x)(R^y)$, $-N(R^x)(R^y)$, $-N(R^x)C(O)R^w$, $-N(R^x)C(O)O(R^y)$, $-N(R^x)S(O)_2(R^w)$, cyanoalkyl, or haloalkyl;

$G^2$, at each occurrence, is independently cycloalkyl, cycloalkenyl, or heterocycle; wherein $G^2$ at each occurrence is each independently unsubstituted or substituted with 1, 2, 3, 4, or 5 substituents selected from the group consisting of alkyl, alkenyl, alkynyl, cyano, haloalkyl, halogen, nitro, oxo, $N(R^{2a})_2$, $N(R^{2a})C(O)R^{2a}$, $OR^{2a}$, $C(O)R^{2a}$, $C(O)OR^{2a}$, $C(O)N(R^{2a})_2$, $SO_2R^{2b}$, and $SO_2N(R^{2a})_2$;

$R^{2a}$ is hydrogen, alkyl, aryl, arylalkyl, cycloalkyl, cycloalkylalkyl, or haloalkyl; wherein said aryl, the aryl of arylalkyl, cycloalkyl, and the cycloalkyl of cycloalkylalkyl are independently unsubstituted or substituted with 1, 2 3, 4, or 5 substituents independently selected from the group consisting of alkyl, haloalkyl, and halogen;

$R^{2b}$ is alkyl or haloalkyl;

$G^3$, at each occurrence, is independently aryl or heteroaryl; wherein $G^3$ at each occurrence is independently unsubstituted or substituted with 1, 2, 3, 4, or 5 substituents selected from the group consisting of alkyl, alkenyl, alkynyl, cyano, haloalkyl, halogen, nitro, $N(R^{2a})_2$, $N(R^{2a})C(O)R^{2a}$, $OR^{2a}$, $C(O)R^{2a}$, $C(O)OR^{2a}$, $C(O)N(R^{2a})_2$, $SO_2R^{2b}$, and $SO_2N(R^{2a})_2$;

m, at each occurrence, is independently 1, 2, 3, 4, 5, or 6;

q, at each occurrence, is independently 1, 2, 3, 4, or 5;

$R^2$ is hydrogen, alkyl, haloalkyl, $G^3$ or $-(CR^aR^b)_m-G^3$ when α is a single bond and $R^1$ is alkyl, haloalkyl, hydroxy, $G^1$, $-C(O)N(R^x)-(CR^aR^b)_m-G^2$, $-C(O)N(R^x)-(CR^aR^b)_m-G^3$, $-C(O)N(R^x)R^u$, $-C(O)N(R^x)G^2$, $-C(O)N(R^x)$ $G^3$, —$(CR^aR^b)_m$-$G^2$, —$(CR^aR^b)_m$-$G^3$, —O—$(CR^aR^b)_m$-$G^2$, —O—$(CR^aR^b)_m$-$G^3$, —$OG^2$, —$OG^3$, or $OR^6$; or $R^2$ is alkyl, haloalkyl, $G^3$ or —$(CR^aR^b)_m$-$G^3$ when α is a single bond and $R^1$ is —$N(R^x)$—$(CR^aR^b)_m$-$G^2$, —$N(R^x)$—$(CR^aR^b)_m$-$G^3$, —$N(R^x)C(O)R^u$, —$N(R^x)C(O)G^2$, —$N(R^x)C(O)G^3$, —$N(R^x)C(O)$—$(CR^aR^b)_m$-$G^2$, —$N(R^x)C(O)$—$(CR^aR^b)_m$-$G^3$, —$N(R^x)C(O)$—$(CR^cR^d)_q$—$N(R^y)$—$C(O)O$—$R^v$, —$N(R^x)C(O)$—$(CR^cR^d)_q$—$N(R^y)$—$C(O)R^w$, —$N(R^x)C(O)$—$(CR^cR^d)_q$—$N(R^y)$—$SO_2R^w$, —$N(R^x)C(O)$—$(CR^cR^d)_q$—$N(R^y)(R^z)$, —$N(R^x)C(O)$—$(CR^cR^d)_q$—$N(R^y)$—$C(O)N(R^w)(R^w)$, —$N(R^x)(R^z)$; or $R^2$ is absent when α is a double bond;

$R^3$ is hydrogen, alkyl, haloalkyl, $G^3$ or —$(CR^aR^b)_m$-$G^3$;

$R^4$ is hydrogen, $G^5$, or —$(CR^aR^b)_m$-$G^3$;

$G^5$ is aryl or heteroaryl; wherein $G^5$ is independently unsubstituted or substituted with 1, 2, 3, 4, or 5 substituents selected from the group consisting of alkyl, alkenyl, alkynyl, cyano, haloalkyl, halogen, nitro, $N(R^{2a})_2$, $N(R^{2a})C(O)R^{2a}$, $OR^{2a}$, $C(O)R^{2a}$, $C(O)OR^{2a}$, $C(O)N(R^{2a})_2$, $SO_2R^{2b}$, and $SO_2N(R^{2a})_2$; and wherein the $G^5$ is other than quinolizinone or quinolone; and provided the compound is other than:

(3aS,6aS)-2-benzyl-4-methyleneoctahydrocyclopenta[c]pyrrole;

(3aR,4R,6aS)-2-benzyloctahydrocyclopenta[c]pyrrol-4-ol; or (3aR,4R,6aS)-octahydrocyclopenta[c]pyrrol-4-ol.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of formula (I), or a pharmaceutically acceptable salt thereof. The disorders of the central nervous system include stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction, or combinations thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

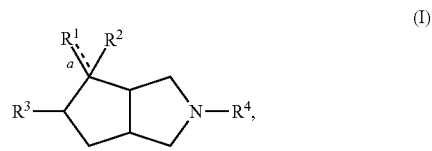

wherein α, $R^1$, $R^2$, $R^3$ and $R^4$ are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group appended to the parent molecular moiety through an alkyl group, as defined herein.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo [3.3.1.1$^{3,7}$]decane), and oxa-adamantane (2-oxatricyclo [3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-α]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means a —NO$_2$ group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "oxo" as used herein, means a =O group.

b. Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In one embodiment, R$^4$ is hydrogen, G$^5$, or —(CR$^a$R$^b$)$_m$-G$^3$.

In another embodiment, R$^4$ is hydrogen.
In another embodiment, R$^4$ is G$^5$.
In another embodiment, R$^4$ is —(CR$^a$R$^b$)$_m$-G$^3$.
In one embodiment, α is a double bond and R$^2$ is absent.
More particularly, compound of formula (I) can include, but are not limited to compounds wherein a is a double bond and R$^2$ is absent, i.e. compounds of formula (Ia),

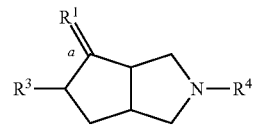

(Ia)

wherein R$^1$ is O or CHR$^5$, and R$^3$ is hydrogen, alkyl, haloalkyl, G$^3$ or —(CR$^a$R$^b$)$_m$-G$^3$.

In one embodiment, compounds of formula (Ia) can include compounds wherein R$^1$ is O, and R$^3$ is hydrogen, alkyl, haloalkyl, G$^3$ or —(CR$^a$R$^b$)$_m$-G$^3$.

In another embodiment, compounds of formula (Ia) can include compounds wherein R$^1$ is O, R$^3$ is hydrogen.

In another embodiment, compounds of formula (Ia) can include compounds wherein R$^1$ is O, R$^3$ is hydrogen, and R$^4$ is hydrogen.

In another embodiment, compounds of formula (Ia) can include compounds wherein R$^1$ is O, R$^3$ is hydrogen, and R$^4$ is G$^5$.

In a further embodiment, compounds of formula (Ia) can include compounds wherein R$^1$ is O, R$^3$ is hydrogen, and R$^4$ is —(CR$^a$R$^b$)$_m$-G$^3$.

In one embodiment, compounds of formula (Ia) can include compounds wherein R$^1$ is O, and R$^3$ is alkyl, haloalkyl, or —(CR$^a$R$^b$)$_m$-G$^3$, and R$^4$ is hydrogen.

In another embodiment, compounds of formula (Ia) can include compounds wherein R$^1$ is O, and R$^3$ is alkyl, haloalkyl, or —(CR$^a$R$^b$)$_m$-G$^3$, and R$^4$ is G$^5$.

In a further embodiment, compounds of formula (Ia) can include compounds wherein R$^1$ is O, and R$^3$ is alkyl, haloalkyl, or —(CR$^a$R$^b$)$_m$-G$^3$, and R$^4$ is —(CR$^a$R$^b$)$_m$-G$^3$.

In one embodiment, compounds of formula (Ia) can include compounds wherein R$^1$ is O, and R$^3$ is G$^3$, and R$^4$ is hydrogen.

In another embodiment, compounds of formula (Ia) can include compounds wherein R$^1$ is O, and R$^3$ is G$^3$, and R$^4$ is G$^5$.

In a further embodiment, compounds of formula (Ia) can include compounds wherein R$^1$ is O, and R$^3$ is G$^3$, and R$^4$ is —(CR$^a$R$^b$)$_m$-G$^3$.

In one embodiment, compounds of formula (Ia) can include compounds wherein R$^1$ is CHR$^5$, wherein R$^5$ is hydrogen, alkyl, haloalkyl, —(CR$^a$R$^b$)$_m$-G$^3$, or -G$^3$, and R$^3$ is hydrogen, alkyl, haloalkyl, G$^3$ or —(CR$^a$R$^b$)$_m$-G$^3$.

In a particular embodiment, compounds of formula (Ia) can include compounds wherein R$^1$ is CHR$^5$, wherein R$^5$ is hydrogen, R$^3$ is hydrogen, and R$^4$ is hydrogen.

In another embodiment, compounds of formula (Ia) can include compounds wherein $R^1$ is $CHR^5$, wherein $R^5$ is hydrogen, $R^3$ is hydrogen, and $R^4$ is $G^5$.

In further embodiment, compounds of formula (Ia) can include compounds wherein $R^1$ is $CHR^5$, wherein $R^5$ is hydrogen, $R^3$ is hydrogen, and $R^4$ is $-(CR^aR^b)_m\text{-}G^3$.

In one embodiment, compounds of formula (Ia) can include compounds wherein $R^1$ is $CHR^5$, wherein $R^5$ is hydrogen, $R^3$ is alkyl, haloalkyl, $G^3$ or $-(CR^aR^b)_m\text{-}G^3$, and $R^4$ is hydrogen.

In another embodiment, compounds of formula (Ia) can include compounds wherein $R^1$ is $CHR^5$, wherein $R^5$ is hydrogen, $R^3$ is alkyl, haloalkyl, $G^3$ or $-(CR^aR^b)_m\text{-}G^3$, and $R^4$ is $G^5$.

In a further embodiment, compounds of formula (Ia) can include compounds wherein $R^1$ is $CHR^5$, wherein $R^5$ is hydrogen, $R^3$ is alkyl, haloalkyl, $G^3$ or $-(CR^aR^b)_m\text{-}G^3$, and $R^4$ is $-(CR^aR^b)_m\text{-}G^3$.

In one embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is hydrogen, and $R^4$ is hydrogen.

In another embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is hydrogen, and $R^4$ is $G^5$.

In a further embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is hydrogen, and $R^4$ is $-(CR^aR^b)_m\text{-}G^3$.

In one embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is alkyl, haloalkyl, $G^3$ or $-(CR^aR^b)_m\text{-}G^3$, and $R^4$ is hydrogen.

In another embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is alkyl, haloalkyl, $G^3$ or $-(CR^aR^b)_m\text{-}G^3$, and $R^4$ is $G^5$.

In a further embodiment, compounds of formula (Ia) can include compounds wherein $R^1$ is $CHR^5$, wherein $R^5$ is alkyl, haloalkyl, $-(CR^aR^b)_m\text{-}G^3$, or $-G^3$, $R^3$ is alkyl, haloalkyl, $G^3$ or $-(CR^aR^b)_m\text{-}G^3$, and $R^4$ is $-(CR^aR^b)_m\text{-}G^3$.

In another particular embodiment, $\alpha$ is a single bond.

In a certain embodiment, compound of formula (I) can include, but are not limited to compounds wherein $\alpha$ is a single bond, i.e. compounds of formula (Ib), (Ib)

[Structure: bicyclic ring with $R^1$, $R^2$ on one carbon (labeled a), $R^3$ on another carbon, and N—$R^4$]

In one embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is hydrogen, and $R^4$ is hydrogen.

In another embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is hydrogen, and $R^4$ is $G^5$.

In a further embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is hydrogen, and $R^4$ is $-(CR^aR^b)_m\text{-}G^3$.

In one embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is hydrogen.

In another embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is $G^5$.

In a further embodiment, compounds of formula (Ib) can include compounds wherein $R^1$ is hydroxy, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is $-(CR^aR^b)_m\text{-}G^3$.

In one embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is hydrogen, and $R^4$ is hydrogen.

In another embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is hydrogen, and $R^4$ is $G^5$.

In a further embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is hydrogen, and $R^4$ is $-(CR^aR^b)_m\text{-}G^3$.

In one embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is hydrogen.

In another embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is $G^5$.

In a further embodiment, compounds of formula (Ib) can include compounds wherein $R^1$ is $-O-(CR^aR^b)_m\text{-}G^2$, $-O-(CR^aR^b)_m\text{-}G^3$, $-OG^2$, $-OG^3$, or $OR^6$, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is $-(CR^aR^b)_m\text{-}G^3$.

In one embodiment, compounds of formula (Ib) can include compounds wherein $R^1$ is $-C(O)N(R^x)-(CR^aR^b)_m\text{-}G^2$, $-C(O)N(R^x)-(CR^aR^b)_m\text{-}G^3$, $-C(O)N(R^x)R^u$, $-C(O)N(R^x)G^2$, or $-C(O)N(R^x)G^3$, $R^2$ is hydrogen, alkyl, haloalkyl, $G^3$ or $-(CR^aR^b)_m\text{-}G^3$, $R^3$ is hydrogen, and $R^4$ is hydrogen.

In another embodiment, compounds of formula (Ib) can include compounds wherein $R^1$ is $-C(O)N(R^x)-(CR^aR^b)_m\text{-}G^2$, $-C(O)N(R^x)-(CR^aR^b)_m\text{-}G^3$, $-C(O)N(R^x)R^u$, $-C(O)N(R^x)G^2$, or $-C(O)N(R^x)G^3$, $R^2$ is hydrogen, alkyl, haloalkyl, $G^3$ or $-(CR^aR^b)_m\text{-}G^3$, $R^3$ is hydrogen, and $R^4$ is $G^5$.

In a further embodiment, compounds of formula (Ib) can include compounds wherein $R^1$ is $-C(O)N(R^x)-(CR^aR^b)_m\text{-}G^2$, $-C(O)N(R^x)-(CR^aR^b)_m\text{-}G^3$, $-C(O)N(R^x)R^u$, $-C(O)N(R^x)G^2$, or $-C(O)N(R^x)G^3$, $R^2$ is hydrogen, alkyl, haloalkyl, $G^3$ or $-(CR^aR^b)_m\text{-}G^3$, $R^3$ is hydrogen, and $R^4$ is $-(CR^aR^b)_m\text{-}G^3$.

In one embodiment, compounds of formula (Ib) can include compounds wherein $R^1$ is $-C(O)N(R^x)-(CR^aR^b)_m\text{-}G^2$, $-C(O)N(R^x)-(CR^aR^b)_m\text{-}G^3$, $-C(O)N(R^x)R^u$, $-C(O)N(R^x)G^2$, or $-C(O)N(R^x)G^3$, $R^2$ is hydrogen, alkyl, haloalkyl, $G^3$ or $-(CR^aR^b)_m\text{-}G^3$, $R^3$ is alkyl, haloalkyl, $G^3$ or $-(CR^aR^b)_m\text{-}G^3$, and $R^4$ is hydrogen.

In another embodiment, compounds of formula (Ib) can include compounds wherein R¹ is —C(O)N(Rˣ)—(CRᵃRᵇ)ₘ-G², —C(O)N(Rˣ)—(CRᵃRᵇ)ₘ-G³, —C(O)N(Rˣ)Rᵘ, —C(O)N(Rˣ)G², or —C(O)N(Rˣ)G³, R² is hydrogen, alkyl, haloalkyl, G³ or —(CRᵃRᵇ)ₘ-G³, R³ is alkyl, haloalkyl, G³ or —(CRᵃRᵇ)ₘ-G³, and R⁴ is G⁵.

In a further embodiment, compounds of formula (Ib) can include compounds wherein R¹ is —C(O)N(Rˣ)—(CRᵃRᵇ)ₘ-G², —C(O)N(Rˣ)—(CRᵃRᵇ)ₘ-G³, —C(O)N(Rˣ)Rᵘ, —C(O)N(Rˣ)G², or —C(O)N(Rˣ)G³, R² is hydrogen, alkyl, haloalkyl, G³ or —(CRᵃRᵇ)ₘ-G³, R³ is alkyl, haloalkyl, G³ or —(CRᵃRᵇ)ₘ-G³, and R⁴ is —(CRᵃRᵇ)ₘ-G³.

In one embodiment, compounds of formula (Ib) can include compounds wherein
R¹ is G¹, wherein G¹ is (i) or (iii), (i)

(iii)

R² is hydrogen, alkyl, haloalkyl, G³ or —(CRᵃRᵇ)ₘ-G³, R³ is hydrogen, and R⁴ is hydrogen.

In another embodiment, compounds of formula (Ib) can include compounds wherein R¹ is G¹, wherein G¹ is (i) or (iii), R² is hydrogen, alkyl, haloalkyl, G³ or —(CRᵃRᵇ)ₘ-G³, R³ is hydrogen, and R⁴ is G⁵.

In another embodiment, compounds of formula (Ib) can include compounds wherein R¹ is G¹, wherein G¹ is (i), wherein X¹ is CR⁹ and X² is N, R² is hydrogen, alkyl, haloalkyl, G³ or —(CRᵃRᵇ)ₘ-G³, R³ is hydrogen, and R⁴ is G⁵.

In another embodiment, compounds of formula (Ib) can include compounds wherein R¹ is G¹, wherein G¹ is (i), wherein X¹ is N and X² is CR⁹, R² is hydrogen, alkyl, haloalkyl, G³ or —(CRᵃRᵇ)ₘ-G³, R³ is hydrogen, and R⁴ is G⁵.

In a further embodiment, compounds of formula (Ib) can include compounds wherein R¹ is G¹, wherein G¹ is (i) or (iii), R² is hydrogen, alkyl, haloalkyl, G³ or —(CRᵃRᵇ)ₘ-G³, R³ is hydrogen, and R⁴ is —(CRᵃRᵇ)ₘ-G³.

In one embodiment, compounds of formula (Ib) can include compounds wherein R¹ is G¹, wherein G¹ is (i) or (iii), (i)

(iii)

R² is hydrogen, alkyl, haloalkyl, G³ or —(CRᵃRᵇ)ₘ-G³, R³ is alkyl, haloalkyl, G³ or —(CRᵃRᵇ)ₘ-G³, and R⁴ is hydrogen.

In another embodiment, compounds of formula (Ib) can include compounds wherein R¹ is G¹, wherein G¹ is (i) or (iii), R² is hydrogen, alkyl, haloalkyl, G³ or —(CRᵃRᵇ)ₘ-G³, R³ is alkyl, haloalkyl, G³ or —(CRᵃRᵇ)ₘ-G³, and R⁴ is G⁵.

In a further embodiment, compounds of formula (Ib) can include compounds wherein R¹ is G¹, wherein G¹ is (i) or (iii), R² is hydrogen, alkyl, haloalkyl, G³ or —(CRᵃRᵇ)ₘ-G³, R³ is alkyl, haloalkyl, G³ or —(CRᵃRᵇ)ₘ-G³, and R⁴ is —(CRᵃRᵇ)ₘ-G³.

In one embodiment, compounds of formula (Ib) can include compounds wherein R¹ is G¹, wherein G¹ is (ii) or (iv), (ii)

(iv)

R² is hydrogen, alkyl, haloalkyl, G³ or —(CRᵃRᵇ)ₘ-G³, R³ is hydrogen, and R⁴ is hydrogen.

In another embodiment, compounds of formula (Ib) can include compounds wherein R¹ is G¹, wherein G¹ is (ii) or (iv), R² is hydrogen, alkyl, haloalkyl, G³ or —(CRᵃRᵇ)ₘ-G³, R³ is hydrogen, and R⁴ is G⁵.

In another embodiment, compounds of formula (Ib) can include compounds wherein R¹ is G¹, wherein G¹ is (ii), wherein X¹ is CR⁹ and X² is N and A is an optionally substituted fused aryl, R² is hydrogen, alkyl, haloalkyl, G³ or —(CRᵃRᵇ)ₘ-G³, R³ is hydrogen, and R⁴ is G⁵.

In another embodiment, compounds of formula (Ib) can include compounds wherein R¹ is G¹, wherein G¹ is (ii), wherein X¹ is N and X² is CR⁹ and A is an optionally substituted fused aryl, R² is hydrogen, alkyl, haloalkyl, G³ or —(CRᵃRᵇ)ₘ-G³, R³ is hydrogen, and R⁴ is G⁵.

In a further embodiment, compounds of formula (Ib) can include compounds wherein R¹ is G¹, wherein G¹ is (ii) or (iv), R² is hydrogen, alkyl, haloalkyl, G³ or —(CRᵃRᵇ)ₘ-G³, R³ is hydrogen, and R⁴ is —(CRᵃRᵇ)ₘ-G³.

In one embodiment, compounds of formula (Ib) can include compounds wherein R¹ is G¹, wherein G¹ is (ii) or (iv), (ii)

[Structure showing ring A with X², X¹, N attached]

(iv)

[Structure showing ring A with X¹, X², N attached]

$R^2$ is hydrogen, alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is hydrogen.

In another embodiment, compounds of formula (Ib) can include compounds wherein $R^1$ is $G^1$, wherein $G^1$ is (ii) or (iv), $R^2$ is hydrogen, alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is $G^5$.

In a further embodiment, compounds of formula (Ib) can include compounds wherein $R^1$ is $G^1$, wherein $G^1$ is (ii) or (iv), $R^2$ is hydrogen, alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is —$(CR^aR^b)_m$-$G^3$.

In one embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ alkyl, haloalkyl, $G^3$ or —$(CR^aR^b)_m$-$G^3$, $R^3$ is hydrogen, and $R^4$ is hydrogen.

In another embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ is alkyl, haloalkyl, $G^3$ or —$(CR^aR^b)_m$-$G^3$, $R^3$ is hydrogen, and $R^4$ is $G^5$.

In a further embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ is alkyl, haloalkyl, $G^3$ or —$(CR^aR^b)_m$-$G^3$, $R^3$ is hydrogen, and $R^4$ is —$(CR^aR^b)_m$-$G^3$.

In one embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is hydrogen.

In another embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is $G^5$.

In a further embodiment, compounds of formula (Ib) can include compounds wherein $R^1$ is —$N(R^x)$—$(CR^aR^b)_m$-$G^2$ or —$N(R^x)$—$(CR^aR^b)_m$-$G^3$, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is —$(CR^aR^b)_m$-$G^3$.

In one embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is hydrogen, and $R^4$ is hydrogen.

In another embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is hydrogen, and $R^4$ is $G^5$.

In a further embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is hydrogen, and $R^4$ is —$(CR^aR^b)_m$-$G^3$.

In one embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is hydrogen.

In another embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is $G^5$.

In a further embodiment, compounds of formula (Ib) can include compounds wherein $R^1$ is —$N(R^x)(R^z)$ wherein $R^x$ is hydrogen and $R^z$ alkyl, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is —$(CR^aR^b)_m$-$G^3$.

In one embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is hydrogen, and $R^4$ is hydrogen.

In another embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is hydrogen, and $R^4$ is $G^5$.

In a further embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is hydrogen, and $R^4$ is —$(CR^aR^b)_m$-$G^3$.

In one embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is hydrogen.

In another embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is $G^5$.

In a further embodiment, compounds of formula (Ib) can include compounds wherein $R^1$ is —$N(R^x)(R^z)$ wherein $R^x$ and $R^z$ are both hydrogen, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is —$(CR^aR^b)_m$-$G^3$.

In one embodiment, compounds of formula (Ib) can include compounds wherein $R^1$ is —$N(R^x)C(O)R^u$, —$N(R^x)C(O)G^2$, —$N(R^x)C(O)G^3$, —$N(R^x)C(O)$—$(CR^aR^b)_m$-$G^2$, or —$N(R^x)C(O)$—$(CR^aR^b)_m$-$G^3$, $R^2$ is alkyl, haloalkyl, $G^3$ or —$(CR^aR^b)_m$-$G^3$, $R^3$ is hydrogen, and $R^4$ is hydrogen.

In another embodiment, compounds of formula (Ib) can include compounds wherein $R^1$ is —$N(R^x)C(O)R^u$, —$N(R^x)C(O)G^2$, —$N(R^x)C(O)G^3$, —$N(R^x)C(O)$—$(CR^aR^b)_m$-$G^2$, or —$N(R^x)C(O)$—$(CR^aR^b)_m$-$G^3$, $R^2$ is alkyl, haloalkyl, $G^3$ or —$(CR^aR^b)_m$-$G^3$, $R^3$ is hydrogen, and $R^4$ is $G^5$.

In a further embodiment, compounds of formula (Ib) can include compounds wherein $R^1$ is —$N(R^x)C(O)R^u$, —$N(R^x)C(O)G^2$, —$N(R^x)C(O)G^3$, —$N(R^x)C(O)$—$(CR^aR^b)_m$-$G^2$, or —$N(R^x)C(O)$—$(CR^aR^b)_m$-$G^3$, $R^2$ is alkyl, haloalkyl, $G^3$ or —$(CR^aR^b)_m$-$G^3$, $R^3$ is hydrogen, and $R^4$ is —$(CR^aR^b)_m$-$G^3$.

In one embodiment, compounds of formula (Ib) can include compounds wherein $R^1$ is —$N(R^x)C(O)R^u$, —$N(R^x)C(O)G^2$, —$N(R^x)C(O)G^3$, —$N(R^x)C(O)$—$(CR^aR^b)_m$-$G^2$, or —$N(R^x)C(O)$—$(CR^aR^b)_m$-$G^3$, $R^2$ is alkyl, haloalkyl, $G^3$ or —$(CR^aR^b)_m$-$G^3$, $R^3$ is alkyl, haloalkyl, $G^3$ or —$(CR^aR^b)_m$-$G^3$, and $R^4$ is hydrogen.

In another embodiment, compounds of formula (Ib) can include compounds wherein $R^1$ is —$N(R^x)C(O)R^u$, —$N(R^x)$ C(O)G², —N(Rˣ)C(O)G³, —N(Rˣ)C(O)—(CRᵃRᵇ)ₘ-G², or —N(Rˣ)C(O)—(CRᵃRᵇ)ₘ-G³, R² is alkyl, haloalkyl, G³ or —(CRᵃRᵇ)ₘ-G³, R³ is alkyl, haloalkyl, G³ or —(CRᵃRᵇ)ₘ-G³, and R⁴ is G⁵.

In a further embodiment, compounds of formula (Ib) can include compounds wherein R¹ is —N(Rˣ)C(O)Rᵘ, —N(Rˣ)C(O)G², —N(Rˣ)C(O)G³, —N(Rˣ)C(O)—(CRᵃRᵇ)ₘ-G², or —N(Rˣ)C(O)—(CRᵃRᵇ)ₘ-G³, R² is alkyl, haloalkyl, G³ or —(CRᵃRᵇ)ₘ-G³, R³ is alkyl, haloalkyl, G³ or —(CRᵃRᵇ)ₘ-G³, and R⁴ is —(CRᵃRᵇ)ₘ-G³.

In one embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is hydrogen, and R⁴ is hydrogen.

In another embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is hydrogen, and R⁴ is G⁵.

In a further embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is hydrogen, and R⁴ is —(CRᵃRᵇ)ₘ-G³.

In one embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is alkyl, haloalkyl, G³ or —(CRᵃRᵇ)ₘ-G³, and R⁴ is hydrogen.

In another embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is alkyl, haloalkyl, G³ or —(CRᵃRᵇ)ₘ-G³, and R⁴ is G⁵.

In a further embodiment, compounds of formula (Ib) can include compounds wherein R¹ is —N(Rˣ)C(O)—(CRᶜRᵈ)_q—N(Rʸ)—C(O)O—Rᵛ, —N(Rˣ)C(O)—(CRᶜRᵈ)_q—N(Rʸ)—C(O)Rʷ, —N(Rˣ)C(O)—(CRᶜRᵈ)_q—N(Rʸ)—SO₂Rʷ, —N(Rˣ)C(O)—(CRᶜRᵈ)_q—N(Rʸ)(Rᶻ), or —N(Rˣ)C(O)—(CRᶜRᵈ)_q—N(Rʸ)—C(O)N(Rʸ)(Rʷ), R² is alkyl, haloalkyl, G³ or —(CRᵃRᵇ)ₘ-G³, R³ is alkyl, haloalkyl, G³ or —(CRᵃRᵇ)ₘ-G³, and R⁴ is —(CRᵃRᵇ)ₘ-G³.

Specific embodiments of compounds contemplated as part of the invention include, but are not limited to:

N-[(3aR,4R,6aS)-2-benzyl-4-methyloctahydrocyclopenta[c]pyrrol-4-yl]benzamide;
N-[(3aR,4S,6aS)-2-benzyl-4-methyloctahydrocyclopenta[c]pyrrol-4-yl]benzamide;
N-[(3aR,4R,6aS)-2-benzyl-4-methyloctahydrocyclopenta[c]pyrrol-4-yl]acetamide;
N-[(3aR,4S,6aS)-2-benzyl-4-methyloctahydrocyclopenta[c]pyrrol-4-yl]acetamide;
N-[(3aR,4R,6aS)-2-benzyl-4-methyloctahydrocyclopenta[c]pyrrol-4-yl]-3-fluorobenzamide;
N-[(3aR,4S,6aS)-2-benzyl-4-methyloctahydrocyclopenta[c]pyrrol-4-yl]-3-fluorobenzamide;
N-[(3aR,4R,6aS)-4-methyloctahydrocyclopenta[c]pyrrol-4-yl]benzamide;
N-[(3aR,4S,6aS)-4-methyloctahydrocyclopenta[c]pyrrol-4-yl]benzamide;
N-[(3aR,4R,6aS)-4-methyloctahydrocyclopenta[c]pyrrol-4-yl]acetamide;
N-[(3aR,4S,6aS)-4-methyloctahydrocyclopenta[c]pyrrol-4-yl]acetamide;
3-fluoro-N-[(3aR,4R,6aS)-4-methyloctahydrocyclopenta[c]pyrrol-4-yl]benzamide;
3-fluoro-N-[(3aR,4S,6aS)-4-methyloctahydrocyclopenta[c]pyrrol-4-yl]benzamide;
N-{(3aR,4R,6aS)-4-methyl-2-[6-(trifluoromethyl)pyridin-2-yl]octahydrocyclopenta[c]pyrrol-4-yl}benzamide;
N-{(3aR,4S,6aS)-4-methyl-2-[6-(trifluoromethyl)pyridin-2-yl]octahydrocyclopenta[c]pyrrol-4-yl}benzamide;
N-{(3aR,4R,6aS)-4-methyl-2-[6-(trifluoromethyl)pyridin-2-yl]octahydrocyclopenta[c]pyrrol-4-yl}acetamide;
N-{(3aR,4S,6aS)-4-methyl-2-[6-(trifluoromethyl)pyridin-2-yl]octahydrocyclopenta[c]pyrrol-4-yl}acetamide;
3-fluoro-N-{(3aR,4R,6aS)-4-methyl-2-[6-(trifluoromethyl)pyridin-2-yl]octahydrocyclopenta[c]pyrrol-4-yl}benzamide;
3-fluoro-N-{(3aR,4S,6aS)-4-methyl-2-[6-(trifluoromethyl)pyridin-2-yl]octahydrocyclopenta[c]pyrrol-4-yl}benzamide;
(3aR,4S,6aS)—N-benzyl-4-methyl-2-[6-(trifluoromethyl)pyridin-2-yl]octahydrocyclopenta[c]pyrrol-4-amine;
(3aR,4R,6aS)—N-benzyl-4-methyl-2-[6-(trifluoromethyl)pyridin-2-yl]octahydrocyclopenta[c]pyrrol-4-amine;
(3aR,4R,6aS)—N-ethyl-4-methyl-2-[6-(trifluoromethyl)pyridin-2-yl]octahydrocyclopenta[c]pyrrol-4-amine;
(3aR,4S,6aS)—N-ethyl-4-methyl-2-[6-(trifluoromethyl)pyridin-2-yl]octahydrocyclopenta[c]pyrrol-4-amine;
(3aR,4R,6aS)—N-(3-fluorobenzyl)-4-methyl-2-[6-(trifluoromethyl)pyridin-2-yl]octahydrocyclopenta[c]pyrrol-4-amine;
(3aR,4S,6aS)—N-(3-fluorobenzyl)-4-methyl-2-[6-(trifluoromethyl)pyridin-2-yl]octahydrocyclopenta[c]pyrrol-4-amine;
(3aR,4R,6aS)-4-methyl-2-[6-(trifluoromethyl)pyridin-2-yl]octahydrocyclopenta[c]pyrrol-4-amine;
(3aR,4S,6aS)-4-methyl-2-[6-(trifluoromethyl)pyridin-2-yl]octahydrocyclopenta[c]pyrrol-4-amine;
(3aR,4R,6aS)-2-[6-(trifluoromethyl)pyridin-2-yl]octahydrocyclopenta[c]pyrrol-4-ol;
(3aR,4S,6aS)-2-[6-(trifluoromethyl)pyridin-2-yl]octahydrocyclopenta[c]pyrrol-4-ol;
(3aR,6aS)-2-[6-(trifluoromethyl)pyridin-2-yl]hexahydrocyclopenta[c]pyrrol-4(1H)-one;
(3aR,4R,6aS)-4-methyl-2-[6-(trifluoromethyl)pyridin-2-yl]octahydrocyclopenta[c]pyrrol-4-ol;
(3aR,4S,6aS)-4-isopropyl-2-[6-(trifluoromethyl)pyridin-2-yl]octahydrocyclopenta[c]pyrrol-4-ol;
(3aR,4R,6aS)-4-phenyl-2-[6-(trifluoromethyl)pyridin-2-yl]octahydrocyclopenta[c]pyrrol-4-ol;
(3aR,4R,6aS)-4-(3-fluorophenyl)-2-[6-(trifluoromethyl)pyridin-2-yl]octahydrocyclopenta[c]pyrrol-4-ol;
(3aR,4S,6aS)-4-(3,4-difluorobenzyl)-2-[6-(trifluoromethyl)pyridin-2-yl]octahydrocyclopenta[c]pyrrol-4-ol;

(3aR,4S,6aS)-4-[2-(3-fluorophenyl)ethyl]-2-[6-(trifluoromethyl)pyridin-2-yl]octahydrocyclopenta[c]pyrrol-4-ol;

(3aR,4S,6aS)-4-methoxy-2-[6-(trifluoromethyl)pyridin-2-yl]octahydrocyclopenta[c]pyrrole;

(3aR,4S,6aS)-4-ethoxy-2-[6-(trifluoromethyl)pyridin-2-yl]octahydrocyclopenta[c]pyrrole;

(3aR,4S,6aS)-4-isopropoxy-2-[6-(trifluoromethyl)pyridin-2-yl]octahydrocyclopenta[c]pyrrole;

(3aR,4S,6aS)-4-tert-butoxy-2-[6-(trifluoromethyl)pyridin-2-yl]octahydrocyclopenta[c]pyrrole;

(3aR,4S,6aS)-4-(3-fluorophenoxy)-2-[6-(trifluoromethyl)pyridin-2-yl]octahydrocyclopenta[c]pyrrole;

(3aR,4S,6aS)-4-[(3-fluorobenzyl)oxy]-2-[6-(trifluoromethyl)pyridin-2-yl]octahydrocyclopenta[c]pyrrole;

(3aR,4S,6aS)-4-[2-(3-fluorophenyl)ethoxy]-2-[6-(trifluoromethyl)pyridin-2-yl]octahydrocyclopenta[c]pyrrole;

(3aR,4R,6aS)-2-benzyl-4-phenyloctahydrocyclopenta[c]pyrrol-4-ol;

(3aR,4S,6aS)-2-benzyl-4-(3-fluorophenoxy)octahydrocyclopenta[c]pyrrole;

(3aS,6aS)-4-methylene-2-[6-(trifluoromethyl)pyridin-2-yl]octahydrocyclopenta[c]pyrrole;

(3aR,4S,6aS)-4-(1H-imidazol-1-yl)-2-[6-(trifluoromethyl)pyridin-2-yl]octahydrocyclopenta[c]pyrrole;

(3aR,4S,6aS)-4-(1H-pyrazol-1-yl)-2-[6-(trifluoromethyl)pyridin-2-yl]octahydrocyclopenta[c]pyrrole;

(3aR,4S,6aS)-4-(4-chloro-1H-pyrazol-1-yl)-2-[6-(trifluoromethyl)pyridin-2-yl]octahydrocyclopenta[c]pyrrole;

(3aR,4S,6aS)-4-[(2S)-pyrrolidin-2-ylmethoxy]-2-[6-(trifluoromethyl)pyridin-2-yl]octahydrocyclopenta[c]pyrrole;

(3aS,4S,6aS)—N-(3-fluorophenyl)octahydrocyclopenta[c]pyrrole-4-carboxamide;

(3aS,4S,6aS)—N-(3-fluorophenyl)-2-[6-(trifluoromethyl)pyridin-2-yl]octahydrocyclopenta[c]pyrrole-4-carboxamide;

(3aR,4S,6aS)-4-[4-(4-chlorophenyl)-1H-imidazol-1-yl]-2-[6-(trifluoromethyl)pyridin-2-yl]octahydrocyclopenta[c]pyrrole;

(3aR,4S,6aS)-4-(4-phenyl-1H-imidazol-1-yl)-2-[6-(trifluoromethyl)pyridin-2-yl]octahydrocyclopenta[c]pyrrole;

5-methyl-1-{(3aR,4S,6aS)-2-[6-(trifluoromethyl)pyridin-2-yl]octahydrocyclopenta[c]pyrrol-4-yl}-1H-benzimidazole and 6-methyl-1-{(3aR,4S,6aS)-2-[6-(trifluoromethyl)pyridin-2-yl]octahydrocyclopenta[c]pyrrol-4-yl}-1H-benzimidazole;

1-{(3aR,4S,6aS)-2-[6-(trifluoromethyl)pyridin-2-yl]octahydrocyclopenta[c]pyrrol-4-yl}-1H-benzimidazole;

(3aR,4S,6aS)-4-(2-methyl-1H-imidazol-1-yl)-2-[6-(trifluoromethyl)pyridin-2-yl]octahydrocyclopenta[c]pyrrole;

(3aR,4S,6aS)-4-(2-phenyl-1H-imidazol-1-yl)-2-[6-(trifluoromethyl)pyridin-2-yl]octahydrocyclopenta[c]pyrrole;

(3aR,4S,6aS)-4-(4-methyl-1H-pyrazol-1-yl)-2-[6-(trifluoromethyl)pyridin-2-yl]octahydrocyclopenta[c]pyrrole;

7-fluoro-1-{(3aR,4S,6aS)-2-[6-(trifluoromethyl)pyridin-2-yl]octahydrocyclopenta[c]pyrrol-4-yl}-1H-benzimidazole;

1-{(3aR,4S,6aS)-2-[6-(trifluoromethyl)pyridin-2-yl]octahydrocyclopenta[c]pyrrol-4-yl}-1H-indazole;

(3aR,4S,6aS)-4-(3-methyl-1H-pyrazol-1-yl)-2-[6-(trifluoromethyl)pyridin-2-yl]octahydrocyclopenta[c]pyrrole;

(3aR,4S,6aS)-4-(4-methyl-1H-imidazol-1-yl)-2-[6-(trifluoromethyl)pyridin-2-yl]octahydrocyclopenta[c]pyrrole;

(3aR,4S,5R,6aS)-5-(1H-imidazol-1-yl)-2-[6-(trifluoromethyl)pyridin-2-yl]octahydrocyclopenta[c]pyrrol-4-ol;

(3aR,4S,5S,6aS)-5-(1H-imidazol-1-yl)-2-[6-(trifluoromethyl)pyridin-2-yl]octahydrocyclopenta[c]pyrrol-4-ol;

(4R)-4-fluoro-N-{(3aR,4S,6aS)-4-methyl-2-[6-(trifluoromethyl)pyridin-2-yl]octahydrocyclopenta[c]pyrrol-4-yl}-L-prolinamide;

$N^2$-methyl-N-{(3aR,4S,6aS)-4-methyl-2-[6-(trifluoromethyl)pyridin-2-yl]octahydrocyclopenta[c]pyrrol-4-yl}-L-leucinamide; and 4,4,4-trifluoro-N-{(3aR,4S,6aS)-4-methyl-2-[6-(trifluoromethyl)pyridin-2-yl]octahydrocyclopenta[c]pyrrol-4-yl}butanamide.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in Formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET)

studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

c. Biological Data

Abbreviations which have been used in the descriptions of Biological Data that follow are: EDTA for ethylenediaminetetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; p.o. for per orem (by mouth).

(i) In Vitro Methods—Assessment of Calcium Channel Activity Using FLIPR:

IMR32 cells endogenously expressing human $Ca_v2.2$ were assayed for $Ca^{2+}$ influx using a no-wash calcium indicator dye (Calcium 4 dye: Molecular Probes) and FLIPR technology (Lubin, M. L.; Reitz, T. L.; Todd, M. J.; Flores, C. M.; Qin, N.; Xin, H. Assay and Drug Development Technologies 2006, 4(6), 689-694.). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cell-bind) at a density of $1-1.2\times10^5$ cells/well and incubated in the maintenance media above for 48 hours at 37° C. Immediately prior to performing the assay the media was removed and cells were loaded for 1.5 hours with 1×Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 60 minute pre-incubation with compounds (full log dilutions from 10 µM to 0.1 nM) in the presence of 1.3 mM $CaCl_2$ and 2 µM nifedipine to block endogenous L-type channels, the external $Ca^{2+}$ concentration was increased to 5 mM $CaCl_2$ and the cells concomitantly depolarized with 80 mM KCl to assay channel activity. To determine the $IC_{50}$ values, the percent inhibition of the compound at each concentration was determined relative to the activity in the absence of inhibitor, and data was fitted using non-linear regression sigmoidal dose response curve analysis with GraphPad Prism®.

| Example | $IC_{50}$ (µM) |
|---|---|
| 1 | >30 |
| 2 | 11.5 |
| 3 | 12 |
| 4 | >30 |
| 5 | >30 |
| 6 | 17.68 |
| 7 | 5.16 |
| 8 | 26.3 |
| 9 | >30 |
| 14 | 2.14 |
| 15 | 2.52 |
| 16 | 6.44 |
| 17 | 3.27 |
| 18 | 1.50 |
| 19 | 1.82 |
| 20 | 0.38 |
| 21 | 1.03 |
| 22 | 5.85 |
| 23 | 1.76 |
| 24 | 0.33 |
| 25 | 0.18 |
| 26 | 3.64 |
| 27 | 1.80 |
| 30 | 15.78 |
| 31 | 9.62 |
| 32 | 21.37 |
| 33 | 8.34 |
| 34 | 3.05 |
| 35 | 2.87 |
| 36 | 6.13 |
| 37 | 3.72 |
| 38 | 6.10 |
| 40 | 3.37 |
| 41 | 3.32 |
| 42 | 3.82 |
| 43 | 2.54 |
| 44 | 6.01 |
| 45 | 8.05 |
| 46 | 8.41 |
| 47 | 8.83 |
| 48 | 2.95 |
| 49 | 24.88 |
| 50 | 4.30 |
| 51 | 1.39 |
| 52 | 7.39 |
| 53 | 0.66 |
| 54 | 11.63 |
| 55 | >30 |
| 56 | 8.90 |
| 57 | 5.79 |
| 58 | 3.15 |
| 59 | 2.80 |
| 60 | 1.96 |
| 61 | 3.57 |
| 62 | 1.03 |
| 63 | 2.78 |
| 64 | 3.60 |
| 65 | 4.85 |
| 66 | 5.74 |
| 67 | 4.33 |
| 68 | 10.80 |
| 69 | 9.15 |
| 70 | 3.09 |
| 71 | 0.78 |
| 72 | 1.15 | d. Methods of Using the Compounds

One embodiment of the present invention provides a method of treating pain in a subject in need thereof. The method comprises administering to the subject, including a mammal, such as a human, a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazapine, histamine antagonist, sedative, skeletal muscle relaxant, transient receptor potential ion channel antagonist, α-adrenergic, tricyclic antidepressant, anticonvulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, 5-HT$_{2A}$ receptor antagonist, cholinergic analgesic, α$_2$δ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin E$_2$ subtype 4 antagonist, leukotriene B4 antagonist, 5-lipoxygenase inhibitor, sodium channel blocker, 5-HT3 antagonist, N-methyl-D-aspartic acid receptor antagonist, and phosphodiesterase V inhibitor.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F.; et al. American Journal of Hypertension 2004, 17(9), 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F. C.; et al. Stroke 1995, 26, 1683-1690.). In another model of global ischemia, a calcium channel blocker offered neuroprotection although not permanently (Colbourne, F.; et al. Stroke 1999, 30(3), 662-668.). Additionally, diminished progression of carotid atherosclerosis has been observed with calcium channel blocker use (Zanchetti, A.; et al. Circulation 2002, 106, r47-r52.).

An increase in intracellular calcium concentration has been correlated with seizure activity (Heinemann, U.; et al. Exp. Brain Res. 1977, 27, 237-243.). Several studies have indicated that calcium channel blockers produce anticonvulsant activity (Vezzani, A.; et al. Neuropharmacology 1988, 27(5), 451-458. Otoom, S.; et al. Fundamental & Clinical Pharmacology 2006, 20, 115-119.).

Calcium channel blockers have been evaluated in the treatment of bipolar disorders and manic depression for decades. There are suggestions that the calcium channel subtype has influence on efficacy of these disorders (Gitlin, M. Molecular Psychiatry 2006, 11, 227-240. Levy, N. A.; Janicak, P. G. Bipolar Disorders 2000, 2, 108-119.).

Calcium channel blockers have also been associated with the treatment of anxiety and depression (Saade, S.; et al. Pharmacology, Biochemistry and Behavior 2003, 74, 269-278.).

Antischizophrenic drugs have been found to be calcium channel antagonists (Gould, R. J.; et al. Proc. Natl. Acad. Sci. USA 1983, 80, 5122-5125.). Other calcium channel blockers have been suggested for the treatment of schizophrenia (Tort, A. B. L.; et al. Psychopharmacology 2005, 177, 344-348.). T-type calcium channels have been located in brain regions with relevance to schizophrenia and substance dependence (Talley, E. M.; et al. J Neurosci 1999, 19, 1895-1911).

Migraines are treated with calcium channel blockers (Arulmoshi, D. K.; et al. Vascular Pharmacology 2005, 43, 176-187. Gladstone, J. P.; et al. Expert Rev. Neurotherapeutics 2003, 3(6), 845-872.).

Disorders of the lower urinary tract including overactive bladder, prostatis, prostadynia, interstitial cystitis, and benign prostatic hyperplasia can be treated with calcium channel blockers (Fraser, M. O.; et al. US20050148587, 2005).

Ethanol withdrawal syndrome is decreased with calcium channel blockers (Little, H. J.; et al. Life Sciences 1986, 39, 2059-2065.).

Dependence on nicotine has been decreased upon treatment with T-type calcium channel blockers (Uslaner, J. M.; et al. Neuropharmacology 2010 (in press)).

Several cardiac disorders are treated with calcium channel blockers. Atherosclerosis may be reduced by a decrease in free radical-mediated damage as a result of influence on the biophysical properties of membranes (Mason, R. P.; et al. Biochemical Pharmacology 1998, 55, 1843-1852.). Hypertension and angina are both successfully treated with calcium channel blockers (Croom, K. F.; et al. Drugs 2006, 66(4), 497-528.).

There is data suggesting that calcium channel blockers inhibit the proliferation of cancer cells (Gray, L. S.; et al. International Publication No. WO200059882, 2000.).

Calcium channels have been suggested as a target for the treatment of diabetes (Bhattacharjee, A.; et al. Endocrinology 1997, 138(9), 3735-3740.).

Ion channels including calcium channels play an important role in sperm physiology and fertilization (Darszon, A.; et al. Physiological Reviews 1999, 79(2), 481-510).

Calcium channel blockers modulate inflammation (Bilici, D.; et al. Pharmacological Research 2001, 44(6), 527-531.).

Increased calcium levels in neurones has been implicated in Alzheimer's disease. Two suggested mechanisms of increased calcium influx are that β-amyloid may form calcium permeable channels (Bhatia, R.; et al. FASEB J. 2000, 14(9), 1233-1243.) or a G-protein-coupled receptor may be activated by β-amyloid (Lorton, D. Mech. Ageing Dev. 1997, 94(1-3), 199-211.).

Neurodegenerative diseases, including Parkinson's and Alzheimer's diseases can be modulated by calcium channel blockers (Rodnitzky, R. L. Drugs 1999, 57(6), 845-849. Vagnucci, A. H., Jr.; et al. The Lancet 2003, 361(9357), 605-608. Veng, L. M.; et al. Molecular Brain Research 2203, 110, 193-202. Geldenhuys, W. J.; et al. Bioorganic and Medicinal Chemistry 2007, 15, 1525-1532. Cavalli, A.; et al. J. Med. Chem. 2008, 51(3), 347-372.).

Sleep disorders and absence epilepsy have been associated with calcium channels (Shin, H.-S.; et al. Curr Opin Pharmacol, 2008, 8, 33-41).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-$HT_{2A}$ receptor antagonists, cholinergic analgesics, $α_2δ$ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R^1$, $R^2$, $R^3$, $R^4$, $R^7$, $R^8$, $R^a$, $R^b$, $R^c$ $R^d$, $R^u$, $R^v$, $R^w$, $R^x$, $R^y$, $R^z$, $G^1$, $G^2$, $G^3$, $G^5$, $X^1$, $X^2$, m and q, have the meanings as set forth in the Summary of the Invention section unless otherwise noted, can be synthesized as shown in Schemes 1-9.

Abbreviations which have been used in the descriptions of the Schemes and the Examples that follow are: Ac for acetyl; Bn for benzyl; HOAc for acetic acid; OAc for acetate; Ph for phenyl; and $PPh_3$ for triphenylphosphine.

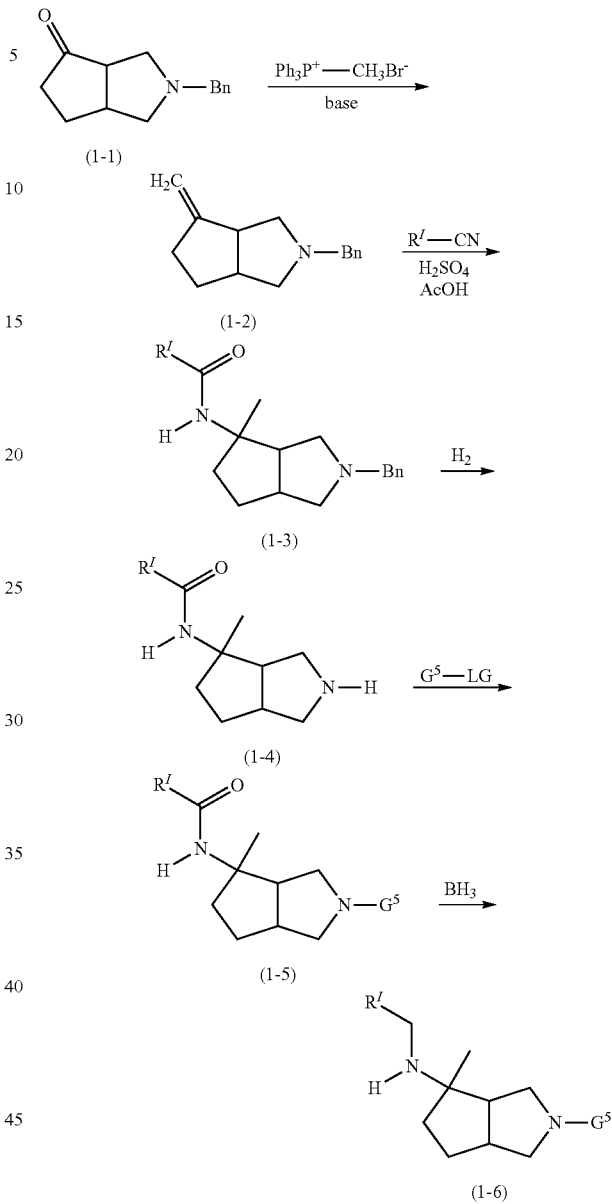

Scheme 1

Compounds of formulas (1-3), (1-4), (1-5), and (1-6), wherein $R^I$ is optionally substituted aryl, optionally substituted heteroaryl or alkyl and $G^5$ is as described in the Summary of the Invention, can be prepared as illustrated in Scheme 1. Compounds of formula (1-1) can be reacted with methyltriphenylphosphonium bromide in the presence of a base such as potassium tert-butoxide in a solvent such as tetrahydrofuran to give compounds of formula (1-2). Compounds of formula (1-2) can be reacted with $R^I$—CN under Ritter reaction conditions to give compounds of formula (1-3). The benzyl group of compounds of formula (1-3) can be removed by hydrogenolysis in the presence of an appropriate catalyst to give compounds of formula (1-4). Compounds of formula (1-4) can be coupled with $G^5$-LG, wherein LG is a leaving group such as iodine, bromine or chlorine, under cross-coupling conditions known to one skilled in the art to give compounds of formula (1-5). Alternatively, when $G^5$-LG represents a pyridyl halide or pyrimidinyl halide, heating in a solvent such as ethanol in the presence of a base such as triethylamine converts compounds of formula (1-4) to compounds of formula (1-5). The reaction is enhanced when the pyridyl halide or pyrimidinyl halide are substituted with an electron withdrawing group. Reduction of amides of formula (1-5) with a reagent such as optionally heated borane tetrahydrofuran complex delivers compounds of formula (1-6). Compounds of formulas (1-3), (1-4), (1-5) and (1-6) are representative of compounds of formula (I).

Scheme 2

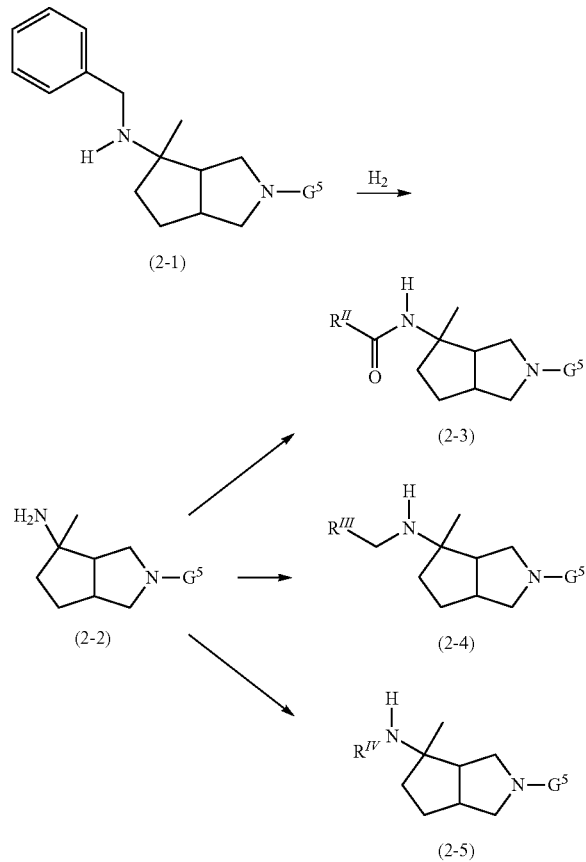

Compounds of formula (2-2), (2-3), (2-4), and (2-5) which are representative of compounds of formula (I) can be prepared as described in Scheme 2. Compounds of formula (2-1), wherein $G^5$ is as described in the Summary of the Invention, can be converted to compounds of formula (2-2) by treatment with hydrogen in the presence of an appropriate catalyst.

Compounds of formula (2-2) can be converted to compounds of formula (2-3) under amide bond forming conditions. $R^{II}$ is selected from $R^u$, $G^2$, $G^3$, —$(CR^aR^b)_m$-$G^2$, —$(CR^aR^b)_m$-$G^3$, —$(CR^cR^d)_q$—$N(R^y)$—$C(O)O$—$R^v$, —$(CR^cR^d)_q$—$N(R^y)$—$C(O)R^w$, —$(CR^cR^d)_q$—$N(R^y)$—$SO_2R^w$, —$(CR^cR^d)_q$—$N(R^y)(R^z)$, —$(CR^cR^d)_q$—$N(R^y)$—$C(O)N(R^y)(R^w)$, wherein $R^a$, $R^b$, $R^cR^d$, $R^u$, $R^v$, $R^w$, $R^y$, $R^z$, $G^2$, $G^3$, m and q are as described in the Summary of the Invention. Examples of conditions known to generate amides from a mixture of a carboxylic acid and an amine include but are not limited to adding a coupling reagent such as but not limited to N-(3-dimethylaminopropyl)-N'-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures.

Alternatively, compounds of formula (2-3) may be prepared from compounds of formula (2-2) by reacting with an acid chloride. Compounds of formula (2-2), may be treated with the corresponding acid chloride in a solvent such as dichloromethane in the presence of an amine such as triethylamine or diisopropylethylamine at room temperature over 1 to 24 hours to afford compounds of formula (2-3). Compounds of formula (2-3) are representative of compounds of formula (I).

Compounds of formula (2-2) can be reductively aminated with aldehydes of formula $R^{III}$—CHO in the presence of a reducing agent such as polymer-supported-cyanoborohydride, sodium cyanoborohydride, or sodium triacetoxyborohydride and acetic acid in a solvent such as methanol or dichloromethane at room temperature over 4-24 hours to supply compounds of formula (2-4), wherein $R^{III}$ is alkyl, optionally substituted aryl or optionally substituted heteroaryl. Compounds of formula (2-3) are representative of compounds of formula (I).

Compounds of formula (2-2) can also be cross-coupled to give compounds of formula (2-5), wherein $R^{IV}$ is optionally substituted aryl or optionally substituted heteroaryl. Accordingly compounds of formula (2-2) can be reacted with an optionally substituted aryl halide, an optionally substituted aryl sulfonate, an optionally substituted heteroaryl halide, or an optionally substituted heteroaryl sulfonate in the presence of a palladium or copper catalyst to give compounds of formula (2-5). Compounds of formula (2-5) are representative of compounds of formula (I).

Scheme 3

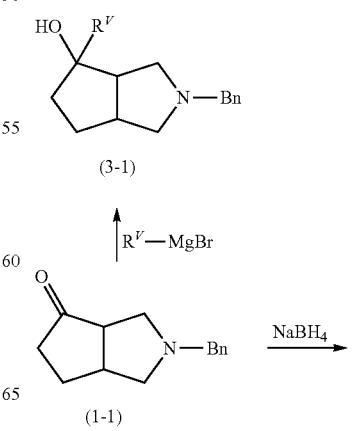

-continued

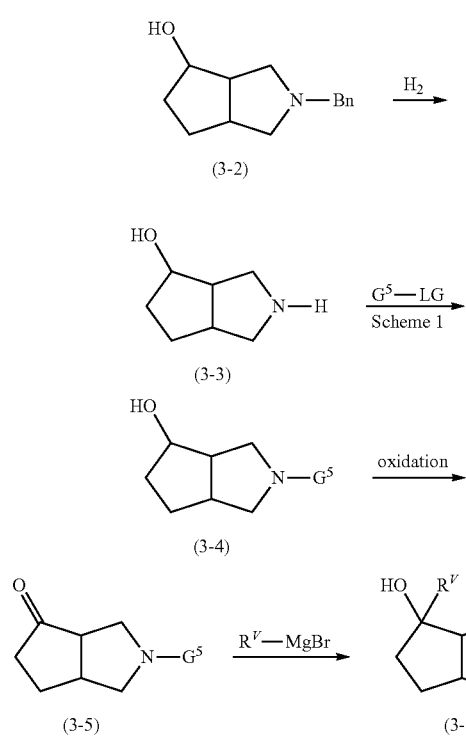

Compounds of formula (1-1) can also be converted to compounds of formula (3-1), wherein $R^V$ is alkyl, optionally substituted aryl, or optionally substituted arylalkyl. Compounds of formula (1-1) can be reacted with Grignard reagents of formula $R^V$—MgBr to give compounds of formula (3-1) which are representative of compounds of formula (I).

Compounds of formula (1-1) can also be reduced with a reagent such as sodium borohydride in the presence of a solvent such as methanol to give compounds of formula (3-2). The benzyl group of compounds of formula (3-2) can be removed by hydrogenolysis in the presence of an appropriate catalyst to give compounds of formula (3-3). Compounds of formula (3-3) can be cross-coupled with reagents of formula $G^5$-LG under conditions described in Scheme 1 to give compounds of formula (3-4). Compounds of formula (3-4) can be oxidized with reagents such as but not limited to Dess-Martin periodinane to give compounds of formula (3-5). Compounds of formula (3-5) can be reacted with Grignard reagents of formula $R^V$—MgBr to give compounds of formula (3-6). Compounds of formulas (3-4), (3-5) and (3-6) are representative of compounds of formula (I).

Scheme 4

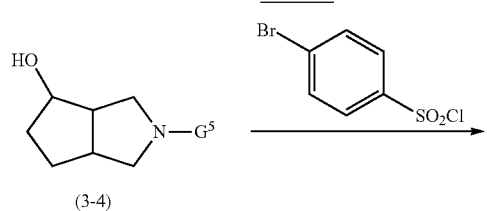

-continued

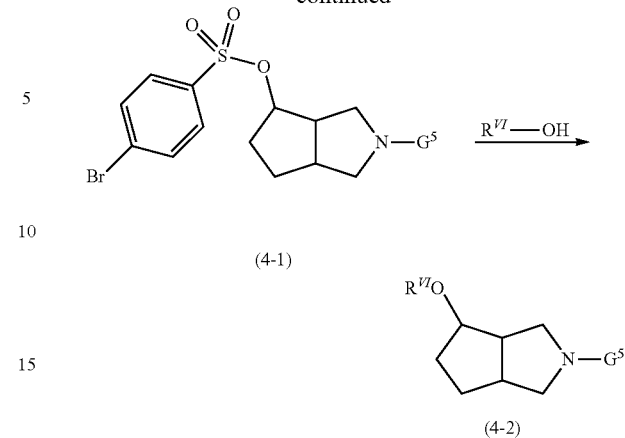

As shown in Scheme 4, compounds of formula (3-4) can be converted to compounds of formula (4-2), wherein $R^{VI}$ is alkyl, —$(CR^aR^b)_m$-$G^2$, or, —$(CR^aR^b)_m$-$G^3$, wherein $G^2$, $G^3$, and $G^5$ are as described in the Summary of the Invention. Compounds of formula (3-4) can be reacted with 4-bromobenzene-1-sulfonyl chloride in the presence of 1-methylimidazole and triethylamine in a solvent such as dichloromethane to give compounds of formula (4-1). Compounds of formula (4-1) can be reacted with optionally heated alcohols of formula $R^V$—OH to give compounds of formula (4-2). Compounds of formula (4-2) are representative of compounds of formula (I).

Scheme 5

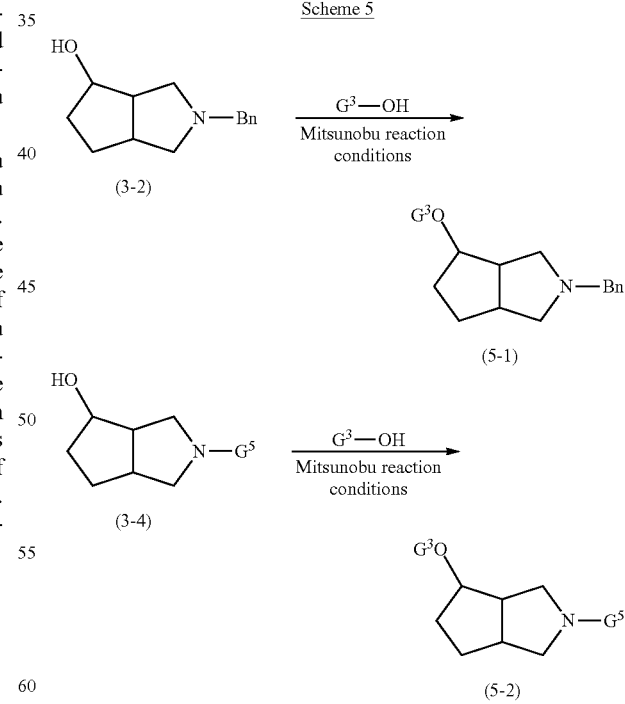

As described in Scheme 5, compounds of formulas (3-2) and (3-4) can be converted to compounds of formulas (5-1) and (5-2) respectively. Compounds of formula (3-2) can be reacted under Mitsunobu reaction conditions with $G^3$-OH, wherein $G^3$ is as described in the Summary of the Invention to give compounds of formula (5-1). Mitsunobu reaction conditions can include but are not limited to diisopropyl azodicarboxylate and triphenylphosphine in a solvent such as tetrahydrofuran. In like fashion, compounds of formula (3-4) can be converted to compounds of formula (5-2). Compounds of formulas (5-1) and (5-2) are representative of compounds of formula (I).

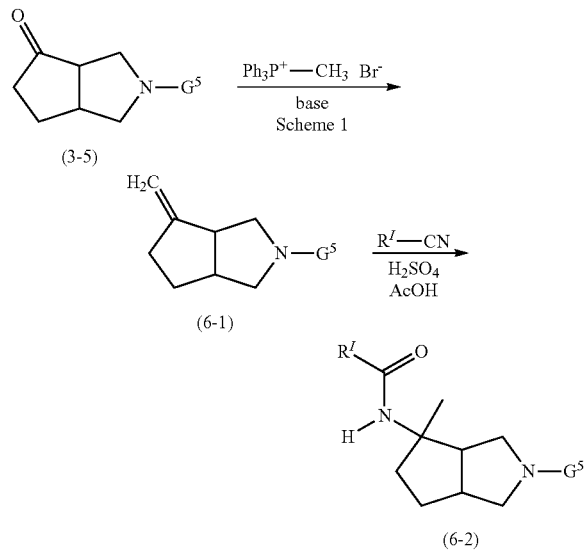

As described in Scheme 6, compounds of formulas (6-1) and (6-2) which are representative of compounds of formula (I) can be prepared from compounds of formula (3-5), wherein $G^5$ is as described in the Summary of the Invention. Compounds of formula (3-5) can be reacted with methyltriphenylphosphonium bromide in the presence of a base such as potassium tert-butoxide in a solvent such as tetrahydrofuran to give compounds of formula (6-1). Compounds of formula (6-1) can be reacted with $R^I$—CN, wherein $R^I$ is optionally substituted aryl, optionally substituted heteroaryl or alkyl, under Ritter reaction conditions to give compounds of formula (6-2). Compounds of formulas (6-1) and (6-2) are representative of compounds of formula (I).

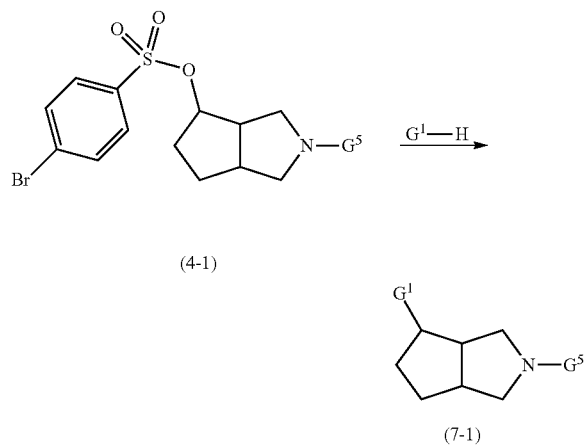

As described in Scheme 7, compounds of formula (7-1) can be prepared from compounds of formula (4-1). Compounds of formula (4-1) can be reacted with compounds of $G^1$-H, wherein $G^1$ is as described in the Summary of the Invention and the hydrogen is located at the attachment point shown in compounds of formulas (i), (ii), (iii) and (iv) also as described in the Summary of the Invention. The reaction can be conducted in optionally heated toluene to give compounds of formula (7-1) which are representative of compounds of formula (I).

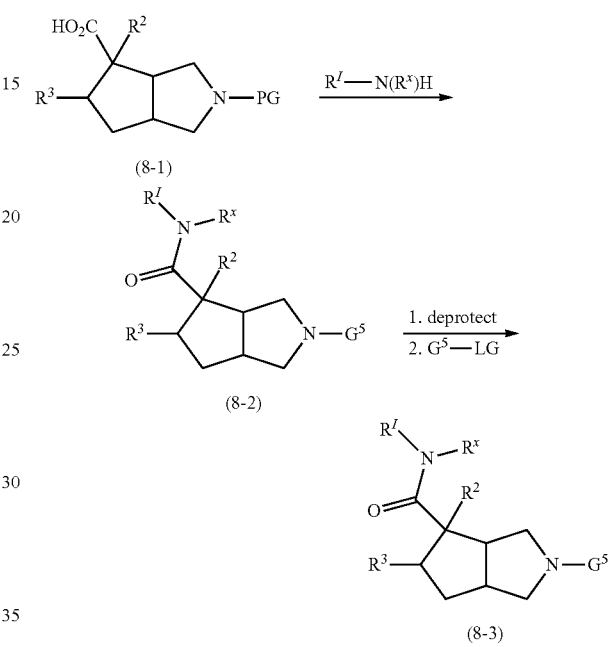

As described in Scheme 8, compounds of formula (8-3), wherein $R^I$, $R^x$, $R^2$, $R^3$ and $G^5$ are as previously described can be prepared from compounds of formula (8-1), wherein PG is a suitable nitrogen protecting group. Compounds of formula (8-1) can be coupled with amines of formula $R^I$—N($R^x$)H. Examples of conditions known to generate amides from a mixture of a carboxylic acid and an amine include but are not limited to adding a coupling reagent such as but not limited to N-(3-dimethylaminopropyl)-N'-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures.

Alternatively, compounds of formula (8-2) may be prepared from compounds of formula (8-1) by first transforming compounds of formula (8-1) to the corresponding acid chloride with oxalyl chloride or thionyl chloride under reaction conditions known to one skilled in the art. The acid chloride may be treated with compounds of formula $R^I$—$N(R^x)H$ in a solvent such as dichloromethane in the presence of an amine such as triethylamine or diisopropylethylamine at room temperature over 1 to 24 hours to afford compounds of formula (8-2).

Compounds of formula (8-2) can be transformed to compounds of formula (8-3) in a two-step process. The initial step involves removal of the protecting group, PG, under conditions known to one skilled in the art and dependent upon the protecting group. Subsequently, coupling with $G^5$-LG, wherein LG is a leaving group such as iodine, bromine or chlorine, under cross-coupling conditions known to one skilled in the art to give compounds of formula (8-3). Alternatively, when $G^5$-LG represents a pyridyl halide or pyrimidinyl halide, heating in a solvent such as ethanol in the presence of a base such as triethylamine delivers compounds of formula (8-3). The reaction is enhanced when the pyridyl halide or pyrimidinyl halide are substituted with an electron withdrawing group. Compounds of formula (8-3) are representative of compounds of formula (I).

Scheme 9

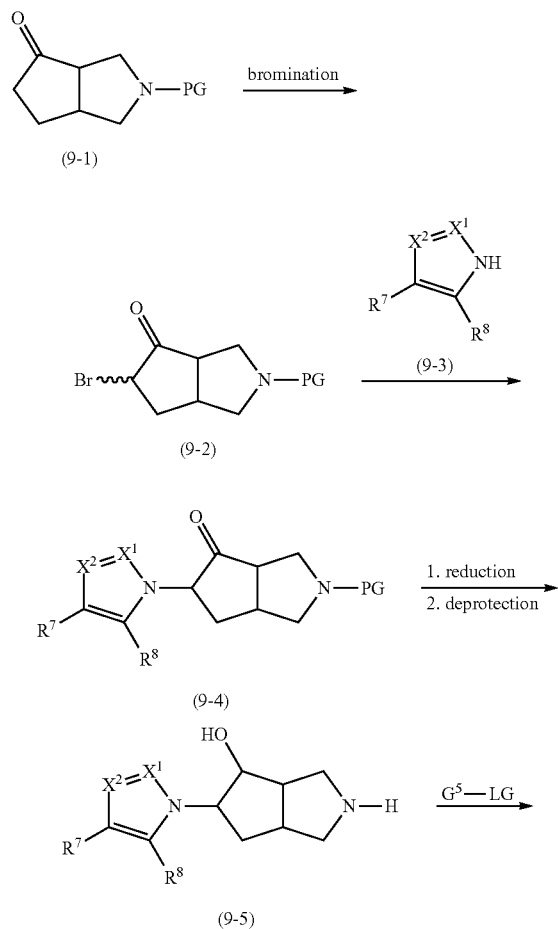

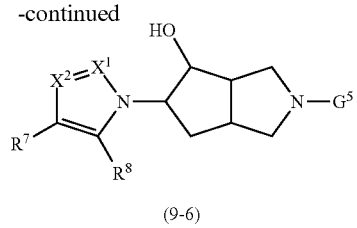

(9-6)

As described in Scheme 9, compounds of formula (9-6), wherein $X^1$, $X^2$, $R^7$, $R^8$ and $G^5$ are as described in the Summary can be prepared from compounds of formula (9-1), wherein PG is a suitable nitrogen protecting group. Compounds of formula (9-1) can be brominated with a reagent such as but not limited to pyridinium bromide perbromide to give compounds of formula (9-2). Compounds of formula (9-2) can be reacted with compounds of formula (9-3) optionally under heated reaction conditions to give compounds of formula (9-4). The ketone moiety of compounds of formula (9-4) can be reduced with a reagent such as but not limited to sodium borohydride, and the protecting group can be removed under conditions known to one skilled in the art dependent upon the chosen protecting group to give compounds of formula (9-5). Compounds of formula (9-5) can be coupled with $G^5$-LG, wherein LG is a leaving group such as iodine, bromine or chlorine, under cross-coupling conditions known to one skilled in the art to give compounds of formula (9-6). Alternatively, when $G^5$-LG represents a pyridyl halide or pyrimidinyl halide, heating in a solvent such as ethanol in the presence of a base such as triethylamine delivers compounds of formula (9-6). The reaction is enhanced when the pyridyl halide or pyrimidinyl halide are substituted with an electron withdrawing group. Compounds of formula (9-6) are representative of compounds of formula (I).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protective Groups in Organic Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

Abbreviations: ESI for electrospray ionization; and psi for pounds per square inch.

Example 1

(3aS,6aS)-2-benzyl-4-methyleneoctahydrocyclopenta[c]pyrrole

The title compound was prepared by combining (3aR, 6aS)-2-benzylhexahydrocyclopenta[c]pyrrol-4(5H)-one (100 mg, 0.464 mmol) [prepared as described by Santora, V. J., et. al. Bioorganic & Medicinal Chemistry Letters 2008, 18(4), 1490-1494] in 2 mL of tetrahydrofuran with methyltriphenylphosphonium bromide (249 mg, 0.697 mmol) and potassium tert-butoxide (78 mg, 0.697 mmol). The reaction was stirred at room temperature overnight, concentrated, and the crude material was purified by silica gel chromatography using 1-100% ethyl acetate/hexanes to give the title compound: $^1$H NMR (400 MHz, pyridine-d$_5$) δ ppm 7.47-7.41 (m, 2H), 7.40-7.33 (m, 2H), 7.31-7.25 (m, 1H), 4.93-4.89 (m, 1H), 4.80-4.76 (m, 1H), 3.55 (d, J=13.1, 1H), 3.47 (d, J=13.1, 1H), 2.96-2.87 (m, 1H), 2.63-2.41 (m, 5H), 2.33 (dd, J=8.9, 3.9, 1H), 2.17 (dddt, J=14.9, 7.4, 5.8, 1.6, 1H), 1.68 (ddd, J=16.0, 12.4, 8.1, 1H), 1.51-1.39 (m, 1H); MS (ESI+) m/z 227 (M+H)$^+$.

Example 2

N-[(3aR,4R,6aS)-2-benzyl-4-methyloctahydrocyclopenta[c]pyrrol-4-yl]benzamide and Example 3

N-[(3aR,4S,6aS)-2-benzyl-4-methyloctahydrocyclopenta[c]pyrrol-4-yl]benzamide

Sulfuric acid (1.437 mL, 27.0 mmol) was added to a solution of (3aS,6aS)-2-benzyl-4-methyleneoctahydrocyclopenta[c]pyrrole (0.575 g, 2.70 mmol, Example 1) in acetic acid (1.466 mL, 25.6 mmol) and benzonitrile (1.390 mL, 13.48 mmol) at 0° C. The reaction was stirred at room temperature overnight. The reaction mixture was quenched with ice, extracted with dichloromethane, and then purified by silica gel chromatography using 1-10% methanol (2 N ammonia)/dichloromethane as eluent to give the title compounds.

Example 2: $^1$H NMR (500 MHz, pyridine-d$_5$) δ ppm 8.85 (s, 1H), 8.07-8.03 (m, 2H), 7.52-7.43 (m, 3H), 7.38-7.27 (m, 5H), 3.65 (d, J=12.6, 1H), 3.47 (d, J=12.6, 1H), 3.03 (d, J=10.1, 1H), 2.73 (ddd, J=12.1, 6.2, 3.2, 1H), 2.60-2.52 (m, 2H), 2.43-2.38 (m, 1H), 2.26 (dd, J=10.0, 7.0, 1H), 2.21 (t, J=9.1, 1H), 1.85-1.77 (m, 1H), 1.72 (s, 3H), 1.44-1.37 (m, 1H), 1.33-1.24 (m, 1H); MS (ESI+) m/z 335.2 (M+H)$^+$.

Example 3: $^1$H NMR (500 MHz, pyridine-d$_5$) δ ppm 8.16-8.07 (m, 2H), 7.98 (s, 1H), 7.47 (d, J=7.0, 2H), 7.43-7.33 (m, 5H), 7.30 (t, J=7.3, 1H), 3.58-3.49 (m, 2H), 3.24 (td, J=8.3, 5.0, 1H), 2.78-2.68 (m, 2H), 2.57 (dd, J=13.0, 5.3, 2H), 2.47-2.40 (m, 1H), 2.27 (dd, J=9.0, 4.1, 1H), 2.06-1.97 (m, 1H), 1.92 (ddd, J=12.3, 9.9, 6.6, 1H), 1.73 (s, 3H), 1.48-1.39 (m, 1H); MS (ESI+) m/z 335.2 (M+H)$^+$.

Example 4

N-[(3aR,4R,6aS)-2-benzyl-4-methyloctahydrocyclopenta[c]pyrrol-4-yl]acetamide and Example 5

N-[(3aR,4S,6aS)-2-benzyl-4-methyloctahydrocyclopenta[c]pyrrol-4-yl]acetamide

The title compounds were prepared by substituting acetonitrile for benzonitrile in the procedure that describes the preparation of Examples 2 and 3.

Example 4: $^1$H NMR (500 MHz, pyridine-d$_5$) δ ppm 8.21 (s, 1H), 7.40 (ddd, J=15.1, 10.6, 4.6, 4H), 7.34-7.26 (m, 1H), 3.56 (d, J=12.8, 1H), 3.43 (d, J=12.8, 1H), 2.79 (dd, J=9.8, 2.4, 1H), 2.55 (tdd, J=7.8, 7.2, 2.6, 2H), 2.43 (ddd, J=18.7, 11.3, 4.7, 2H), 2.34 (ddd, J=11.1, 9.6, 7.4, 2H), 1.99 (s, 3H), 1.83-1.72 (m, 1H), 1.55 (s, 3H), 1.42 (dt, J=11.9, 7.0, 1H), 1.29 (ddd, J=19.7, 7.1, 4.9, 1H); MS (ESI+) m/z 273 (M+H)$^+$.

Example 5: $^1$H NMR (500 MHz, pyridine-d$_5$) δ ppm 7.85 (s, 1H), 7.48-7.42 (m, 2H), 7.37 (dd, J=10.4, 4.7, 2H), 7.28 (t, J=7.3, 1H), 3.55-3.47 (m, 2H), 3.10 (dd, J=15.4, 6.8, 1H), 2.74-2.65 (m, 1H), 2.60 (dd, J=8.8, 7.9, 1H), 2.56 (d, J=6.7, 2H), 2.35-2.27 (m, 1H), 2.19 (dd, J=8.9, 4.5, 1H), 2.00 (s, 3H), 1.99-1.92 (m, 1H), 1.80 (ddd, J=12.4, 10.4, 6.9, 1H), 1.64 (s, 3H), 1.38 (ddt, J=13.4, 6.8, 3.5, 1H); MS (ESI+) m/z 273 (M+H)$^+$.

Example 6

N-[(3aR,4R,6aS)-2-benzyl-4-methyloctahydrocyclopenta[c]pyrrol-4-yl]-3-fluorobenzamide and Example 7

N-[(3aR,4S,6aS)-2-benzyl-4-methyloctahydrocyclopenta[c]pyrrol-4-yl]-3-fluorobenzamide The title compounds were prepared by substituting 3-fluorobenzonitrile for benzonitrile in the procedure that describes the preparation of Examples 2 and 3.

Example 6: ¹H NMR (400 MHz, pyridine-$d_5$) δ ppm 8.88 (s, 1H), 7.84 (ddd, J=9.7, 2.7, 1.6, 1H), 7.79-7.69 (m, 1H), 7.47-7.28 (m, 7H), 3.66 (d, J=12.7, 1H), 3.49 (d, J=12.7, 1H), 3.01 (d, J=10.1, 1H), 2.68 (ddd, J=11.9, 6.3, 3.7, 1H), 2.62-2.48 (m, 2H), 2.43 (dd, J=9.1, 7.6, 1H), 2.34-2.16 (m, 2H), 1.91-1.75 (m, 1H), 1.70 (s, 3H), 1.50-1.35 (m, 1H), 1.34-1.20 (m, 1H); MS (ESI+) m/z 353 (M+H)⁺.

Example 7: ¹H NMR (400 MHz, pyridine-$d_5$) δ ppm 8.17 (s, 1H), 7.93-7.86 (m, 2H), 7.47 (d, J=7.1, 2H), 7.39 (dd, J=10.2, 4.7, 2H), 7.30 (ddd, J=8.6, 7.1, 3.6, 2H), 7.20-7.15 (m, 1H), 3.58-3.49 (m, 2H), 3.23 (td, J=8.3, 5.0, 1H), 2.78-2.68 (m, 2H), 2.56 (t, J=8.8, 2H), 2.46-2.38 (m, 1H), 2.28 (dd, J=9.0, 4.1, 1H), 2.07-1.87 (m, 2H), 1.72 (s, 3H), 1.48-1.40 (m, 1H); MS (ESI+) m/z 353 (M+H)⁺.

Example 8

N-[(3aR,4R,6aS)-4-methyloctahydrocyclopenta[c]pyrrol-4-yl]benzamide

N-[(3aR,4R,6aS)-2-benzyl-4-methyloctahydrocyclopenta[c]pyrrol-4-yl]benzamide from Example 2 (250 mg, 0.747 mmol) and trifluoroethanol (10 mL) were added to 20% Pd(OH)₂—C, wet (50.0 mg, 0.356 mmol) in a 50 mL pressure bottle and stirred for 2 hours under 30 psi hydrogen gas at 50° C. The mixture was filtered through a nylon membrane and the solvent removed in vacuo to give the title compound as a white solid: ¹H NMR (500 MHz, pyridine-$d_5$) δ ppm 9.40 (s, 1H), 8.22-8.15 (m, 2H), 7.46-7.38 (m, 3H), 3.15 (dd, J=10.2, 1.3, 1H), 2.91-2.86 (m, 1H), 2.83-2.77 (m, 1H), 2.75-2.66 (m, 2H), 2.54 (qd, J=9.1, 2.0, 1H), 2.38 (dd, J=11.8, 4.4, 1H), 1.92-1.84 (m, 1H), 1.75 (s, 3H), 1.49-1.41 (m, 1H), 1.32 (ddt, J=13.0, 10.5, 6.6, 1H); MS (ESI+) m/z 245 (M+H)⁺.

Example 9

N-[(3aR,4S,6aS)-4-methyloctahydrocyclopenta[c]pyrrol-4-yl]benzamide

The title compound was prepared by substituting N-[(3aR,4S,6aS)-2-benzyl-4-methyloctahydrocyclopenta[c]pyrrol-4-yl]benzamide from Example 3 for N-[(3aR,4R,6aS)-2-benzyl-4-methyloctahydrocyclopenta[c]pyrrol-4-yl]acetamide in the procedure that describes the preparation of Example 8: ¹H NMR (500 MHz, pyridine-$d_5$) δ ppm 8.15-8.09 (m, 2H), 7.97 (s, 1H), 7.43-7.33 (m, 3H), 3.19-3.07 (m, 3H), 2.91 (dd, J=10.8, 6.0, 1H), 2.74-2.65 (m, 1H), 2.56 (dd, J=10.5, 4.9, 1H), 2.52-2.45 (m, 1H), 2.09-1.99 (m, 1H), 1.78 (ddd, J=12.9, 10.4, 7.3, 1H), 1.73 (s, 3H), 1.42-1.33 (m, 1H); MS (ESI+) m/z 245 (M+H)⁺.

Example 10

N-[(3aR,4R,6aS)-4-methyloctahydrocyclopenta[c]pyrrol-4-yl]acetamide

The title compound was prepared by substituting N-[(3aR,4R,6aS)-2-benzyl-4-methyloctahydrocyclopenta[c]pyrrol-4-yl]acetamide from Example 4 for N-[(3aR,4R,6aS)-2-benzyl-4-methyloctahydrocyclopenta[c]pyrrol-4-yl]benzamide in the procedure that describes the preparation of Example 8: ¹H NMR (500 MHz, pyridine-$d_5$) δ ppm 8.43 (s, 1H), 3.06-3.00 (m, 3H), 2.70 (dt, J=9.1, 6.1, 1H), 2.65 (dd, J=10.2, 3.8, 1H), 2.57-2.48 (m, 1H), 2.26 (dt, J=12.1, 7.9, 1H), 1.99 (s, 3H), 1.84-1.75 (m, 1H), 1.59 (s, 3H), 1.54-1.46 (m, 1H), 1.36-1.27 (m, 2H); MS (ESI+) m/z 183 (M+H)⁺.

Example 11

N-[(3aR,4S,6aS)-4-methyloctahydrocyclopenta[c]pyrrol-4-yl]acetamide

The title compound was prepared by substituting N-[(3aR,4S,6aS)-2-benzyl-4-methyloctahydrocyclopenta[c]pyrrol-4-yl]acetamide from Example 5 for N-[(3aR,4R,6aS)-2-benzyl-4-methyloctahydrocyclopenta[c]pyrrol-4-yl]benzamide in the procedure that describes the preparation of Example 8: ¹H NMR (500 MHz, pyridine-$d_5$) δ ppm 7.91 (s, 1H), 3.21-3.12 (m, 2H), 3.08 (dd, J=15.1, 8.3, 1H), 2.89 (dd, J=10.7, 6.3, 1H), 2.75-2.66 (m, 1H), 2.61 (dd, J=10.6, 5.2, 1H), 2.38-2.30 (m, 1H), 2.05-1.94 (m, 4H), 1.74-1.66 (m, 1H), 1.64 (s, 3H), 1.36 (ddd, J=12.9, 7.2, 3.5, 2H); MS (ESI+) m/z 183 (M+H)⁺.

Example 12

3-fluoro-N-[(3aR,4R,6aS)-4-methyloctahydrocyclopenta[c]pyrrol-4-yl]benzamide

The title compound was prepared by substituting N-[(3aR,4R,6aS)-2-benzyl-4-methyloctahydrocyclopenta[c]pyrrol-4-yl]-3-fluorobenzamide from Example 6 for N-[(3aR,4R,6aS)-2-benzyl-4-methyloctahydrocyclopenta[c]pyrrol-4-yl]benzamide in the procedure that describes the preparation of Example 8: ¹H NMR (500 MHz, pyridine-$d_5$) δ ppm 9.55-9.39 (m, 1H), 7.92 (ddd, J=6.5, 4.5, 2.4, 2H), 7.46-7.40 (m, 1H), 7.39-7.32 (m, 1H), 7.25-7.22 (m, 1H), 3.12 (dd, J=8.0, 2.3, 1H), 2.84 (t, J=8.9, 1H), 2.77-2.67 (m, 2H), 2.64 (dd, J=9.4, 2.1, 1H), 2.56-2.48 (m, 1H), 2.33-2.26 (m, 1H), 1.93-1.84 (m, 1H), 1.76 (d, J=8.8, 3H), 1.46-1.37 (m, 1H), 1.34-1.25 (m, 1H); MS (ESI+) m/z 263 (M+H)⁺.

Example 13

3-fluoro-N-[(3aR,4S,6aS)-4-methyloctahydrocyclopenta[c]pyrrol-4-yl]benzamide

The title compound was prepared by substituting N-[(3aR,4S,6aS)-2-benzyl-4-methyloctahydrocyclopenta[c]pyrrol-4-yl]-3-fluorobenzamide from Example 7 for N-[(3aR,4R,6aS)-2-benzyl-4-methyloctahydrocyclopenta[c]pyrrol-4-yl]benzamide in the procedure that describes the preparation of Example 8: ¹H NMR (500 MHz, pyridine-$d_5$) δ ppm 8.15 (d, J=0.7, 1H), 7.90 (ddd, J=11.8, 6.5, 4.7, 2H), 7.31 (td, J=8.0, 5.8, 1H), 7.19-7.16 (m, 1H), 3.18-3.07 (m, 3H), 2.95-2.89 (m, 1H), 2.74-2.65 (m, 1H), 2.59-2.53 (m, 1H), 2.50-2.43 (m, 1H), 2.14 (s, 1H), 2.04 (dddd, J=9.9, 8.9, 7.8, 4.1, 1H), 1.83-1.75 (m, 1H), 1.73 (s, 3H), 1.41-1.34 (m, 1H); MS (ESI+) m/z 263 (M+H)⁺.

Example 14

N-{(3aR,4R,6aS)-4-methyl-2-[6-(trifluoromethyl)pyridin-2-yl]octahydrocyclopenta[c]pyrrol-4-yl}benzamide N-[(3aR,4R,6aS)-4-methyloctahydrocyclopenta[c]pyrrol-4-yl]benzamide (118 mg, 0.483 mmol, Example 8) was combined with 2-bromo-6-(trifluoromethyl)pyridine (131 mg, 0.580 mmol) and triethylamine (0.202 mL, 1.449 mmol) in ethanol (0.2 mL). The reaction was heated at 75° C. for 72 hours. The reaction mixture was partitioned between water (1 mL) and dichloromethane. The crude brown material was purified by silica gel chromatography using 1-10% methanol (2 N ammonia)/dichloromethane as eluent to give the title compound: ¹H NMR (400 MHz, pyridine-$d_5$) δ ppm 8.71 (s, 1H), 8.16 (dd, J=5.3, 3.3, 2H), 7.47 (t, J=7.9, 1H), 7.43-7.30 (m, 3H), 6.96 (d, J=7.2, 1H), 6.46 (d, J=8.6, 1H), 3.79-3.64 (m, 2H), 3.60 (dd, J=11.1, 7.3, 1H), 3.56-3.45 (m, 2H), 2.80-2.69 (m, 1H), 2.25 (dd, J=21.5, 9.6, 1H), 2.00-1.78 (m, 2H), 1.64 (s, 3H), 1.45-1.33 (m, 1H); MS (ESI+) m/z 390 (M+H)⁺.

Example 15

N-{(3aR,4S,6aS)-4-methyl-2-[6-(trifluoromethyl)pyridin-2-yl]octahydrocyclopenta[c]pyrrol-4-yl}benzamide The title compound was prepared by substituting N-[(3aR,4S,6aS)-4-methyloctahydrocyclopenta[c]pyrrol-4-yl]benzamide from Example 9 for N-[(3aR,4R,6aS)-4-methyloctahydrocyclopenta[c]pyrrol-4-yl]benzamide in the procedure described in Example 14: ¹H NMR (400 MHz, pyridine-$d_5$) δ ppm 8.26 (s, 1H), 8.19-8.10 (m, 2H), 7.55 (d, J=7.9, 1H), 7.47-7.32 (m, 3H), 7.01 (d, J=7.2, 1H), 6.58 (d, J=8.6, 1H), 3.74-3.61 (m, 2H), 3.53 (ddd, J=23.5, 13.0, 8.1, 2H), 3.37 (dd, J=10.9, 3.2, 1H), 3.01-2.90 (m, 1H), 2.46 (ddd, J=13.0, 8.1, 5.0, 1H), 2.13 (dq, J=13.3, 8.2, 1H), 1.99-1.88 (m, 1H), 1.65 (s, 3H), 1.45 (ddd, J=13.5, 9.5, 5.0, 1H); MS (ESI+) m/z 390 (M+H)⁺.

Example 16

N-{(3aR,4R,6aS)-4-methyl-2-[6-(trifluoromethyl)pyridin-2-yl]octahydrocyclopenta[c]pyrrol-4-yl}acetamide The title compound was prepared by substituting N-[(3aR,4R,6aS)-4-methyloctahydrocyclopenta[c]pyrrol-4-yl]acetamide from Example 10 for N-[(3aR,4R,6aS)-4-methyloctahydrocyclopenta[c]pyrrol-4-yl]benzamide in the procedure described in Example 14: ¹H NMR (500 MHz, pyridine-$d_5$) δ ppm 8.47 (s, 1H), 7.51-7.46 (m, 1H), 6.97 (d, J=7.2, 1H), 6.51 (d, J=8.7, 1H), 3.81-3.70 (m, 1H), 3.64-3.53 (m, 2H), 3.47-3.35 (m, 2H), 2.72-2.64 (m, 1H), 2.04-1.95 (m, 4H), 1.93-1.82 (m, 1H), 1.76-1.69 (m, 1H), 1.55 (s, 3H), 1.38-1.30 (m, 1H); MS (ESI+) m/z 328 (M+H)⁺.

Example 17

N-{(3aR,4S,6aS)-4-methyl-2-[6-(trifluoromethyl)pyridin-2-yl]octahydrocyclopenta[c]pyrrol-4-yl}acetamide The title compound was prepared by substituting N-[(3aR,4S,6aS)-4-methyloctahydrocyclopenta[c]pyrrol-4-yl]acetamide from Example 11 for N-[(3aR,4R,6aS)-4-methyloctahydrocyclopenta[c]pyrrol-4-yl]benzamide in the procedure described in Example 14: ¹H NMR (500 MHz, pyridine-$d_5$) δ ppm 8.09 (s, 1H), 7.56-7.51 (m, 1H), 6.99 (d, J=7.2, 1H), 6.54 (d, J=8.6, 1H), 3.66-3.59 (m, 1H), 3.54 (dt, J=10.8, 7.1, 2H), 3.39-3.27 (m, 2H), 2.94-2.85 (m, 1H), 2.26 (ddd, J=13.0, 8.1, 4.7, 1H), 2.11-2.00 (m, 4H), 1.81 (dt, J=13.3, 8.5, 1H), 1.55 (s, 3H), 1.39 (dq, J=9.3, 4.9, 1H); MS (ESI+) m/z 328 (M+H)⁺.

Example 18

3-fluoro-N-{(3aR,4R,6aS)-4-methyl-2-[6-(trifluoromethyl)pyridin-2-yl]octahydrocyclopenta[c]pyrrol-4-yl}benzamide The title compound was prepared by substituting 3-fluoro-N-[(3aR,4R,6aS)-4-methyloctahydrocyclopenta[c]pyrrol-4-yl]benzamide from Example 12 for N-[(3aR,4R,6aS)-4-methyloctahydrocyclopenta[c]pyrrol-4-yl]benzamide in the procedure described in Example 14: ¹H NMR (500 MHz, pyridine-$d_5$) δ ppm 8.83 (s, 1H), 8.20-8.09 (m, 0.5H), 7.93 (dd, J=14.7, 5.0, 1.5H), 7.50-7.44 (m, 1H), 7.43-7.26 (m, 2H), 6.96 (d, J=7.2, 1H), 6.51 (d, J=8.6, 1H), 3.81-3.73 (m, 1H), 3.69 (dd, J=11.2, 6.8, 1H), 3.60 (dd, J=10.9, 7.4, 1H), 3.50 (dt, J=16.5, 8.2, 2H), 2.78-2.70 (m, 1H), 2.24 (dt, J=22.1, 8.0, 1H), 1.93 (ddd, J=18.3, 13.6, 9.7, 1H), 1.85-1.78 (m, 1H), 1.64 (s, 3H), 1.44-1.36 (m, 1H); MS (ESI+) m/z 408 (M+H)⁺.

Example 19

3-fluoro-N-{(3aR,4S,6aS)-4-methyl-2-[6-(trifluoromethyl)pyridin-2-yl]octahydrocyclopenta[c]pyrrol-4-yl}benzamide The title compound was prepared by substituting 3-fluoro-N-[(3aR,4S,6aS)-4-methyloctahydrocyclopenta[c]pyrrol-4-yl]benzamide from Example 13 for N-[(3aR,4R,6aS)-4-methyloctahydrocyclopenta[c]pyrrol-4-yl]benzamide in the procedure described in Example 14: ¹H NMR (500 MHz, pyridine-$d_5$) δ ppm 8.40 (s, 1H), 7.92 (d, J=1.6, 2H), 7.56 (s, 1H), 7.40-7.29 (m, 2H), 7.01 (d, J=7.3, 1H), 6.58 (d, J=8.6, 1H), 3.73-3.62 (m, 2H), 3.57 (dd, J=10.8, 8.0, 1H), 3.48 (dd, J=15.1, 8.1, 1H), 3.37 (d, J=7.8, 1H), 2.96 (dd, J=8.2, 4.3, 1H), 2.43 (ddd, J=13.2, 8.0, 5.1, 1H), 2.18-2.07 (m, 1H), 1.97-1.89 (m, 1H), 1.65 (s, 3H), 1.49-1.40 (m, 1H); MS (ESI+) m/z 408 (M+H)⁺.

Example 20

(3aR,4S,6aS)—N-benzyl-4-methyl-2-[6-(trifluoromethyl)pyridin-2-yl]octahydrocyclopenta[c]pyrrol-4-amine To a solution of N-{(3aR,4S,6aS)-4-methyl-2-[6-(trifluoromethyl)pyridin-2-yl]octahydrocyclopenta[c]pyrrol-4-yl}benzamide (180 mg, 0.462 mmol) from Example 15 in tetrahydrofuran (1 mL) was added dropwise borane tetrahydrofuran complex solution (1.387 mL, 1.387 mmol). The reaction was heated at 80° C. for 3 hours, quenched with 2 N HCl (0.5 mL) and then stirred for 1 hour. The reaction mixture was neutralized with aqueous sodium bicarbonate and extracted with dichloromethane. The combined organic washes were purified by silica gel chromatography using 1-10% methanol (2 N ammonia)/dichloromethane as eluent to give the title compound: ¹H NMR (500 MHz, pyridine-$d_5$) δ ppm 8.69 (d, J=8.0, 1H), 8.65 (d, J=7.4, 2H), 8.57-8.48 (m, 2H), 8.44 (t, J=7.3, 1H), 8.14 (d, J=7.2, 1H), 7.69 (d, J=8.6, 1H), 4.92-4.83 (m, 2H), 4.76-4.65 (m, 2H), 4.52-4.46 (m, 1H), 4.46-4.39 (m, 1H), 4.13-4.05 (m, 1H), 3.72 (dd, J=15.8, 7.9, 1H), 3.26 (dq, J=13.2, 8.3, 1H), 2.87-2.73 (m, 2H), 2.71-2.58 (m, 1H), 2.49 (dq, J=9.4, 5.0, 1H), 2.29 (s, 3H); MS (ESI+) m/z 376 (M+H)⁺.

Example 21

(3aR,4R,6aS)—N-benzyl-4-methyl-2-[6-(trifluoromethyl)pyridin-2-yl]octahydrocyclopenta[c]pyrrol-4-amine The title compound was prepared by substituting N-{(3aR,4R,6aS)-4-methyl-2-[6-(trifluoromethyl)pyridin-2-yl]octahydrocyclopenta[c]pyrrol-4-yl}benzamide from Example 14 for N-{(3aR,4S,6aS)-4-methyl-2-[6-(trifluoromethyl)pyridin-2-yl]octahydrocyclopenta[c]pyrrol-4-yl}benzamide in the procedure that describes the preparation of Example 20: $^1$H NMR (500 MHz, pyridine-$d_5$) δ ppm 7.50 (t, J=8.9, 3H), 7.36 (dd, J=10.3, 4.7, 2H), 7.27 (t, J=7.3, 1H), 6.96 (d, J=7.2, 1H), 6.52 (d, J=8.6, 1H), 3.87-3.76 (m, 2H), 3.72 (d, J=12.8, 1H), 3.58-3.43 (m, 3H), 2.72-2.62 (m, 1H), 2.53-2.45 (m, 1H), 1.97-1.79 (m, 3H), 1.54-1.45 (m, 1H), 1.38 (ddd, J=17.6, 9.1, 3.9, 1H), 1.21 (s, 3H); MS (ESI+) m/z 376 (M+H)$^+$.

Example 22

(3aR,4R,6aS)—N-ethyl-4-methyl-2-[6-(trifluoromethyl)pyridin-2-yl]octahydrocyclopenta[c]pyrrol-4-amine The title compound was prepared by substituting N-{(3aR,4R,6aS)-4-methyl-2-[6-(trifluoromethyl)pyridin-2-yl]octahydrocyclopenta[c]pyrrol-4-yl}acetamide from Example 16 for N-{(3aR,4S,6aS)-4-methyl-2-[6-(trifluoromethyl)pyridin-2-yl]octahydrocyclopenta[c]pyrrol-4-yl}benzamide in the procedure that describes the preparation of Example 20: $^1$H NMR (500 MHz, pyridine-$d_5$) δ ppm 7.54-7.46 (m, 1H), 6.97 (d, J=7.2, 1H), 6.53 (d, J=8.6, 1H), 3.72 (dd, J=11.1, 7.4, 1H), 3.53 (dd, J=10.6, 7.1, 2H), 3.43 (d, J=10.6, 1H), 2.62 (ddd, J=17.8, 10.3, 3.3, 2H), 2.53-2.46 (m, 1H), 2.42 (dd, J=16.9, 8.5, 1H), 1.96-1.84 (m, 1H), 1.82-1.70 (m, 1H), 1.49-1.42 (m, 1H), 1.39-1.22 (m, 2H), 1.13 (s, 3H), 1.02 (t, J=7.1, 3H); MS (ESI+) m/z 314 (M+H)$^+$.

Example 23

(3aR,4S,6aS)—N-ethyl-4-methyl-2-[6-(trifluoromethyl)pyridin-2-yl]octahydrocyclopenta[c]pyrrol-4-amine The title compound was prepared by substituting N-{(3aR,4S,6aS)-4-methyl-2-[6-(trifluoromethyl)pyridin-2-yl]octahydrocyclopenta[c]pyrrol-4-yl}acetamide from Example 17 for N-{(3aR,4S,6aS)-4-methyl-2-[6-(trifluoromethyl)pyridin-2-yl]octahydrocyclopenta[c]pyrrol-4-yl}benzamide in the procedure that describes the preparation of Example 20: $^1$H NMR (500 MHz, pyridine-$d_5$) δ ppm 7.55 (d, J=8.1, 1H), 7.00 (d, J=7.2, 1H), 6.55 (d, J=8.7, 1H), 3.54 (dt, J=10.7, 7.2, 2H), 3.34 (dd, J=11.4, 6.7, 1H), 3.26 (dd, J=10.5, 2.3, 1H), 2.95-2.88 (m, 1H), 2.52 (q, J=7.4, 3H), 2.13-2.03 (m, 1H), 1.64-1.55 (m, 2H), 1.33 (ddt, J=13.5, 8.3, 5.2, 1H), 1.28-1.22 (br.m., 1H), 1.10-1.05 (m, 6H); MS (ESI+) m/z 314 (M+H)$^+$.

Example 24

(3aR,4R,6aS)—N-(3-fluorobenzyl)-4-methyl-2-[6-(trifluoromethyl)pyridin-2-yl]octahydrocyclopenta[c]pyrrol-4-amine The title compound was prepared by substituting 3-fluoro-N-{(3aR,4R,6aS)-4-methyl-2-[6-(trifluoromethyl)pyridin-2-yl]octahydrocyclopenta[c]pyrrol-4-yl}benzamide from Example 18 for N-{(3aR,4S,6aS)-4-methyl-2-[6-(trifluoromethyl)pyridin-2-yl]octahydrocyclopenta[c]pyrrol-4-yl}benzamide in the procedure that describes the preparation of Example 20: $^1$H NMR (500 MHz, pyridine-$d_5$) δ ppm 7.50 (t, J=7.9, 1H), 7.35-7.23 (m, 3H), 7.07-7.00 (m, 1H), 6.97 (d, J=7.2, 1H), 6.53 (d, J=8.6, 1H), 3.80 (dd, J=12.0, 7.4, 2H), 3.72 (d, J=13.7, 1H), 3.55 (dd, J=10.6, 7.4, 2H), 3.47 (d, J=10.4, 1H), 2.72-2.63 (m, 1H), 2.49 (dd, J=16.3, 7.6, 1H), 2.18-2.00 (m, 1H), 1.98-1.79 (m, 2H), 1.54-1.47 (m, 1H), 1.39 (ddd, J=17.5, 9.0, 4.0, 1H), 1.20 (s, 3H); MS (ESI+) m/z 394 (M+H)$^+$.

Example 25

(3aR,4S,6aS)—N-(3-fluorobenzyl)-4-methyl-2-[6-(trifluoromethyl)pyridin-2-yl]octahydrocyclopenta[c]pyrrol-4-amine The title compound was prepared by substituting 3-fluoro-N-{(3aR,4S,6aS)-4-methyl-2-[6-(trifluoromethyl)pyridin-2-yl]octahydrocyclopenta[c]pyrrol-4-yl}benzamide from Example 19 for N-{(3aR,4S,6aS)-4-methyl-2-[6-(trifluoromethyl)pyridin-2-yl]octahydrocyclopenta[c]pyrrol-4-yl}benzamide in the procedure that describes the preparation of Example 20: $^1$H NMR (500 MHz, pyridine-$d_5$) δ ppm 7.43-7.25 (m, 4H), 7.10-7.03 (m, 1H), 7.01 (d, J=7.2, 1H), 6.57 (d, J=8.6, 1H), 3.85-3.73 (m, 2H), 3.64-3.50 (m, 2H), 3.40 (dd, J=11.3, 6.7, 1H), 3.30 (dd, J=10.9, 2.4, 1H), 3.02-2.91 (m, 1H), 2.66 (dd, J=14.5, 8.2, 1H), 2.13 (ddd, J=17.8, 12.6, 8.2, 1H), 1.80-1.71 (m, 1H), 1.68 (dt, J=13.4, 8.5, 1H), 1.37 (ddd, J=13.8, 10.0, 5.1, 1H), 1.33-1.22 (m, 1H), 1.19 (s, 3H); MS (ESI+) m/z 394 (M+H)$^+$.

Example 26

(3aR,4R,6aS)-4-methyl-2-[6-(trifluoromethyl)pyridin-2-yl]octahydrocyclopenta[c]pyrrol-4-amine (3aR,4R,6aS)—N-Benzyl-4-methyl-2-[6-(trifluoromethyl)pyridin-2-yl]octahydrocyclopenta[c]pyrrol-4-amine (30 mg, 0.080 mmol) from Example 21 and isopropanol (14 mL) were added to 20% Pd(OH)$_2$—C, wet (6.0 mg, 0.043 mmol) in a 50 mL pressure bottle and stirred for 90 minutes under 30 psi hydrogen gas at 50° C. The mixture was filtered through a nylon membrane and the solvent was removed in vacuo. The crude material was purified by silica gel chromatography using 1-10% methanol (2 N ammonia)/dichloromethane as eluent to give the title compound: $^1$H NMR (500 MHz, pyridine-$d_5$) δ ppm 7.54-7.46 (m, 1H), 6.97 (d, J=7.2, 1H), 6.52 (d, J=8.6, 1H), 3.75 (dd, J=11.3, 5.2, 1H), 3.56 (dd, J=10.3, 8.4, 1H), 3.52-3.43 (m, 1H), 3.36 (dd, J=10.5, 3.9, 1H), 2.72-2.62 (m, 1H), 2.31 (td, J=8.7, 5.3, 1H), 1.92-1.81 (m, 1H), 1.77-1.68 (m, 1H), 1.60-1.35 (br m, 2H), 1.54-1.42 (m, 2H), 1.16 (s, 3H); MS (ESI+) m/z 286 (M+H)$^+$.

Example 27

(3aR,4S,6aS)-4-methyl-2-[6-(trifluoromethyl)pyridin-2-yl]octahydrocyclopenta[c]pyrrol-4-amine The title compound was prepared by substituting (3aR,4S,6aS)—N-benzyl-4-methyl-2-[6-(trifluoromethyl)pyridin-2-yl]octahydrocyclopenta[c]pyrrol-4-amine (Example 20) for (3aR,4R,6aS)—N-benzyl-4-methyl-2-[6-(trifluoromethyl)pyridin-2-yl]octahydrocyclopenta[c]pyrrol-4-amine in the procedure that describes the preparation of Example 26: $^1$H NMR (500 MHz, pyridine-$d_5$) δ ppm 7.57-7.51 (m, 1H), 6.99 (d, J=7.2, 1H), 6.53 (d, J=8.6, 1H), 3.61-3.48 (m, 2H), 3.33-3.22 (m, 2H), 2.99 (dtdd, J=10.3, 7.7, 5.1, 2.8, 1H), 2.41 (dd, J=16.0, 7.9, 1H), 2.19 (ddd, J=18.4, 13.3, 8.6, 1H), 1.77-1.68 (m, 1H), 1.67-1.43 (m, 2H), 1.53-1.45 (m, 1H), 1.34 (ddd, J=13.6, 9.1, 4.5, 1H), 1.15 (s, 3H); MS (ESI+) m/z 286 (M+H)$^+$.

Example 28

(3aR,4R,6aS)-2-benzyloctahydrocyclopenta[c]pyrrol-4-ol

A mixture of (3aR,6aS)-2-benzylhexahydrocyclopenta[c]pyrrol-4(5H)-one (1.462 g, 6.79 mmol) in methanol (20 mL)

was cooled in a dry ice/acetone bath to −40° C. Sodium borohydride (0.514 g, 13.58 mmol) was added in portions over 5 minutes. The reaction allowed to warm to room temperature overnight, then it was quenched with saturated aqueous ammonium chloride, diluted with water, and extracted with 3×150 mL of ethyl acetate. The combined extracts were dried ($Na_2SO_4$) and the solvent was removed in vacuo to give the title compound: $^1$H NMR (300 MHz, $CDCl_3$) δ ppm 7.45-7.38 (m, 2H), 7.34 (dd, J=10.2, 4.7, 2H), 7.30-7.24 (m, 1H), 5.63 (s, 1H), 4.30 (dd, J=11.4, 6.2, 1H), 3.54 (q, J=13.0, 2H), 3.17 (dd, J=9.3, 3.3, 1H), 2.57 (dtd, J=10.0, 7.1, 3.2, 1H), 2.48 (dtt, J=17.5, 8.7, 4.3, 1H), 2.44-2.38 (m, 2H), 2.31 (dd, J=9.2, 7.4, 1H), 2.04-1.96 (m, 1H), 1.76-1.61 (m, 2H), 1.47-1.40 (m, 1H); MS (ESI+) m/z 217 (M+H)$^+$.

Example 29

(3aR,4R,6aS)-octahydrocyclopenta[c]pyrrol-4-ol (3aR,4R,6aS)-2-Benzyloctahydrocyclopenta[c]pyrrol-4-ol (2.88 g, 13.25 mmol) from Example 28 and ethanol (40 mL) were added to 20% $Pd(OH)_2$—C, wet (0.576 g, 4.10 mmol) in a 250 mL stainless steel pressure bottle and stirred for 2 hours at 30 psi hydrogen gas at 50° C. The mixture was filtered through a nylon membrane, and the solvent was removed in vacuo to give the title compound: $^1$H NMR (500 MHz, pyridine-$d_5$) δ ppm 4.82 (s, 4H), 4.37 (dd, J=10.5, 4.8, 1H), 3.52 (dd, J=10.8, 1.7, 1H), 2.96-2.86 (m, 1H), 2.76 (dd, J=10.8, 6.9, 1H), 2.71 (dd, J=10.8, 1.8, 1H), 2.56-2.45 (m, 2H), 1.89 (td, J=11.7, 5.3, 1H), 1.80 (ddd, J=12.5, 10.3, 6.8, 1H), 1.66-1.58 (m, 1H), 1.50-1.42 (m, 1H); MS (ESI+) m/z 128 (M+H)$^+$.

Example 30

(3aR,4R,6aS)-2-[6-(trifluoromethyl)pyridin-2-yl]octahydrocyclopenta[c]pyrrol-4-ol (3aR,4R,6aS)-Octahydrocyclopenta[c]pyrrol-4-ol (1.65 g, 12.97 mmol) from Example 29, 2-bromo-6-(trifluoromethyl)pyridine (3.66 g, 16.22 mmol) and triethylamine (7.23 mL, 51.9 mmol) were combined in ethanol (7.23 mL). The reaction was heated at 80° C. for 24 hours and the solvent was concentrated in vacuo. The resulting residue was purified by silica gel chromatography using 0-40% ethyl acetate/hexane as eluent to give the title compound and the title compound of Example 31: $^1$H NMR (500 MHz, pyridine-$d_5$) δ ppm 7.47 (t, J=7.9, 1H), 6.94 (d, J=7.2, 1H), 6.53 (d, J=8.6, 1H), 6.38 (d, J=4.1, 1H), 4.47-4.38 (m, 1H), 4.12 (dd, J=11.0, 4.3, 1H), 3.70-3.63 (m, 1H), 3.53 (t, J=10.0, 1H), 3.38 (dd, J=10.4, 4.6, 1H), 2.80-2.73 (m, 1H), 2.72-2.64 (m, 1H), 1.97-1.74 (m, 3H), 1.64-1.56 (m, 1H); MS (ESI+) m/z 273 (M+H)$^+$.

Example 31

(3aR,4S,6aS)-2-[6-(trifluoromethyl)pyridin-2-yl]octahydrocyclopenta[c]pyrrol-4-ol The title compound was isolated from the reaction described in Example 30: $^1$H NMR (500 MHz, pyridine-$d_5$) δ ppm 7.55-7.48 (m, 1H), 6.99 (d, J=7.2, 1H), 6.53 (d, J=8.6, 1H), 6.29 (d, J=3.8, 1H), 4.35-4.25 (m, 1H), 3.57 (ddd, J=18.8, 10.9, 8.4, 2H), 3.44 (dd, J=11.1, 4.5, 1H), 3.27 (dd, J=10.7, 3.9, 1H), 2.88 (dqd, J=21.3, 8.4, 4.1, 2H), 2.18 (ddd, J=16.0, 13.0, 8.0, 1H), 1.99 (dtd, J=13.0, 7.8, 5.3, 1H), 1.92-1.79 (m, 1H), 1.48-1.35 (m, 1H); MS (ESI+) m/z 273 (M+H)$^+$.

Example 32

(3aR,6aS)-2-[6-(trifluoromethyl)pyridin-2-yl]hexahydrocyclopenta[c]pyrrol-4(1H)-one Dess-Martin periodinane (2.181 g, 5.14 mmol) was added to a solution of (3aR,4R,6aS)-2-[6-(trifluoromethyl)pyridin-2-yl]octahydrocyclopenta[c]pyrrol-4-ol (1 g, 3.67 mmol) from Example 30 in dichloromethane (24.49 mL). The mixture was stirred for 7 hours and then quenched with 1 N sodium thiosulfate (18 mL) and saturated $NaHCO_3$ solution (12 mL). The mixture was stirred for 1 hour. The organic layer was separated, and concentrated. The crude product was purified by silica gel chromatography using 100% dichloromethane as eluent to give the title compound: $^1$H NMR (500 MHz, pyridine-$d_5$) δ ppm 7.51 (t, J=7.9, 1H), 6.99 (d, J=7.3, 1H), 6.48 (d, J=8.6, 1H), 3.84 (dd, J=10.7, 2.8, 1H), 3.65 (dd, J=10.9, 8.6, 1H), 3.52 (dd, J=10.6, 8.7, 1H), 3.17 (dd, J=11.1, 6.3, 1H), 3.00-2.89 (m, 1H), 2.83 (td, J=8.4, 2.9, 1H), 2.39-2.21 (m, 2H), 1.96 (dtd, J=13.4, 8.9, 6.9, 1H), 1.75-1.62 (m, 1H); MS (ESI+) m/z 271 (M+H)$^+$.

Example 33

(3aR,4R,6aS)-4-methyl-2-[6-(trifluoromethyl)pyridin-2-yl]octahydrocyclopenta[c]pyrrol-4-ol Methylmagnesium iodide in ether (0.302 mL, 0.907 mmol) was added to (3aR,6aS)-2-[6-(trifluoromethyl)pyridin-2-yl]hexahydrocyclopenta[c]pyrrol-4(1H)-one (70 mg, 0.259 mmol) from Example 32 in ether (0.1 mL) at 25° C., and the reaction mixture was stirred for 1 hour. The reaction was quenched with saturated aqueous ammonium chloride solution, and the mixture was extracted with ethyl acetate. The combined organic washes were purified by silica gel chromatography using 0-30% ethyl acetate/hexane as eluent to give the title compound: $^1$H NMR (500 MHz, pyridine-$d_5$) δ ppm 7.46 (t, J=7.9, 1H), 6.93 (d, J=7.2, 1H), 6.50 (d, J=8.6, 1H), 5.92 (s, 1H), 4.03 (dd, J=11.1, 3.7, 1H), 3.69 (t, J=9.4, 1H), 3.61-3.50 (m, 1H), 3.43 (dd, J=10.0, 5.7, 1H), 2.83-2.69 (m, 1H), 2.46 (td, J=9.0, 3.9, 1H), 2.14-2.02 (m, 1H), 1.90 (dq, J=11.6, 8.4, 1H), 1.79-1.62 (m, 2H), 1.42 (s, 3H); MS (ESI+) m/z 287 (M+H)$^+$.

Example 34

(3aR,4S,6aS)-4-isopropyl-2-[6-(trifluoromethyl)pyridin-2-yl]octahydrocyclopenta[c]pyrrol-4-ol The title compound was prepared by substituting isopropylmagnesium bromide for methylmagnesium iodide in the procedure that describes the preparation of Example 33: $^1$H NMR (500 MHz, pyridine-$d_5$) δ ppm 7.45 (t, J=7.9, 1H), 6.92 (d, J=7.2, 1H), 6.50 (d, J=8.6, 1H), 5.36 (s, 1H), 4.06 (dd, J=10.8, 3.6, 1H), 3.70 (t, J=9.5, 1H), 3.53 (t, J=9.9, 1H), 3.43 (dd, J=10.2, 6.1, 1H), 2.84-2.69 (m, 1H), 2.62 (td, J=9.5, 3.8, 1H), 2.01 (ddd, J=12.6, 6.9, 2.5, 1H), 1.94-1.64 (m, 4H), 1.06 (dd, J=6.7, 5.3, 6H); MS (ESI+) m/z 315 (M+H)$^+$.

Example 35

(3aR,4R,6aS)-4-phenyl-2-[6-(trifluoromethyl)pyridin-2-yl]octahydrocyclopenta[c]pyrrol-4-ol Phenylmagnesium bromide in tetrahydrofuran (0.266 mL, 0.266 mmol) was added to (3aR,6aS)-2-[6-(trifluoromethyl)pyridin-2-yl]hexahydrocyclopenta[c]pyrrol-4(1H)-one (60 mg, 0.222 mmol) from Example 32 in tetrahydrofuran (1 mL) at −40° C., and the reaction mixture was allowed to warm to −10° C. in 20 minutes. The reaction was quenched with saturated aqueous ammonium chloride solution, and the mixture was extracted with ethyl acetate. The combined organic washes were purified by silica gel chromatography using 0-40% ethyl acetate/hexane as eluent to give the title compound: $^1$H NMR (500 MHz, pyridine-$d_5$) δ ppm 7.78 (dt, J=8.2, 1.6, 2H), 7.45 (t, J=7.7, 3H), 7.37-7.27 (m, 1H), 6.90 (d, J=7.2, 1H), 6.70 (d, J=0.5, 1H), 6.46 (d, J=8.6, 1H), 4.02-3.94 (m, 1H), 3.92-3.82 (m, 1H), 3.62-3.42 (m, 2H), 3.07 (td, J=9.3, 2.8, 1H), 3.02-2.92 (m, 1H), 2.38-2.22 (m, 2H), 2.17-1.98 (m, 2H); MS (ESI+) m/z 349 (M+H)$^+$.

Example 36

(3aR,4R,6aS)-4-(3-fluorophenyl)-2-[6-(trifluoromethyl)pyridin-2-yl]octahydrocyclopenta[c]pyrrol-4-ol The title compound was prepared by substituting (3-fluorophenyl)magnesium bromide for phenylmagnesium bromide in the procedure that describes the preparation of Example 35: $^1$H NMR (500 MHz, pyridine-$d_5$) δ ppm 7.69-7.62 (m, 1H), 7.53 (d, J=7.9, 1H), 7.45 (t, J=7.9, 1H), 7.40 (td, J=8.0, 6.2, 1H), 7.14-7.07 (m, 1H), 6.91 (d, J=7.2, 1H), 6.85 (s, 1H), 6.48 (d, J=8.6, 1H), 3.95 (d, J=10.9, 1H), 3.90-3.83 (m, 1H), 3.58-3.51 (m, 1H), 3.48 (td, J=9.3, 3.4, 1H), 3.08-2.93 (m, 2H), 2.34-2.21 (m, 2H), 2.16-2.07 (m, 1H), 2.06-1.98 (m, 1H); MS (ESI+) m/z 367 (M+H)$^+$.

Example 37

(3aR,4S,6aS)-4-(3,4-difluorobenzyl)-2-[6-(trifluoromethyl)pyridin-2-yl]octahydrocyclopenta[c]pyrrol-4-ol The title compound was prepared by substituting (3,4-difluorobenzyl)magnesium bromide for methyl magnesium iodide in the procedure that describes the preparation of Example 33: $^1$H NMR (500 MHz, pyridine-$d_5$) δ ppm 7.48-7.42 (m, 1H), 7.38 (ddd, J=11.8, 7.9, 2.0, 1H), 7.20-7.16 (m, 1H), 7.13 (d, J=4.2, 1H), 6.92 (d, J=7.2, 1H), 6.47 (d, J=8.6, 1H), 6.03 (s, 1H), 3.93 (dd, J=11.2, 3.4, 1H), 3.72 (t, J=9.4, 1H), 3.51 (t, J=9.9, 1H), 3.42 (dd, J=10.1, 5.9, 1H), 2.95 (d, J=13.5, 1H), 2.89-2.76 (m, 2H), 2.61 (td, J=9.1, 3.8, 1H), 1.98-1.88 (m, 2H), 1.82-1.67 (m, 2H); MS (ESI+) m/z 399 (M+H)$^+$.

Example 38

(3aR,4S,6aS)-4-[1-(3-fluorophenyl)ethyl]-2-[6-(trifluoromethyl)pyridin-2-yl]octahydrocyclopenta[c]pyrrol-4-ol The title compound was prepared by substituting (3-fluorophenethyl)magnesium bromide for phenyl magnesium bromide in the procedure that describes the preparation of Example 35: $^1$H NMR (500 MHz, pyridine-$d_5$) δ ppm 7.48 (t, J=7.9, 1H), 7.36-7.24 (m, 1H), 7.13-6.98 (m, 3H), 6.93 (d, J=7.2, 1H), 6.53 (d, J=8.6, 1H), 5.93 (s, 1H), 4.10 (dd, J=11.0, 3.4, 1H), 3.72 (t, J=9.4, 1H), 3.60 (t, J=9.9, 1H), 3.45 (dd, J=10.0, 6.0, 1H), 3.06-2.87 (m, 2H), 2.87-2.75 (m, 1H), 2.60 (td, J=9.1, 3.7, 1H), 2.13 (td, J=11.2, 7.7, 1H), 2.06-1.85 (m, 3H), 1.85-1.70 (m, 2H); MS (ESI+) m/z 395 (M+H)$^+$.

Example 39

(3aR,4R,6aS)-2-[6-(trifluoromethyl)pyridin-2-yl]octahydrocyclopenta[c]pyrrol-4-yl 4-bromobenzenesulfonate To a solution of (3aR,4R,6aS)-2-[6-(trifluoromethyl)pyridin-2-yl]octahydrocyclopenta[c]pyrrol-4-ol (3.2 g, 11.75 mmol) from Example 30 in dichloromethane (15 mL) was added triethylamine (4.10 mL, 29.4 mmol) followed by 1-methylimidazole (0.281 mL, 3.53 mmol). The solution was cooled to 0° C. and 4-bromobenzene-1-sulfonyl chloride (4.50 g, 17.63 mmol) was added. The solution was warmed to room temperature (solution turned cloudy) and stirred for 16 hours. The reaction mixture was diluted with dichloromethane (12 mL) and washed with aqueous hydrogen chloride (0.1 N, 2×10 mL) and water (10 mL). The organic phase was dried over sodium sulfate and concentrated. The crude material was purified by silica gel chromatography using 0-60% dichloromethane/hexane as eluent to give the title compound: $^1$H NMR (500 MHz, pyridine-$d_5$) δ ppm 7.99-7.90 (m, 2H), 7.77-7.67 (m, 2H), 7.51 (t, J=7.9, 1H), 6.99 (d, J=7.3, 1H), 6.45 (d, J=8.6, 1H), 5.17 (q, J=6.1, 1H), 3.69 (dd, J=11.4, 4.6, 1H), 3.57-3.47 (m, 1H), 3.37 (dd, J=11.4, 8.9, 1H), 3.23 (dd, J=10.7, 4.5, 1H), 2.90-2.78 (m, 1H), 2.67-2.54 (m, 1H), 2.02-1.88 (m, 1H), 1.80 (dq, J=8.2, 6.0, 1H), 1.70 (dtd, J=13.5, 8.6, 7.0, 1H), 1.51-1.37 (m, 1H); MS (ESI+) m/z 491 (M+H)$^+$.

Example 40

(3aR,4S,6aS)-4-methoxy-2-[6-(trifluoromethyl)pyridin-2-yl]octahydrocyclopenta[c]pyrrole (3aR,4R,6aS)-2-[6-(Trifluoromethyl)pyridin-2-yl]octahydrocyclopenta[c]pyrrol-4-yl 4-bromobenzenesulfonate (100 mg, 0.204 mmol) from Example 39 was heated at 85° C. for 3 days in methanol (0.3 mL) to give a colorless solution. The methanol was removed in vacuo, and the crude material was purified by silica gel chromatography using 100% dichloromethane as eluent to give the title compound: $^1$H NMR (500 MHz, pyridine-$d_5$) δ ppm 7.57-7.53 (m, 1H), 7.01 (d, J=7.3, 1H), 6.54 (d, J=8.6, 1H), 3.58 (dd, J=11.0, 8.8, 1H), 3.52 (dd, J=7.1, 4.8, 1H), 3.47 (dd, J=10.7, 7.8, 1H), 3.28 (dd, J=11.1, 4.8, 1H), 3.24-3.18 (m, 4H), 2.81-2.64 (m, 2H), 1.93 (dq, J=12.9, 7.9, 1H), 1.80 (dtd, J=13.2, 7.8, 5.4, 1H), 1.68 (ddd, J=17.7, 11.3, 6.7, 1H), 1.38-1.25 (m, 1H); MS (ESI+) m/z 287 (M+H)$^+$.

Example 41

(3aR,4S,6aS)-4-ethoxy-2-[6-(trifluoromethyl)pyridin-2-yl]octahydrocyclopenta[c]pyrrole The title compound was prepared by substituting ethanol for methanol in the procedure that describes the preparation of Example 40: $^1$H NMR (500 MHz, pyridine-$d_5$) δ ppm 7.56 (d, J=8.0, 1H), 7.00 (d, J=7.2, 1H), 6.54 (d, J=8.6, 1H), 3.64 (dd, J=7.9, 4.7, 1H), 3.59 (dd, J=11.0, 8.9, 1H), 3.47 (dd, J=10.7, 7.9, 1H), 3.41-3.35 (m, 2H), 3.32 (dd, J=11.1, 4.7, 1H), 3.21 (dd, J=10.7, 3.8, 1H), 2.81-2.64 (m, 2H), 1.96 (dq, J=12.8, 7.8, 1H), 1.84 (dtd, J=13.1, 7.5, 5.5, 1H), 1.68 (td, J=13.1, 6.9, 1H), 1.32 (ddd, J=12.8, 7.5, 6.1, 1H), 1.16 (t, J=7.0, 3H); MS (ESI+) m/z 301 (M+H)$^+$.

Example 42

(3aR,4S,6aS)-4-isopropoxy-2-[6-(trifluoromethyl)pyridin-2-yl]octahydrocyclopenta[c]pyrrole The title compound was prepared by substituting isopropanol for methanol in the procedure that describes the preparation of Example 40: $^1$H NMR (500 MHz, pyridine-$d_5$) δ ppm 7.55 (d, J=7.9, 1H), 7.01 (d, J=7.3, 1H), 6.56 (d, J=8.6, 1H), 3.77 (dd, J=8.3, 4.8, 1H), 3.63-3.52 (m, 2H), 3.48 (dd, J=10.7, 8.1, 1H), 3.34 (dd, J=11.1, 4.9, 1H), 3.22 (dd, J=10.7, 3.9, 1H), 2.80-2.72 (m, 1H), 2.71-2.64 (m, 1H), 1.98 (dq, J=12.8, 7.8, 1H), 1.91-1.78 (m, 1H), 1.64 (td, J=13.0, 7.0, 1H), 1.32 (td, J=12.8, 6.2, 1H), 1.12 (dd, J=6.1, 1.7, 6H); MS (ESI+) m/z 315 (M+H)$^+$.

Example 43

(3aR,4S,6aS)-4-tert-butoxy-2-[6-(trifluoromethyl)pyridin-2-yl]octahydrocyclopenta[c]pyrrole The title compound was prepared by substituting tert-butanol for methanol in the procedure that describes the preparation of Example 40: $^1$H NMR (400 MHz, pyridine-$d_5$) δ ppm 7.55 (d, J=7.9, 1H), 7.01 (d, J=7.2, 1H), 6.57 (d, J=8.6, 1H), 3.85 (dd, J=9.4, 5.5, 1H), 3.61 (dd, J=11.0, 8.6, 1H), 3.46 (ddd, J=15.8, 10.9, 6.4, 2H), 3.22 (dd, J=10.8, 4.2, 1H), 2.78-2.68 (m, 1H), 2.62 (dq, J=12.9, 4.2, 1H), 2.06-1.83 (m, 2H), 1.67-1.52 (m, 1H), 1.32 (ddd, J=11.0, 7.5, 5.5, 1H), 1.17 (s, 9H); MS (ESI+) m/z 329 (M+H)$^+$.

Example 44

(3aR,4S,6aS)-4-(3-fluorophenoxy)-2-[6-(trifluoromethyl)pyridin-2-yl]octahydrocyclopenta[c]pyrrole To (3aR,4R,6aS)-2-[6-(trifluoromethyl)pyridin-2-yl]octahydrocyclopenta[c]pyrrol-4-ol (90 mg, 0.331 mmol) from Example 30 and triphenylphosphine (173 mg, 0.661 mmol) was added tetrahydrofuran (1.150 mL) and 3-fluorophenol (0.059 mL, 0.661 mmol) followed by dropwise addition of diisopropyl azodicarboxylate (DIAD, 0.129 mL, 0.661 mmol). The reaction mixture was stirred for 7 hours and then quenched with saturated aqueous ammonium chloride solution and extracted with ethyl acetate. The combined organic washes were purified by silica gel chromatography using 0-6% ethyl acetate/hexane as eluent to give the title compound: $^1$H NMR (500 MHz, pyridine-$d_5$) δ ppm 7.56 (d, J=8.0, 1H), 7.31 (dd, J=15.3, 8.2, 1H), 7.02 (d, J=7.3, 1H), 6.92 (dt, J=11.2, 2.4, 1H), 6.89-6.77 (m, 2H), 6.56 (d, J=8.6, 1H), 4.65 (d, J=2.2, 1H), 3.69 (dd, J=11.0, 8.9, 1H), 3.52 (dd, J=10.7, 7.6, 1H), 3.41 (dd, J=11.3, 4.7, 1H), 3.25 (dd, J=10.7, 3.0, 1H), 2.93-2.78 (m, 2H), 2.10-1.94 (m, 2H), 1.82 (dt, J=13.8, 7.1, 1H), 1.50-1.37 (m, 1H); MS (ESI+) m/z 367 (M+H)$^+$.

Example 45

(3aR,4S,6aS)-4-[(3-fluorobenzyl)oxy]-2-[6-(trifluoromethyl)pyridin-2-yl]octahydrocyclopenta[c]pyrrole The title compound was prepared by substituting (3-fluorophenyl)methanol for methanol in the procedure that describes the preparation of Example 40: $^1$H NMR (500 MHz, pyridine-$d_5$) δ ppm 7.55 (d, J=7.9, 1H), 7.35 (td, J=7.9, 6.0, 1H), 7.30 (d, J=9.9, 1H), 7.23 (d, J=7.9, 1H), 7.10 (td, J=8.6, 2.6, 1H), 7.01 (d, J=7.3, 1H), 6.55 (d, J=8.6, 1H), 4.50 (s, 2H), 3.85-3.76 (m, 1H), 3.62 (dd, J=10.8, 8.8, 1H), 3.49 (dd, J=10.5, 7.6, 1H), 3.32 (dd, J=11.1, 4.0, 1H), 3.24 (dd, J=10.7, 2.6, 1H), 2.79 (dd, J=14.2, 5.8, 2H), 2.07-1.94 (m, 1H), 1.87 (dtd, J=13.2, 7.7, 5.4, 1H), 1.77 (ddd, J=13.3, 8.8, 5.7, 1H), 1.36 (tdd, J=7.7, 5.8, 4.1, 1H); MS (ESI+) m/z 381 (M+H)$^+$.

Example 46

(3aR,4S,6aS)-4-[1-(3-fluorophenyl)ethoxy]-2-[6-(trifluoromethyl)pyridin-2-yl]octahydrocyclopenta[c]pyrrole The title compound was prepared by substituting 2-(3-fluorophenyl)ethanol for methanol in the procedure that describes the preparation of Example 40: $^1$H NMR (500 MHz, pyridine-$d_5$) δ ppm 7.57-7.52 (m, 1H), 7.31 (td, J=7.9, 6.3, 1H), 7.19-7.14 (m, 1H), 7.11 (d, J=7.6, 1H), 7.05 (td, J=8.5, 2.5, 1H), 7.00 (d, J=7.2, 1H), 6.53 (d, J=8.6, 1H), 3.66 (dd, J=7.0, 5.1, 1H), 3.62-3.58 (m, 2H), 3.58-3.53 (m, 1H), 3.46 (dd, J=10.7, 7.8, 1H), 3.29 (dd, J=11.2, 4.6, 1H), 3.20 (dd, J=10.8, 3.5, 1H), 2.89 (d, J=6.7, 2H), 2.76-2.64 (m, 2H), 1.92 (dq, J=12.9, 7.8, 1H), 1.81 (dtd, J=13.2, 7.7, 5.4, 1H), 1.67 (ddd, J=17.9, 11.4, 6.7, 1H), 1.35-1.26 (m, 1H); MS (ESI+) m/z 395 (M+H)$^+$.

Example 47

(3aR,4R,6aS)-2-benzyl-4-phenyloctahydrocyclopenta[c]pyrrol-4-ol

The title compound was prepared by substituting (3aR,6aS)-2-[6-(trifluoromethyl)pyridin-2-yl]hexahydrocyclopenta[c]pyrrol-4(1H)-one from Example 32 with (3aR,6aS)-2-benzylhexahydrocyclopenta[c]pyrrol-4(5H)-one in the procedure that describes the preparation of Example 35: $^1$H NMR (500 MHz, pyridine-$d_5$) δ ppm 7.77 (dd, J=8.3, 1.1, 2H), 7.37 (tt, J=15.0, 7.7, 6H), 7.31-7.25 (m, 2H), 6.26 (s, 1H), 3.60 (d, J=12.9, 1H), 3.46 (d, J=12.9, 1H), 3.03 (d, J=9.4, 1H), 2.74-2.58 (m, 3H), 2.13 (dd, J=8.9, 7.5, 1H), 2.06-1.99 (m, 3H), 1.97 (dd, J=9.4, 6.0, 1H), 1.71-1.60 (m, 1H); MS (ESI+) m/z 294 (M+H)$^+$.

Example 48

(3aR,4S,6aS)-2-benzyl-4-(3-fluorophenoxy)octahydrocyclopenta[c]pyrrole

The title compound was prepared by substituting (3aR,4R,6aS)-2-benzyloctahydrocyclopenta[c]pyrrol-4-ol from Example 28 for (3aR,4R,6aS)-2-[6-(trifluoromethyl)pyridin-2-yl]octahydrocyclopenta[c]pyrrol-4-ol in the procedure that describes the preparation of Example 44: $^1$H NMR (500 MHz, pyridine-$d_5$) δ ppm 7.45 (d, J=7.2, 2H), 7.40 (dd, J=10.3, 4.8, 2H), 7.34-7.23 (m, 2H), 6.88 (dt, J=11.3, 2.4, 1H), 6.83-6.75 (m, 2H), 4.58-4.49 (m, 1H), 3.51 (s, 2H), 2.74-2.62 (m, 2H), 2.55-2.49 (m, 1H), 2.49-2.40 (m, 2H), 2.29 (dd, J=9.0, 3.7, 1H), 2.09-1.93 (m, 2H), 1.86-1.77 (m, 1H), 1.44 (ddd, J=12.4, 6.8, 3.3, 1H); MS (ESI+) m/z 312 (M+H)$^+$.

Example 49

(3aS,6aS)-4-methylene-2-[6-(trifluoromethyl)pyridin-2-yl]octahydrocyclopenta[c]pyrrole The title compound was prepared by substituting (3aR,6aS)-2-[6-(trifluoromethyl)pyridin-2-yl]hexahydrocyclopenta[c]pyrrol-4(1H)-one from Example 32 for (3aR,6aS)-2-benzylhexahydrocyclopenta[c]pyrrol-4(5H)-one in the procedure that describes the preparation of Example 1: ¹H NMR (500 MHz, pyridine-d₅) δ ppm 7.54-7.49 (m, 1H), 6.98 (d, J=7.2, 1H), 6.49 (d, J=8.6, 1H), 4.95-4.89 (m, 2H), 3.68 (dd, J=10.3, 8.7, 1H), 3.52 (dd, J=10.7, 8.3, 1H), 3.44 (dd, J=10.7, 4.3, 1H), 3.17 (dd, J=10.7, 5.1, 1H), 3.08-3.00 (m, 1H), 2.66 (tt, J=13.1, 6.6, 1H), 2.44-2.35 (m, 1H), 2.31-2.22 (m, 1H), 1.71 (ddt, J=13.0, 8.4, 7.1, 1H), 1.43 (ddd, J=13.1, 8.1, 6.0, 1H); MS (ESI+) m/z 269 (M+H)⁺.

Example 50

(3aR,4S,6aS)-4-(1H-imidazol-1-yl)-2-[6-(trifluoromethyl)pyridin-2-yl]octahydrocyclopenta[c]pyrrole A 4 mL vial was charged with (3aR,4R,6aS)-2-[6-(trifluoromethyl)pyridin-2-yl]octahydrocyclopenta[c]pyrrol-4-yl 4-bromobenzenesulfonate (100 mg, 0.204 mmol) from Example 39 and 1H-imidazole (55.4 mg, 0.814 mmol) in toluene (0.5 mL). The reaction was heated at 90° C. for 24 hours, and then the reaction mixture was concentrated. The residue was purified by silica gel chromatography using 0-4% methanol (2 N ammonia)/dichloromethane as eluent to give the title compound: ¹H NMR (400 MHz, pyridine-d₅) δ ppm 7.98 (s, 1H), 7.55 (d, J=8.1, 1H), 7.43 (s, 1H), 7.28 (t, J=1.2, 1H), 7.03 (d, J=7.3, 1H), 6.53 (d, J=8.6, 1H), 4.29 (dt, J=8.5, 6.6, 1H), 3.57-3.44 (m, 2H), 3.39 (dd, J=11.2, 7.2, 1H), 3.27 (dd, J=10.9, 4.2, 1H), 2.89-2.72 (m, 2H), 2.12 (dtd, J=11.3, 7.1, 3.8, 1H), 2.03-1.94 (m, 1H), 1.87 (ddd, J=17.3, 12.6, 8.6, 1H), 1.49-1.32 (m, 1H); MS (ESI+) m/z 323 (M+H)⁺.

Example 51

(3aR,4S,6aS)-4-(1H-pyrazol-1-yl)-2-[6-(trifluoromethyl)pyridin-2-yl]octahydrocyclopenta[c]pyrrole The title compound was prepared by substituting 1H-pyrazole for 1H-imidazole in the procedure that describes the preparation of Example 50: ¹H NMR (400 MHz, pyridine-d₅) δ ppm 7.79 (d, J=1.6, 1H), 7.72 (d, J=2.2, 1H), 7.57-7.51 (m, 1H), 7.01 (d, J=7.2, 1H), 6.51 (d, J=8.6, 1H), 6.38 (t, J=2.0, 1H), 4.52 (dd, J=14.2, 7.3, 1H), 3.59 (dd, J=11.2, 3.4, 1H), 3.47 (ddd, J=22.0, 11.0, 8.2, 2H), 3.27 (dd, J=10.9, 4.9, 1H), 3.18-3.05 (m, 1H), 2.94-2.77 (m, 1H), 2.18 (ddd, J=12.5, 8.3, 5.0, 2H), 2.07 (dtd, J=13.1, 8.0, 5.0, 1H), 1.42 (dtd, J=13.7, 8.0, 5.6, 1H); MS (ESI+) m/z 323 (M+H)⁺.

Example 52

(3aR,4S,6aS)-4-(4-chloro-1H-pyrazol-1-yl)-2-[6-(trifluoromethyl)pyridin-2-yl]octahydrocyclopenta[c]pyrrole The title compound was prepared by substituting 4-chloro-1H-pyrazole for 1H-imidazole in the procedure that describes the preparation of Example 50: ¹H NMR (500 MHz, pyridine-d₅) δ ppm 7.92 (s, 1H), 7.76 (s, 1H), 7.57-7.52 (m, 1H), 7.02 (d, J=7.3, 1H), 6.53 (d, J=8.6, 1H), 4.48 (dd, J=14.0, 7.1, 1H), 3.59 (dd, J=11.2, 3.4, 1H), 3.54-3.42 (m, 2H), 3.26 (dd, J=10.8, 4.8, 1H), 3.07 (ddd, J=11.6, 9.1, 3.5, 1H), 2.92-2.78 (m, 1H), 2.24-1.98 (m, 3H), 1.48-1.35 (m, 1H); MS (ESI+) m/z 357 (M+H)⁺.

Example 53

(3aR,4S,6aS)-4-[(2S)-pyrrolidin-2-ylmethoxy]-2-[6-(trifluoromethyl)pyridin-2-yl]octahydrocyclopenta[c]pyrrole Step 1: (S)-tert-Butyl 2-(43aR,4S,6aS)-2-(6-(trifluoromethyl)pyridin-2-yl)octahydrocyclopenta[c]pyrrol-4-yloxy)methyl)pyrrolidine-1-carboxylate was prepared by substituting (S)-tert-butyl 2-(hydroxymethyl)pyrrolidine-1-carboxylate for methanol in the procedure that describes the preparation of Example 40: ¹H NMR (400 MHz, pyridine-d₅) δ ppm 7.48 (t, J=7.9, 1H), 6.93 (d, J=7.3, 1H), 6.51 (d, J=8.6, 1H), 4.04-3.97 (m, 1H), 3.72 (dd, J=7.5, 4.7, 1H), 3.68-3.58 (m, 2H), 3.55-3.45 (m, 2H), 3.43-3.35 (m, 2H), 3.33 (dd, J=11.2, 4.7, 1H), 3.24 (dd, J=10.9, 3.8, 1H), 2.83-2.69 (m, 2H), 2.04-1.94 (m, 1H), 1.92-1.78 (m, 4H), 1.77-1.58 (m, 2H), 1.53 (s, 9H), 1.42-1.31 (m, 1H); MS (ESI+) m/z 456 (M+H)⁺.

Step 2: The title compound was prepared by combining (S)-tert-butyl 2-(((3aR,4S,6aS)-2-(6-(trifluoromethyl)pyridin-2-yl)octahydrocyclopenta[c]pyrrol-4-yloxy)methyl)pyrrolidine-1-carboxylate (20 mg, 0.044 mmol) from Step 1, and 4 N HCl in 1,4-dioxane (0.103 mL, 0.412 mmol) to give a colorless solution. The reaction was stirred at ambient temperature overnight and dried to give a white foam as the HCl salt. The compound was purified using a 12 g silica gel cartridge with a gradient of 1-10% methanol (2 N ammonia)/dichloromethane as eluent over 20 minutes to give the title compound: ¹H NMR (400 MHz, pyridine-d₅) δ ppm 7.54 (t, J=7.9, 1H), 7.00 (d, J=7.2, 1H), 6.54 (d, J=8.6, 1H), 3.73-3.68 (m, 1H), 3.59 (dd, J=11.0, 8.8, 1H), 3.48 (dd, J=10.7, 7.6, 1H), 3.43-3.35 (m, 3H), 3.32 (dd, J=11.3, 4.3, 1H), 3.22 (dd, J=10.8, 3.1, 1H), 3.00 (ddd, J=9.9, 7.2, 5.6, 1H), 2.90-2.82 (m, 1H), 2.75 (dd, J=9.0, 5.7, 2H), 2.03-1.91 (m, 1H), 1.88-1.55 (m, 6H), 1.51-1.40 (m, 1H), 1.37-1.28 (m, 1H); MS (ESI+) m/z 356 (M+H)⁺.

Example 54 tert-butyl (3aS,4S,6aS)-4-[3-fluorophenyl)carbamoyl]hexahydrocyclopenta[c]pyrrole-2(1H)-carboxylate The title compound was prepared by combining (3aS,4S,6aS)-2-(tert-butoxycarbonyl)octahydrocyclopenta[c]pyrrole-4-carboxylic acid (300 mg, 1.175 mmol) (available from WuXi AppTec), 3-fluoroaniline (0.124 ml, 1.293 mmol), and 1-hydroxybenzotriazole hydrate (198 mg, 1.293 mmol) in dichloromethane (1 mL) to give a colorless suspension. After 20 minutes, N¹-((ethylimino)methylene)-N³,N³-dimethylpropane-1,3-diamine (0.229 ml, 1.293 mmol) was added and the mixture became homogeneous. The reaction mixture was then stirred at ambient temperature for 18 hours. The reaction was diluted with 1 mL of dichloromethane and quenched with 2 mL of water. The layers were separated, and then the aqueous layer was extracted with 2×2 mL more dichloromethane, the solvent was removed in vacuo, and the crude material was applied to a 24 g silica gel cartridge and purified with 1-50% ethyl acetate/hexanes to give the title compound: ¹H NMR (500 MHz, pyridine-d₅) δ ppm 11.01 (s, 1H), 8.22-8.12 (m, 1H), 7.56 (s, 1H), 7.28 (dd, J=15.0, 8.1, 1H), 6.90 (td, J=8.4, 2.4, 1H), 3.62-3.29 (m, 3H), 3.16-3.00 (m, 2H), 2.82 (dd, J=14.7, 7.7, 1H), 2.73-2.58 (m, 1H), 2.13-1.86 (m, 3H), 1.51 (s, 9H), 1.29 (td, J=13.3, 7.7, 1H); MS (ESI−) m/z 347 (M−H)⁻.

Example 55

(3aS,4S,6aS)—N-(3-fluorophenyl)octahydrocyclopenta[c]pyrrole-4-carboxamide

The title compound was prepared by combining tert-butyl (3aS,4S,6aS)-4-[(3-fluorophenyl)carbamoyl]hexahydrocyclopenta[c]pyrrole-2(1H)-carboxylate (181 mg, 0.520 mmol) from Example 54 with 4 N HCl in 1,4-dioxane (2 mL, 8.00 mmol) to give a colorless solution. The reaction mixture was stirred at room temperature for 18 hours and dried to give a white foam as the HCl salt. The solid was neutralized with aqueous sodium bicarbonate and extracted with ethyl acetate to give the title compound: $^1$H NMR (500 MHz, pyridine-$d_5$) δ ppm 10.98-10.87 (m, 1H), 8.26-8.20 (m, 1H), 7.61 (ddd, J=5.7, 5.0, 0.9, 1H), 7.28 (tt, J=12.5, 8.0, 1H), 6.92-6.85 (m, 1H), 3.12-3.05 (m, 1H), 2.87-2.82 (m, 2H), 2.81-2.72 (m, 2H), 2.63-2.55 (m, 2H), 2.07-1.93 (m, 4H), 1.31-1.21 (m, 1H); MS (ESI+) m/z 249 (M+H)$^+$.

Example 56

(3aS,4S,6aS)—N-(3-fluorophenyl)-2-[6-(trifluoromethyl)pyridin-2-yl]octahydrocyclopenta[c]pyrrole-4-carboxamide The title compound was prepared by combining (3aS,4S,6aS)—N-(3-fluorophenyl)octahydrocyclopenta[c]pyrrole-4-carboxamide (98 mg, 0.395 mmol) from Example 55, 2-bromo-6-(trifluoromethyl)pyridine (125 mg, 0.553 mmol), and triethylamine (0.165 mL, 1.184 mmol) in ethanol (0.2 mL). The reaction mixture was heated at 80° C. for 72 hours. The reaction was quenched with water (1 mL) and the resulting brown oil was purified using a 12 g silica gel cartridge eluting with 1-100% ethyl acetate/hexanes over 20 minutes to give a solid. The solid was recrystallized from ethyl acetate/heptane (10%) to give the title compound: $^1$H NMR (400 MHz, pyridine-$d_5$) δ ppm 11.06 (s, 1H), 8.21 (dt, J=11.7, 2.2, 1H), 7.60-7.59 (m, 1H), 7.54-7.47 (m, 1H), 7.30 (td, J=8.2, 6.8, 1H), 6.98 (d, J=7.3, 1H), 6.91 (tdd, J=8.6, 2.6, 0.6, 1H), 6.41 (d, J=8.6, 1H), 3.46 (dd, J=10.3, 7.6, 3H), 3.23-3.14 (m, 1H), 3.06 (dd, J=10.8, 5.7, 1H), 2.90-2.72 (m, 2H), 2.22-2.12 (m, 1H), 2.12-1.95 (m, 2H), 1.39 (dtd, J=10.4, 8.0, 5.4, 1H); MS (ESI+) m/z 394 (M+H)$^+$.

Example 57

(3aR,4S,6aS)-4-[4-(4-chlorophenyl)-1H-imidazol-1-yl]-2-[6-(trifluoromethyl)pyridin-2-yl]octahydrocyclopenta[c]pyrrole The title compound was prepared by substituting 4-(4-chlorophenyl)-1H-imidazole for 1H-imidazole in the procedure that describes the preparation of Example 50: $^1$H NMR (500 MHz, pyridine-$d_5$) δ ppm 8.17-8.11 (m, 2H), 8.02 (d, J=1.2, 1H), 7.79 (d, J=1.3, 1H), 7.56 (t, 1H), 7.50-7.45 (m, 2H), 7.04 (d, J=7.3, 1H), 6.57 (d, J=8.6, 1H), 4.33 (dt, J=8.4, 6.8, 1H), 3.54 (ddd, J=18.9, 10.9, 5.2, 2H), 3.45 (dd, J=11.2, 7.3, 1H), 3.29 (dd, J=10.8, 4.5, 1H), 2.93-2.78 (m, 2H), 2.23-2.15 (m, 1H), 2.09-1.99 (m, 1H), 1.99-1.87 (m, 1H), 1.48-1.38 (m, 1H); MS (ESI+) m/z 433 (M+H)$^+$.

Example 58

(3aR,4S,6aS)-4-(4-phenyl-1H-imidazol-1-yl)-2-[6-(trifluoromethyl)pyridin-2-yl]octahydrocyclopenta[c]pyrrole The title compound was prepared by substituting 4-phenyl-1H-imidazole for 1H-imidazole in the procedure that describes the preparation of Example 50: $^1$H NMR (500 MHz, pyridine-$d_5$) δ ppm 8.26 (dt, J=7.9, 1.4, 2H), 8.01 (d, J=1.3, 1H), 7.79 (d, J=1.3, 1H), 7.56 (t, 1H), 7.50-7.45 (m, 2H), 7.33-7.26 (m, 1H), 7.03 (d, J=7.2, 1H), 6.56 (d, J=8.6, 1H), 4.32 (dt, J=8.4, 6.8, 1H), 3.57-3.49 (m, 2H), 3.43 (dd, J=11.2, 7.3, 1H), 3.29 (dd, J=10.8, 4.6, 1H), 2.92-2.77 (m, 2H), 2.21-2.12 (m, 1H), 2.06-1.99 (m, 1H), 1.93 (dq, J=12.8, 8.5, 1H), 1.48-1.38 (m, 1H); MS (ESI+) m/z 399 (M+H)$^+$.

Example 59

5-methyl-1-{(3aR,4S,6aS)-2-[6-(trifluoromethyl)pyridin-2-yl]octahydrocyclopenta[c]pyrrol-4-yl}-1H-benzimidazole and 6-methyl-1-{(3aR,4S,6aS)-2-[6-(trifluoromethyl)pyridin-2-yl]octahydrocyclopenta[c]pyrrol-4-yl}-1H-benzimidazole The title compounds were prepared by substituting 5-methyl-1H-benzo[d]imidazole for 1H-imidazole in the procedure that describes the preparation of Example 50: $^1$H NMR (500 MHz, pyridine-$d_5$) δ ppm 8.44 (2S, 1H), 8.05-7.89 (m, 1H), 7.60-7.56 (m, 1H), 7.51 (m, 1H), 7.25-7.21 (m, 1H), 7.04 (d, J=7.3, 1H), 6.56 (dd, J=8.6, 2.7, 1H), 4.67 (tt, J=11.9, 6.0, 1H), 3.57 (ddd, J=8.4, 7.9, 3.6, 2H), 3.48 (dt, J=11.2, 7.2, 1H), 3.36 (ddd, J=10.8, 8.6, 4.7, 1H), 3.17-3.04 (m, 1H), 2.90 (dt, J=8.6, 3.5, 1H), 2.47 (d, J=6.7, 3H), 2.26-2.17 (m, 1H), 2.13-2.02 (m, 2H), 1.57-1.45 (m, 1H); MS (ESI+) m/z 387 (M+H)$^+$.

Example 60

1-{(3aR,4S,6aS)-2-[6-(trifluoromethyl)pyridin-2-yl]octahydrocyclopenta[c]pyrrol-4-yl}-1H-benzimidazole The title compound was prepared by substituting 1H-benzo[d]imidazole for 1H-imidazole in the procedure that describes the preparation of Example 50: $^1$H NMR (500 MHz, pyridine-$d_5$) δ ppm 8.50 (s, 1H), 8.18-8.08 (m, 1H), 7.67-7.60 (m, 1H), 7.56 (s, 1H), 7.43-7.37 (m, 2H), 7.04 (d, J=7.3, 1H), 6.56 (d, J=8.6, 1H), 4.69 (dd, J=13.8, 7.0, 1H), 3.61-3.52 (m, 2H), 3.48 (dd, J=11.2, 7.8, 1H), 3.35 (dd, J=10.8, 4.7, 1H), 3.15-3.04 (m, 1H), 2.91 (dt, J=10.0, 4.0, 1H), 2.26-2.18 (m, 1H), 2.12-2.01 (m, 2H), 1.57-1.46 (m, 1H); MS (ESI+) m/z 373 (M+H)$^+$.

Example 61

(3aR,4S,6aS)-4-(2-methyl-1H-imidazol-1-yl)-2-[6-(trifluoromethyl)pyridin-2-yl]octahydrocyclopenta[c]pyrrole The title compound was prepared by substituting 2-methyl-1H-imidazole for 1H-imidazole in the procedure that describes the preparation of Example 50: $^1$H NMR (500 MHz, pyridine-$d_5$) δ ppm 7.60-7.55 (m, 1H), 7.30 (d, J=1.2, 1H), 7.18 (d, J=1.3, 1H), 7.03 (d, J=7.2, 1H), 6.56 (d, J=8.6, 1H), 4.32 (dd, J=13.4, 7.3, 1H), 3.55-3.42 (m, 3H), 3.31 (dd, J=10.8, 4.0, 1H), 2.86-2.76 (m, 2H), 2.42 (s, 3H), 2.16-2.09 (m, 1H), 2.05-1.96 (m, 1H), 1.77 (dq, J=13.0, 8.3, 1H), 1.43 (dtd, J=13.5, 8.3, 5.3, 1H); MS (ESI+) m/z 337 (M+H)$^+$.

Example 62

(3aR,4S,6aS)-4-(2-phenyl-1H-imidazol-1-yl)-2-[6-(trifluoromethyl)pyridin-2-yl]octahydrocyclopenta[c]pyrrole The title compound was prepared by substituting 2-phenyl-1H-imidazole for 1H-imidazole in the procedure that describes the preparation of Example 50: ¹H NMR (500 MHz, pyridine-d₅) δ ppm 7.79 (dt, J=8.0, 2.3, 2H), 7.54-7.49 (m, 2H), 7.44 (d, J=1.2, 1H), 7.39-7.35 (m, 2H), 7.33-7.28 (m, 1H), 6.99 (d, J=7.3, 1H), 6.41 (d, J=8.6, 1H), 4.67 (dd, J=13.2, 7.5, 1H), 3.45 (dd, J=10.8, 7.8, 1H), 3.37 (d, J=5.1, 2H), 3.25 (dd, J=10.8, 3.6, 1H), 2.92-2.81 (m, 2H), 2.24-2.16 (m, 1H), 2.02 (dtd, J=12.5, 8.2, 3.9, 1H), 1.92 (dq, J=13.0, 8.4, 1H), 1.41-1.31 (m, 1H); MS (ESI+) m/z 399 (M+H)⁺.

Example 63

(3aR,4S,6aS)-4-(4-methyl-1H-pyrazol-1-yl)-2-[6-(trifluoromethyl)pyridin-2-yl]octahydrocyclopenta[c]pyrrole The title compound was prepared by substituting 4-methyl-1H-pyrazole for 1H-imidazole in the procedure that describes the preparation of Example 50: ¹H NMR (400 MHz, pyridine-d₅) δ ppm 7.59 (s, 1H), 7.53 (t, J=8.0, 1H), 7.42 (s, 1H), 7.01 (d, J=7.3, 1H), 6.53 (d, J=8.6, 1H), 4.44 (q, J=7.2, 1H), 3.62 (dd, J=11.1, 3.3, 1H), 3.48 (ddd, J=13.8, 11.0, 8.3, 2H), 3.27 (dd, J=10.9, 4.8, 1H), 3.17-3.08 (m, 1H), 2.91-2.80 (m, 1H), 2.18 (dt, J=15.0, 4.3, 2H), 2.12-2.02 (m, 1H), 2.07 (s, 3H), 1.42 (dd, J=13.2, 5.5, 1H); MS (ESI+) m/z 337 (M+H)⁺.

Example 64

7-fluoro-1-{(3aR,4S,6aS)-2-[6-(trifluoromethyl)pyridin-2-yl]octahydrocyclopenta[c]pyrrol-4-yl}-1H-benzimidazole The title compound was prepared by substituting 4-fluoro-1H-benzo[d]imidazole for 1H-imidazole in the procedure that describes the preparation of Example 50: ¹H NMR (400 MHz, pyridine-d₅) δ ppm 8.51 (s, 1H), 7.86 (d, J=8.0, 1H), 7.60-7.54 (m, 1H), 7.27 (td, J=8.1, 5.0, 1H), 7.13 (ddd, J=11.9, 8.0, 0.5, 1H), 7.03 (d, J=7.2, 1H), 6.58 (d, J=8.6, 1H), 4.87 (dd, J=13.4, 6.5, 1H), 3.60-3.47 (m, 3H), 3.35 (dd, J=10.9, 4.5, 1H), 3.15-3.04 (m, 1H), 2.91 (dd, J=8.4, 4.8, 1H), 2.25 (dd, J=9.6, 5.6, 1H), 2.08 (ddd, J=13.2, 11.9, 6.2, 2H), 1.57-1.46 (m, 1H); MS (ESI+) m/z 391 (M+H)⁺.

Example 65

1-{(3aR,4S,6aS)-2-[6-(trifluoromethyl)pyridin-2-yl]octahydrocyclopenta[c]pyrrol-4-yl}-1H-indazole The title compound was prepared by substituting 1H-indazole for 1H-imidazole in the procedure that describes the preparation of Example 50: ¹H NMR (500 MHz, pyridine-d₅) δ ppm 8.31 (d, J=0.9, 1H), 7.99 (dd, J=8.7, 0.9, 1H), 7.81 (dt, J=8.4, 1.1, 1H), 7.57-7.53 (m, 1H), 7.41-7.36 (m, 1H), 7.20-7.15 (m, 1H), 7.02 (d, J=7.2, 1H), 6.55 (d, J=8.6, 1H), 4.82 (dd, J=14.2, 7.2, 1H), 3.67 (dd, J=11.1, 3.2, 1H), 3.56-3.46 (m, 2H), 3.35-3.24 (m, 2H), 2.97 (ddd, J=13.7, 6.8, 4.1, 1H), 2.43-2.28 (m, 2H), 2.23-2.13 (m, 1H), 1.55-1.44 (m, 1H); MS (ESI+) m/z 373 (M+H)⁺.

Example 66

(3aR,4S,6aS)-4-(3-methyl-1H-pyrazol-1-yl)-2-[6-(trifluoromethyl)pyridin-2-yl]octahydrocyclopenta[c]pyrrole The title compound was prepared by substituting 5-methyl-1H-pyrazole for 1H-imidazole in the procedure that describes the preparation of Example 50: ¹H NMR (500 MHz, pyridine-d₅) δ ppm 7.59 (d, J=2.2, 1H), 7.56-7.51 (m, 1H), 7.01 (d, J=7.2, 1H), 6.51 (d, J=8.6, 1H), 6.16 (d, J=2.1, 1H), 4.41 (dd, J=14.8, 7.0, 1H), 3.59 (dd, J=11.1, 3.2, 1H), 3.49 (dd, J=10.7, 8.6, 1H), 3.44 (dd, J=11.1, 7.8, 1H), 3.26 (dd, J=10.8, 5.0, 1H), 3.18-3.10 (m, 1H), 2.86 (ddd, J=10.6, 6.9, 4.2, 1H), 2.37 (s, 3H), 2.25-2.12 (m, 2H), 2.07 (ddd, J=16.8, 8.4, 4.1, 1H), 1.42 (ddd, J=10.4, 7.9, 5.4, 1H); MS (ESI+) m/z 337 (M+H)¹.

Example 67

(3aR,4S,6aS)-4-(4-methyl-1H-imidazol-1-yl)-2-[6-(trifluoromethyl)pyridin-2-yl]octahydrocyclopenta[c]pyrrole The title compound was prepared by substituting 4-methyl-1H-imidazole for 1H-imidazole in the procedure that describes the preparation of Example 50: ¹H NMR (500 MHz, pyridine-d₅) δ ppm 7.82 (d, J=1.1, 1H), 7.61-7.52 (t, 1H), 7.03 (d, J=7.2, 1H), 6.92 (s, 1H), 6.55 (d, J=8.6, 1H), 4.20 (dt, J=8.6, 6.6, 1H), 3.55-3.46 (m, 2H), 3.41 (dd, J=11.0, 7.0, 1H), 3.27 (dd, J=10.8, 4.0, 1H), 2.84-2.72 (m, 2H), 2.40 (d, J=0.5, 3H), 2.11 (dtd, J=11.2, 7.2, 3.9, 1H), 1.99 (dtd, J=12.3, 8.3, 3.9, 1H), 1.86 (dq, J=12.7, 8.7, 1H), 1.45-1.35 (m, 1H); MS (ESI+) m/z 337 (M+H)¹.

Example 68

(3aR,4S,5R,6aS)-5-(1H-imidazol-1-yl)-2-[6-(trifluoromethyl)pyridin-2-yl]octahydrocyclopenta[c]pyrrol-4-ol and

Example 69

(3aR,4S,5S,6aS)-5-(1H-imidazol-1-yl)-2-[6-(trifluoromethyl)pyridin-2-yl]octahydrocyclopenta[c]pyrrol-4-ol Step 1: To a solution of (3aR,6aS)-tert-butyl 4-oxohexahydrocyclopenta[c]pyrrole-2(1H)-carboxylate (4 g, 17.76 mmol), in tetrahydrofuran (30 mL) at 0° C. was added pyridinium bromide perbromide (6.62 g, 18.64 mmol). The mixture was stirred for 3 hours at room temperature, wherein an ice bath was needed to keep the mixture at about room temperature. The reaction mixture was quenched with 1 N NaHCO₃ solution (80 mL) and 1 N sodium thiosulfate (20 mL). The mixture was stirred for 0.5 hours and extracted with ethyl acetate. The organic layer was separated and concentrated. The crude product was purified chromatographically using a 40 g silica gel cartridge and eluting with a gradient of 0-3% methanol/dichloromethane over 20 minutes to give (3aR,6aS)-tert-butyl 5-bromo-4-oxohexahydrocyclopenta[c]pyrrole-2(1H)-carboxylate: MS (ESI+) m/z 321 (M+NH₄)⁺.

Step 2: A solution of (3aR,6aS)-tert-butyl 5-bromo-4-oxohexahydrocyclopenta[c]pyrrole-2(1H)-carboxylate (300 mg, 0.986 mmol) from Step 1, 1H-imidazole (201 mg, 2.96 mmol), and acetone (0.5 mL) in a 4 mL vial was stirred for 1.5 h at 80° C. The reaction mixture was then concentrated. The crude product was purified chromatographically using a 12 g silica gel cartridge with a gradient of 0-10% CH₃OH/CH₂Cl₂ over 20 min to give (3aR,6aS)-tert-butyl 5-(1H-imidazol-1-yl)-4-oxohexahydrocyclopenta[c]pyrrole-2(1H)-carboxylate: MS (ESI+) m/z 292 (M+H)⁺.

Step 3: (3aR,6aS)-tert-Butyl 5-(1H-imidazol-1-yl)-4-oxohexahydrocyclopenta[c]pyrrole-2(1H)-carboxylate (75 mg, 0.257 mmol) from Step 2 in methanol (2 mL) was cooled in a dry ice/acetone bath to −78° C., and sodium borohydride (11.69 mg, 0.309 mmol) was added. The reaction was allowed to warm to ambient temperature over 6 hours. Then the reaction mixture was partially concentrated, quenched with 10 mL of aqueous ammonium chloride, diluted with water, and extracted with 2×20 mL of ethyl acetate. The extracts were washed with brine, dried ($Na_2SO_4$) and filtered. The solvent was removed in vacuo. The crude product was purified using a 4 g silica gel cartridge with a gradient of 0-6% $CH_3OH$ (2 N $NH_3$)/$CH_2Cl_2$ over 20 minutes to give (3aR,6aS)-tert-butyl 4-hydroxy-5-(1H-imidazol-1-yl)hexahydrocyclopenta[c]pyrrole-2(1H)-carboxylate.

Step 4: In a 4 mL vial were combined (3aR,6aS)-tert-butyl 4-hydroxy-5-(1H-imidazol-1-yl)hexahydrocyclopenta[c]pyrrole-2(1H)-carboxylate (50 mg, 0.170 mmol) from Step 3 and 4 N HCl in 1,4-dioxane (0.554 mL, 2.216 mmol) to give a suspension. The reaction was stirred at room temperature for 6 hours, and then the solvent was removed in vacuo. The resulting HCl salt was triturated with 3 mL of 10% methanol (2 N ammonia)/dichloromethane and filtered to give crude (3aR,6aS)-5-(1H-imidazol-1-yl)octahydrocyclopenta[c]pyrrol-4-ol: MS (ESI+) m/z 398 (M+H)$^+$.

Step 5: The title compounds for Example 68 and Example 69 were prepared by substituting (3aR,6aS)-5-(1H-imidazol-1-yl)octahydrocyclopenta[c]pyrrol-4-ol from Step 4 for (3aS, 4S,6aS)—N-(3-fluorophenyl)octahydrocyclopenta[c]pyrrole-4-carboxamide in the procedure that describes the preparation of Example 56. The crude material was purified using a 12 g silica gel cartridge eluting with a gradient of 0-4.5% methanol (2 N ammonia)/dichloromethane over 20 minutes to give a mixture of the title compounds of Example 68 and Example 69. The title compounds of Example 68 and Example 69 were separated on preparative thin-layer chromatography plates (4×0.25 mm) eluted with 6% methanol (2 N ammonia)/dichloromethane:

Example 68: $^1$H NMR (500 MHz, pyridine-$d_5$) δ ppm 8.09 (s, 1H), 7.49 (t, J=7.9, 1H), 7.44 (s, 1H), 7.32 (s, 1H), 7.27 (d, J=5.0, 1H), 6.95 (d, J=7.2, 1H), 6.56 (d, J=8.6, 1H), 4.52 (ddd, J=11.6, 8.5, 3.5, 1H), 4.22 (dd, J=8.2, 4.3, 1H), 4.10 (d, J=10.7, 1H), 3.80 (t, J=9.4, 1H), 3.55 (t, J=9.8, 1H), 3.45 (dd, J=9.9, 6.8, 1H), 2.91-2.84 (m, 1H), 2.83-2.75 (m, 1H), 2.34-2.25 (m, 2H); MS (ESI+) m/z 339 (M+H)$^+$.

Example 69: $^1$H NMR (500 MHz, pyridine-$d_5$) δ ppm 8.06 (s, 1H), 7.55 (t, J=7.9, 1H), 7.38 (d, J=1.1, 1H), 7.36 (d, J=0.7, 1H), 7.02 (d, J=7.3, 1H), 6.64 (d, J=8.6, 1H), 4.63-4.56 (m, 1H), 4.56-4.51 (m, 1H), 4.32 (dd, J=11.3, 4.5, 1H), 3.58 (dd, J=11.0, 8.0, 1H), 3.49 (ddd, J=20.6, 11.0, 6.4, 2H), 3.03 (ddd, J=16.9, 8.7, 4.6, 1H), 2.82 (td, J=8.5, 2.9, 1H), 2.22 (ddd, J=13.3, 10.6, 9.5, 1H), 1.96 (ddd, J=13.4, 7.4, 2.2, 1H); MS (ESI+) m/z 339 (M+H)$^+$.

Example 70

(4R)-4-fluoro-N-{(3aR,4S,6aS)-4-methyl-2-[6-(trifluoromethyl)pyridin-2-yl]octahydrocyclopenta[c]pyrrol-4-yl}-L-prolinamide The title compound is prepared by treating a solution of (3aR,4S,6aS)-4-methyl-2-(6-(trifluoromethyl)pyridin-2-yl)octahydrocyclopenta[c]pyrrol-4-amine from Example 27 (0.075 g, 0.263 mmol) in 1 mL dichloromethane with (2S,4R)-1-(tert-butoxycarbonyl)-4-fluoropyrrolidine-2-carboxylic acid (0.067 g, 0.289 mmol) followed by of 1-hydroxybenzotriazole hydrate (0.044 g, 0.289 mmol). The reaction was stirred for 5 minutes, and then $N^1$-((ethylimino)methylene)-$N^3$,$N^3$-dimethylpropane-1,3-diamine (0.051 mL, 0.289 mmol) was added to the reaction mixture followed by stirring at ambient temperature overnight. The reaction was quenched with saturated aqueous sodium bicarbonate, and the crude material was chromatographed using a 12 g silica gel cartridge eluted with 3%-100% ethyl acetate/hexanes over 30 minutes to give (2S,4R)-tert-butyl 4-fluoro-2-((3aR,4S,6aS)-4-methyl-2-(6-(trifluoromethyl)pyridin-2-yl)octahydrocyclopenta[c]pyrrol-4-ylcarbamoyl)pyrrolidine-1-carboxylate which was treated with 4 N HCl in 1,4-dioxane (1 mL, 4.00 mmol). An oil slowly gummed out of solution. The reaction was stirred at room temperature for 18 hours, and the solvent was removed under a stream of nitrogen. The crude material was purified using a 12 g silica gel cartridge eluted with 1-10% methanol (2 N ammonia)/dichloromethane to give the title compound: $^1$H NMR (400 MHz, pyridine-$d_5$) δ ppm 8.03 (bs, 1H), 7.52 (m, 1H), 7.00 (d, J=7.2, 1H), 6.55 (d, J=8.5, 1H), 5.22 (dt, J=54.3, 3.5, 1H), 4.22-4.14 (m, 1H), 3.75-3.45 (m, 4H), 3.41-3.27 (m, 2H), 3.22-3.12 (m, 1H), 3.02-2.74 (m, 2H), 2.58 (dddd, J=23.7, 15.0, 8.5, 2.3, 1H), 2.32-2.11 (m, 2H), 1.99 (dq, J=13.3, 8.7, 1H), 1.78 (dt, J=13.2, 8.7, 1H), 1.48 (s, 3H), 1.46-1.13 (m, 1H); MS (ESI+) m/z 401 (M+H)$^+$.

Example 71

$N^2$-methyl-N-{(3aR,4S,6aS)-4-methyl-2-[6-(trifluoromethyl)pyridin-2-yl]octahydrocyclopenta[c]pyrrol-4-yl}-L-leucinamide The title compound was prepared by substituting N-(tert-butoxycarbonyl)-N-methyl-L-leucine for (2R,4S)-1-(tert-butoxycarbonyl)-4-fluoropyrrolidine-2-carboxylic acid in the procedure described in Example 70: $^1$H NMR (500 MHz, pyridine-$d_5$) δ ppm 7.89 (bs, 1H), 7.63 (m, 1H), 7.00 (d, J=7.2, 1H), 6.57 (d, J=8.6, 1H), 3.71-3.63 (m, 1H), 3.56 (dd, J=10.8, 7.8, 2H), 3.52 (dd, J=11.4, 6.6, 2H), 3.39-3.30 (m, 2H), 3.15 (dd, J=8.2, 5.8, 1H), 2.96-2.86 (m, 1H), 2.43 (s, 3H), 2.32-2.19 (m, 1H), 2.10 (q, J=8.9, 1H), 2.15-2.03 (m, 1H), 1.94-1.76 (m, 2H), 1.70 (ddd, J=13.5, 7.8, 5.7, 1H), 1.57 (m, 4H), 1.57 (s, 4H), 1.48-1.38 (m, 1H), 0.95 (d, J=6.6, 3H), 0.88 (d, J=6.5, 3H); MS (ESI+) m/z 413 (M+H)$^1$.

Example 72

4,4,4-trifluoro-N-{(3aR,4S,6aS)-4-methyl-2-[6-(trifluoromethyl)pyridin-2-yl]octahydrocyclopenta[c]pyrrol-4-yl}butanamide The title compound was prepared by substituting 4,4,4-trifluorobutanoic acid for (2R,4S)-1-(tert-butoxycarbonyl)-4-fluoropyrrolidine-2-carboxylic acid in the procedure described in Example 70 except the acidic deprotection was not performed: $^1$H NMR (500 MHz, pyridine-$d_5$) δ ppm 8.41 (bs, 1H), 7.55 (t, J=7.3, 1H), 7.00 (d, J=7.2, 1H), 6.56 (d, J=8.6, 1H), 3.68-3.60 (m, 1H), 3.59-3.50 (m, 2H), 3.38-3.29 (m, 2H), 2.98-2.88 (m, 1H), 2.79-2.65 (m, 2H), 2.65-2.59 (m, 2H), 2.26 (ddd, J=13.2, 8.3, 4.8, 1H), 2.08 (dq, J=13.2, 8.6, 1H), 1.84 (dt, J=13.3, 8.5, 1H), 1.56 (s, 3H), 1.55-1.26 (m, 1H); MS (ESI+) m/z 410 (M+H)$^1$.

Many variations in the invention will suggest themselves to those skilled in the art in light of the foregoing detailed description. All such obvious variations are within the full intended scope of the appended claims.

We claim:
1. A compound of formula (I),

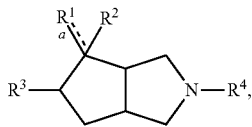

or a pharmaceutically acceptable salt thereof, wherein
α is a single bond;
$R^1$ is —N($R^x$)C(O)$G^3$;
$R^a$ and $R^b$, at each occurrence, are each independently hydrogen, alkyl, arylalkyl, halogen, haloalkyl, hydroxy, hydroxyalkyl, or $OR^{1a}$; wherein the aryl of arylalkyl is unsubstituted or substituted with 1, 2 3, 4, or 5 substituents independently selected from the group consisting of alkyl, haloalkyl, and halogen;
$R^{1a}$ is alkyl, aryl, arylalkyl, cycloalkyl, cycloalkylalkyl, or haloalkyl; wherein said aryl, the aryl of arylalkyl, cycloalkyl and the cycloalkyl of cycloalkylalkyl are independently unsubstituted or substituted with 1, 2 3, 4, or 5 substituents independently selected from the group consisting of alkyl, haloalkyl, and halogen;
$R^x$ is hydrogen or alkyl;
$R^{2a}$ is hydrogen, alkyl, aryl, arylalkyl, cycloalkyl, cycloalkylalkyl, or haloalkyl; wherein said aryl, the aryl of arylalkyl, cycloalkyl, and the cycloalkyl of cycloalkylalkyl are independently unsubstituted or substituted with 1, 2 3, 4, or 5 substituents independently selected from the group consisting of alkyl, haloalkyl, and halogen;
$R^{2b}$ is alkyl or haloalkyl;
$G^3$, at each occurrence, is independently aryl or heteroaryl; wherein $G^3$ at each occurrence is independently unsubstituted or substituted with 1, 2, 3, 4, or 5 substituents selected from the group consisting of alkyl, alkenyl, alkynyl, cyano, haloalkyl, halogen, nitro, N($R^{2a}$)$_2$, N($R^{2a}$)C(O)$R^{2a}$, O$R^{2a}$, C(O)$R^{2a}$, C(O)O$R^{2a}$, C(O)N($R^{2a}$)$_2$, SO$_2R^{2b}$, and SO$_2$N($R^{2a}$)$_2$;
m, at each occurrence, is independently 1, 2, 3, 4, 5, or 6;
$R^2$ is alkyl, haloalkyl, $G^3$ or —(C$R^aR^b$)$_m$-$G^3$;
$R^3$ is hydrogen, alkyl, haloalkyl, $G^3$ or —(C$R^aR^b$)$_m$-$G^3$;
$R^4$ is hydrogen, $G^5$, or —(C$R^aR^b$)$_m$-$G^3$; and
$G^5$ is aryl or heteroaryl; wherein $G^5$ is independently unsubstituted or substituted with 1, 2, 3, 4, or 5 substituents selected from the group consisting of alkyl, alkenyl, alkynyl, cyano, haloalkyl, halogen, nitro, N($R^{2a}$)$_2$, N($R^{2a}$)C(O)$R^{2a}$, O$R^{2a}$, C(O)$R^{2a}$, C(O)O$R^{2a}$, C(O)N($R^{2a}$)$_2$, SO$_2R^{2b}$, and SO$_2$N($R^{2a}$)$_2$; and wherein the $G^5$ is other than quinolizinone or quinolone.

2. The compound according to claim 1, or a pharmaceutically acceptable salt thereof, wherein
$R^1$ is —N($R^x$)C(O)$G^3$;
$R^2$ is alkyl; and
$R^3$ is hydrogen.

3. The compound according to claim 2, or a pharmaceutically acceptable salt thereof, wherein $R^2$ is methyl.

4. The compound according to claim 1 or a pharmaceutically acceptable salt thereof, selected from the group consisting of:
N-[(3aR,4R,6aS)-2-benzyl-4-methyloctahydrocyclopenta[c]pyrrol-4-yl]benzamide;
N-[(3aR,4S,6aS)-2-benzyl-4-methyloctahydrocyclopenta[c]pyrrol-4-yl]benzamide;
N-[(3aR,4R,6aS)-2-benzyl-4-methyloctahydrocyclopenta[c]pyrrol-4-yl]-3-fluorobenzamide;
N-[(3aR,4S, 6aS)-2-benzyl-4-methyloctahydrocyclopenta[c]pyrrol-4-yl]-3-fluorobenzamide;
N-[(3aR,4R,6aS)-4-methyloctahydrocyclopenta[c]pyrrol-4-yl]benzamide;
N-[(3aR,4S,6aS)-4-methyloctahydrocyclopenta[c]pyrrol-4-yl]benzamide;
3-fluoro-N-[(3aR,4R,6aS)-4-methyloctahydrocyclopenta[c]pyrrol-4-yl]benzamide;
3-fluoro-N-[(3aR,4S,6aS)-4-methyloctahydrocyclopenta[c]pyrrol-4-yl]benzamide;
N-{(3aR,4R, 6aS)-4-methyl-2-[6-(trifluoromethyl)pyridin-2-yl]octahydrocyclopenta[c]pyrrol-4-yl}benzamide;
N-{(3aR,4S, 6aS)-4-methyl-2-[6-(trifluoromethyl)pyridin-2-yl]octahydrocyclopenta[c]pyrrol-4-yl}benzamide;
3-fluoro-N-{(3aR,4R,6aS)-4-methyl-2-[6-(trifluoromethyl)pyridin-2-yl]octahydrocyclopenta[c]pyrrol-4-yl}benzamide;
3-fluoro-N-{(3aR,4S, 6aS)-4-methyl-2-[6-(trifluoromethyl)pyridin-2-yl]octahydrocyclopenta[c]pyrrol-4-yl}benzamide; and
pharmaceutically acceptable salts thereof.

5. A pharmaceutical composition comprising a therapeutically effective amount of a compound of formula (I) according to claim 1 or a pharmaceutically acceptable salt thereof, in combination with a pharmaceutically acceptable carrier.

6. A method of treating acute pain in a subject in need thereof, comprising:
administering to the subject a therapeutically suitable amount of a compound of formula (I) according to claim 1, or a pharmaceutically acceptable salt thereof.

7. A method of treating chronic pain in a subject in need thereof, comprising the step of: administering a therapeutically suitable amount of a compound of formula (I) according to claim 1, or a pharmaceutically acceptable salt thereof.

* * * * *